(12) United States Patent
Nemecek et al.

(10) Patent No.: US 7,786,114 B2
(45) Date of Patent: Aug. 31, 2010

(54) BIS-AZAINDOLE DERIVATIVES, PREPARATION AND PHARMACEUTICAL USE THEREOF AS KINASE INHIBITORS

(75) Inventors: Conception Nemecek, Orveau (FR); William A. Metz, Bridgewater, NJ (US); Sylvie Wentzler, L'Hay les Roses (FR); Dominique Lesuisse, Montreuil (FR); Youssef El-Ahmad, Creteil (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 11/692,321

(22) Filed: Mar. 28, 2007

(65) Prior Publication Data

US 2008/0045561 A1 Feb. 21, 2008

Related U.S. Application Data

(63) Continuation of application No. PCT/FR2005/002410, filed on Sep. 29, 2005.

(30) Foreign Application Priority Data

Oct. 1, 2004 (FR) ................................. 04 10386

(51) Int. Cl.
*A61K 31/535* (2006.01)
*A61K 31/44* (2006.01)
*A61K 31/497* (2006.01)
*C07D 401/00* (2006.01)
*C07D 413/00* (2006.01)

(52) U.S. Cl. .................... 514/234.5; 544/362; 544/127; 546/126; 514/300; 514/253.04

(58) Field of Classification Search ............... 514/234.5, 514/300, 253, 4; 544/362, 127; 546/126
See application file for complete search history.

(56) References Cited

FOREIGN PATENT DOCUMENTS

| WO | WO 03/000688 A1 | 1/2003 |
|---|---|---|
| WO | WO 03/000695 A1 | 1/2003 |
| WO | WO 03/024969 A1 | 3/2003 |
| WO | WO 03/044015 A2 | 5/2003 |

OTHER PUBLICATIONS

Hands et al. A convenient method for the preparation of 5-,6- and 7-azaindoles and their derivatives. Synthesis (Stuttgart), 1996.*
Jordan, V.C. Nature Reviews: Drug Discovery, 2, 2003, p. 205.*
Dorwald F. Zaragoza. Side Reviews in Organic Synthesis: A guide to successful synthesis design, Weinheim: Wiley-VCH, Verlag, GMBH & Co. KGaA, 2005, Preface.*
Wolff et al. Burger's Medicinal Chemistry and Drug Discovery—Fifth Edition, New York: John Wiley & Songs, 1996, vol. 1, pp. 975-976.*
Baserga, The IGF-I Receptor in Cancer Research, Exp. Cell. Res., 1999 (253) pp. 1-6.
Chan et. al, The Role of Protein Tyrosine Kinases and Protein Tyrosine Phosphatases in T Cell Antigen Receptor Signal Transduction, Annu. Rev. Immunol., 1994 (12) pp. 555-592.
Garcia-Echeverria et al, in vivo antitumor activity of NVP-AEW541—A novel, potent, and selective inhibitor of the IGF-IR kinase, Cancer Cell, 2004 (5) pp. 231-239.
Gualberto et al, Emerging role of insulin-like growth factor receptor inhibitors in oncology: early clinical trial results and future directions, Oncogene, 2009 (28) pp. 3009-3021.
Hanks et al, The Eukaryotic Protein Kinase Superfamily: Kinase (Catalytic) Domain Structure and Classification, FASEB, 1995 (9) pp. 576-596.
Iwashita et al, Signal Transduction System for Growth Factor Receptors Associated with Tyrosine Kinase Activity: Epidermal Growth Factor Receptor Signalling and its Regulation, Cellular Signalling, 1992 (4) 2 pp. 123-132.
Newton, Protein Kinase C: Structure, Function, and Regulation, J. Biol. Chem., 1995 (270) 48 pp. 28495-28498.
Pines, Cyclins and cyclin-dependent kinases: take your partners, Trends in Biochemical Sciences, 1993 (18) pp. 195-197.

* cited by examiner

*Primary Examiner*—Brandon J Fetterolf
*Assistant Examiner*—Anna Pagonakis
(74) *Attorney, Agent, or Firm*—Kelly L. Bender

(57) ABSTRACT

Compounds of formula (I):

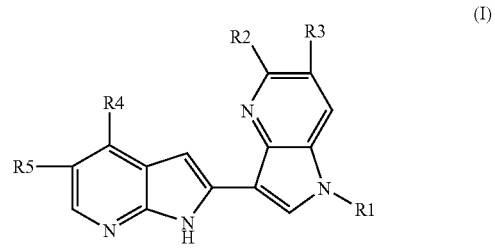

wherein R1, R2, R3, R4, and R5 have the meanings given in the description, and to salts thereof, pharmaceutical compositions comprising said compounds and the use thereof as protein kinase inhibitors.

6 Claims, No Drawings

BIS-AZAINDOLE DERIVATIVES, PREPARATION AND PHARMACEUTICAL USE THEREOF AS KINASE INHIBITORS

This application is a continuation of International Application No. PCT/FR2005/002410, filed Sep. 29, 2005, which claims the benefit of priority of French Patent Application No. 0410386, filed Oct. 1, 2004.

The present invention relates to novel bis-azaindole derivatives, their method of preparation, their application as medicinal products, pharmaceutical compositions containing them and the pharmaceutical use of said derivatives for the prevention and treatment of disorders that can be controlled by inhibition of protein kinase activity.

The present invention relates to novel bis-azaindole derivatives possessing protein kinase inhibitor effects.

The products of the present invention can thus be used notably for the prevention or treatment of disorders that can be controlled by the inhibition of protein kinase activity.

The inhibition and regulation of protein kinases constitute a powerful new mechanism of action for the treatment notably of a large number of solid and liquid tumors.

Such disorders that can be treated by the products of the present application are therefore, in particular, solid tumors.

Said protein kinases belong notably to the following group: IGF1, Raf, EGF, PDGF, VEGF, Tie2, KDR, Flt1-3, FAK, Src, Abl, CKit, cdk1-9, Aurora1-2, cdc7, Akt, Pdk, S6K, Jnk, IR, FLK-1, FGFR1, FGFR2, FGFR3, FGFR4, FGFR5, PLK, Pyk2, CDK7, CDK2 and EGFR.

Said protein kinases belong more particularly to the following group: IGF1, cdc7, Aurora1-2, Src, Jnk, FAK, KDR, IR, Tie2, CDK7, CDK2 and EGFR.

The protein kinase IGF1 (Insulin Growth Factor-1) may be mentioned in particular.

The present invention thus relates in particular to novel inhibitors of the IGF-1R receptor which can be used for treatments in oncology.

Cancer is still a disease for which the existing treatments are obviously inadequate. Certain protein kinases play an important role in many cancers. The inhibition of said protein kinases is potentially important in the chemotherapy of cancers notably to suppress tumor growth or survival. The present invention therefore relates to the identification of novel products that inhibit said protein kinases.

The protein kinases take part in the signaling events that control cell activation, growth and differentiation in response either to extracellular mediators, or to changes in the environment. In general, these kinases belong to two groups: those which phosphorylate serine and/or threonine residues preferentially and those which phosphorylate tyrosine residues preferentially [S. K. Hanks and T. Hunter, FASEB. J., 1995, 9, pages 576-596]. The serine/threonine kinases are for example the isoforms of protein kinases C [A. C. Newton, J. Biol. Chem., 1995, 270, pages 28495-28498] and a group of cycline-dependent kinases, such as cdc2 [J. Pines, Trends in Biochemical Sciences, 1995, 18, pages 195-197]. The tyrosine kinases comprise the growth factor receptors such as the epidermal growth factor (EGF) receptor [S. Iwashita and M. Kobayashi, Cellular Signalling, 1992, 4, pages 123-132], and cytosolic kinases such as p56tck, p59fYn, ZAP-70 and the csk kinases [C. Chan et al., Ann. Rev. Immunol., 1994, 12, pages 555-592].

Abnormally high levels of protein kinase activity have been implicated in many diseases, resulting from abnormal cellular function. This can arise, either directly or indirectly, from a dysfunction in the mechanisms of control of kinase activity, associated for example with a mutation, overexpression or inappropriate activation of the enzyme, or by over- or under-production of cytokines or of growth factors, also involved in signal transduction upstream or downstream from the kinases. In all these cases, selective inhibition of the action of the kinases offers the hope of a beneficial effect.

The type 1 receptor for the insulin-like growth factor (IGF-I-R) is a transmembrane receptor with tyrosine kinase activity that binds primarily to IGFI but also to IGFII and to insulin with a lower affinity. Binding of IGF1 to its receptor leads to oligomerization of the receptor, activation of tyrosine kinase, the intermolecular autophosphorylation and phosphorylation of cellular substrates (main substrates: IRS1 and Shc). The receptor activated by its ligand induces mitogenic activity in normal cells. However, IGF-I-R plays an important role in so-called abnormal growth.

Several clinical reports emphasize the important role of the IGF-I route in the development of human cancers:

IGF-I-R is often found to be overexpressed in many types of tumors (breast, colon, lung, sarcoma, myeloma, etc.) and its presence is often associated with a more aggressive phenotype.

High concentrations of circulating IGF1 are strongly correlated with a risk of cancer of the prostate, lung and breast.

Moreover, it has been widely documented that IGF-I-R is necessary for the establishment and maintenance of the transformed phenotype both in vitro and in vivo [Baserga R, Exp. Cell. Res., 1999, 253, pages 1-6]. The kinase activity of IGF-I-R is essential to the transformation activity of several oncogenes: EGFR, PDGFR, the large T antigen of the SV40 virus, activated Ras, Raf, and v-Src. Expression of IGF-I-R in normal fibroblasts induces a neoplastic phenotype, which can then lead to tumor formation in vivo. Expression of IGF-I-R plays an important role in substrate-independent growth. IGF-I-R has also been shown to be a protector in chemotherapy-induced and radiation-induced apoptosis, and apoptosis induced by cytokines. Moreover, inhibition of endogenous IGF-I-R by a dominant negative, triple helix formation or antisense expression causes suppression of transforming activity in vitro and reduction of tumor growth in animal models.

The present invention relates to products of formula (I):

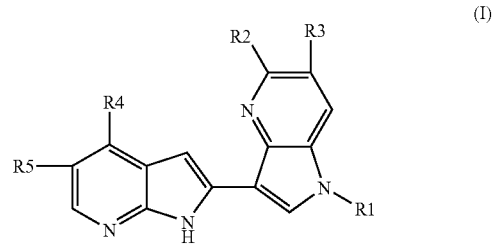

in which:

R1 represents the hydrogen atom, alkyl and alkenyl, optionally substituted;

R2 represents alkoxy, optionally substituted, and R3 represents alkyl and alkoxy, optionally substituted;

R4 represents the hydrogen atom; halogen atoms; the dioxolane radical; the —CH=O; —CH=N—OH; —CH=N— phenyl radicals with optionally substituted phenyl; and the cyano, alkyl and alkoxy radicals, optionally substituted;

R5 represents a hydrogen atom or a halogen atom;

p represents an integer from 2 to 4;

the phenyl, alkyl, alkenyl and alkoxy radicals represented by or contained in R1, R2, R3 or R4 being optionally substituted by one or more identical or different radicals selected from halogen atoms and the cyano; hydroxyl; oxo; nitro; —NR6R7; —C(=O)—NR6R7; —C(=O)—R9; —C(=O)—OR10; —N(R11)—C(=O)-R9; —N(R11)—C(=O)—OR10; —N(R11)—C(=O)—NR6R7; —S(O)n-R9; —N(R11)—S(O)n-R9; —S(O)n-NR6R7; —N(R11)—S(O)n-NR6R7; alkyl, alkoxy, alkylthio, cycloalkyl, heterocycloalkyl, aryl, aryloxy and heteroaryl radicals, optionally substituted;

R6 and R7, which may be identical or different, are selected from hydrogen, alkyl, alkoxy, alkenyl, cycloalkyl, cycloalkenyl, heterocycloalkyl, aryl, heteroaryl, cycloalkylalkyl, heterocycloalkylalkyl, aralkyl and heteroaralkyl, all these radicals being optionally substituted, or alternatively R6 and R7 form, with the nitrogen atom to which they are bound, a heterocyclic radical that is unsaturated or alternatively partially or fully saturated made up of 3 to 10 units and containing one or more heteroatoms selected from O, S, N and NR8, said heterocyclic radical being optionally substituted;

n represents an integer from 0 to 2;

R8 represents the hydrogen atom and the acyl, alkyl and aryl radicals, optionally substituted;

R9 represents alkyl, alkenyl, cycloalkyl, heterocycloalkyl, aryl, heteroaryl, cycloalkylalkyl, heterocycloalkylalkyl, aralkyl, and heteroaralkyl, all these radicals being optionally substituted;

R10 represents the values of R9 and hydrogen;

R11 represents hydrogen or alkyl, optionally substituted;

all these alkoxy, alkylthio, alkyl, alkenyl, cycloalkyl, heterocycloalkyl, aryl, heteroaryl, cycloalkylalkyl, heterocycloalkylalkyl, aralkyl, heteroaralkyl radicals that can be represented by R6, R7, R8, R9, R10 or R11 or that can constitute substituents of R1, R2, R3 and R4 as well as the heterocyclic radical that R6 and R7 can form with the nitrogen atom to which they are attached, being optionally substituted by one or more identical or different radicals selected from halogen atoms and the radicals hydroxyl; oxo; nitro; cyano; cycloalkyl; acyl; carboxy free or esterified; alkoxy optionally substituted; amino optionally substituted by one or two identical or different radicals selected from the radicals acyl, carboxy free or esterified, alkyl, phenyl and phenylalkyl, optionally substituted; pyrrolidinyl, piperidyl, piperazinyl, morpholinyl, alkyl, phenyl and phenylalkyl optionally substituted;

the above alkoxy, alkyl, pyrrolidinyl, piperidyl, piperazinyl, phenyl and phenylalkyl radicals, being optionally substituted by one or more radicals selected from halogen atoms and the hydroxyl, oxo, nitro, cyano, alkyl, hydroxyalkyl, CF3, alkoxy, hydroxyalkoxy, OCF3, carboxy free or esterified, amino, mono or dialkylamino, phenyl, phenylalkyl, pyrrolidinyl, piperidyl and pyridyl radicals;

all the above aryl, heteroaryl and heterocycloalkyl radicals being moreover optionally substituted by an alkylenedioxy radical;

all the above alkyl, alkenyl, alkoxy and alkylthio radicals being linear or branched and containing at most 6 carbon atoms;

all the above cycloalkyl radicals containing at most 7 carbon atoms;

all the above aryl, heteroaryl and heterocycloalkyl radicals containing at most 10 carbon atoms;

said products of formula (I) being in all possible isomeric forms: racemic, enantiomeric and diastereoisomeric, as well as the addition salts with organic and inorganic acids or with organic and inorganic bases of said products of formula (I).

One subject of the present invention is thus the products of formula (I) as defined above in which:

R1 represents alkyl and alkenyl, optionally substituted;

R2 represents alkoxy optionally substituted and R3 represents alkyl and alkoxy, optionally substituted;

R4 represents the hydrogen atom, the halogen atoms and the cyano, alkyl and alkoxy radicals, optionally substituted;

R5 represents a hydrogen or a halogen atom;

p represents an integer from 2 to 4;

the alkyl, alkenyl and alkoxy radicals represented by R1, R2, R3 or R4 being optionally substituted by one or more identical or different radicals selected from halogen atoms and the following radicals: cyano; hydroxyl; oxo; nitro; —NR6R7; —C(=O)—NR6R7; —C(=O)—R9; —C(=O)—OR10; —N(R11)—C(=O)—R9; —N(R11)—C(=O)—OR10; —N(R11)—C(=O)—NR6R7; —S(O)n-R9; —N(R11)—S(O)n-R9; —S(O)n-NR6R7; —N(R11)—S(O)n-NR6R7; alkyl, alkoxy, alkylthio, cycloalkyl, heterocycloalkyl, aryl and heteroaryl, optionally substituted;

R6 and R7, which may be identical or different, are selected from hydrogen, alkyl, alkenyl, cycloalkyl, cycloalkenyl, heterocycloalkyl, aryl, heteroaryl, cycloalkylalkyl, heterocycloalkylalkyl, arylalkyl and heteroarylalkyl, all these radicals being optionally substituted, or alternatively R6 and R7 form, with the nitrogen atom to which they are bound, a heterocyclic radical, unsaturated or alternatively partially or fully saturated, made up of 3 to 10 units and containing one or more heteroatoms selected from O, S, N and NR8, this heterocyclic radical being optionally substituted;

n represents an integer from 0 to 2;

R8 represents the hydrogen atom and the acyl, alkyl and aryl radicals, optionally substituted;

R9 represents alkyl, alkenyl, cycloalkyl, heterocycloalkyl, aryl, heteroaryl, cycloalkylalkyl, heterocycloalkylalkyl, arylalkyl and heteroarylalkyl, all these radicals being optionally substituted;

R10 represents the values of R9 and hydrogen;

R11 represents hydrogen or alkyl, optionally substituted alkyl;

all these alkoxy, alkylthio, alkyl, alkenyl, cycloalkyl, heterocycloalkyl, aryl, heteroaryl, cycloalkylalkyl, heterocycloalkylalkyl, arylalkyl and heteroarylalkyl radicals which can be represented by R6, R7, R8, R9, R10 or R11 or which can constitute substituents of R1, R2, R3 and R4 as well as the heterocyclic radical that may be formed by R6 and R7 with the nitrogen atom to which they are attached, being optionally substituted by one or more identical or different radicals selected from halogen atoms and the following radicals: hydroxyl; oxo; nitro; cyano; cycloalkyl; acyl; carboxy free or esterified; alkoxy optionally substituted; amino optionally substituted by one or two identical or different radicals selected from acyl, alkyl, phenyl and phenylalkyl radicals, optionally substituted; pyrrolidinyl, piperidyl, piperazinyl, alkyl, phenyl and phenylalkyl, optionally substituted;

the above alkoxy, alkyl, pyrrolidinyl, piperidyl, piperazinyl, phenyl and phenylalkyl radicals being optionally substituted by one or more radicals selected from halogen atoms and the radicals hydroxyl, oxo, nitro, cyano, alkyl, hydroxyalkyl, CF3, alkoxy, hydroxyalkoxy, OCF3, carboxy free or esterified, amino, mono or dialkylamino, phenyl, phenylalkyl, pyrrolidinyl, piperidyl and pyridyl;

all the above aryl, heteroaryl and heterocycloalkyl radicals being moreover optionally substituted by an alkylenedioxy radical;

all the above alkyl, alkenyl, alkoxy and alkylthio radicals being linear or branched and containing at most 6 carbon atoms;

all the above cycloalkyl radicals containing at most 7 carbon atoms;

all the above aryl, heteroaryl and heterocycloalkyl radicals containing at most 10 carbon atoms;

said products of formula (I) being in all the isomeric forms possible: racemic, enantiomeric and diastereoisomeric, as well as the salts of addition with organic and inorganic acids or with organic and inorganic bases of said products of formula (I).

In the products of formula (I) and hereinafter, the terms stated have the following meanings:

the term "Hal", "Halo" or halogen denotes atoms of fluorine, of chlorine, of bromine or of iodine.

the term alkyl radical or alk denotes a linear or branched radical containing at most 12 carbon atoms selected from the methyl, ethyl, propyl, isopropyl, butyl, isobutyl, sec-butyl, tert-butyl, pentyl, isopentyl, sec-pentyl, tert-pentyl, neo-pentyl, hexyl, isohexyl, sec-hexyl, tert-hexyl and also heptyl, octyl, nonyl, decyl, undecyl and dodecyl radicals, as well as their linear or branched positional isomers.

We may mention more particularly the alkyl radicals having at most 6 carbon atoms and notably the radicals methyl, ethyl, propyl, isopropyl, n-butyl, isobutyl, terbutyl, pentyl linear or branched, hexyl linear or branched.

the term alkenyl radical denotes a linear or branched radical containing at most 12 carbon atoms and preferably 4 carbon atoms selected for example from the following values: ethenyl or vinyl, propenyl or allyl, 1-propenyl, n-butenyl, i-butenyl, 3-methylbut-2-enyl, n-pentenyl, hexenyl, heptenyl, octenyl, cyclohexylbutenyl and decenyl as well as their linear or branched positional isomers.

Among the alkenyl values, we may mention more particularly the allyl or butenyl values.

the term alkoxy or O-alkyl radical denotes a linear or branched radical containing at most 12 carbon atoms and preferably 6 carbon atoms selected for example from the methoxy, ethoxy, propoxy, isopropoxy, linear, secondary or tertiary butoxy; pentoxy, hexoxy and heptoxy radicals, as well as their linear or branched positional isomers.

the term alkoxycarbonyl or alkyl-O—CO— radical denotes a linear or branched radical containing at most 12 carbon atoms in which the alkyl radical has the meaning stated above: we may mention for example the methoxy- and ethoxycarbonyl radicals.

the term alkylenedioxy or —O-alkylene-O— radical denotes a linear or branched radical containing at most 12 carbon atoms in which the alkylene radical has the meaning stated above: we may mention for example the methylenedioxy and ethylenedioxy radicals.

the term alkylsulfinyl or alkyl-SO— denotes a linear or branched radical containing at most 12 carbon atoms in which the alkyl radical has the meaning stated above and preferably contains 4 carbon atoms.

The term alkylsulfonyl or alkyl-SO2- denotes a linear or branched radical containing at most 12 carbon atoms in which the alkyl radical has the meaning stated above and preferably contains 4 carbon atoms.

the term alkylsulfonylcarbamoyl or alkyl-SO2-NH—C (=O)— denotes a linear or branched radical containing at most 12 carbon atoms in which the alkyl radical has the meaning stated above and preferably contains 4 carbon atoms.

the term alkylthio or alkyl-S— denotes a linear or branched radical containing at most 12 carbon atoms and represents notably the methylthio, ethylthio, isopropylthio and heptylthio radicals.

the term cycloalkyl radical denotes a monocyclic or bicyclic carbocyclic radical containing from 3 to 10 units and denotes notably the cyclopropyl, cyclobutyl, cyclopentyl and cyclohexyl radicals, the term —O-cycloalkyl radical denotes a radical in which the cycloalkyl radical has the meaning stated above the term cycloalkenyl radical denotes a monocyclic or bicyclic nonaromatic carbocyclic radical containing at least one double bond and containing from 3 to 10 units and denotes notably the cyclobutenyl, cyclopentenyl or cyclohexenyl radicals.

the term cycloalkylalkyl radical denotes a radical in which cycloalkyl and alkyl are selected from the values stated above: this radical thus denotes for example the cyclopropylmethyl, cyclopentylmethyl, cyclohexylmethyl and cycloheptylmethyl radicals.

the term acyl or r-CO— radical denotes a linear or branched radical containing at most 12 carbon atoms in which the radical r represents a hydrogen atom, an alkyl, cycloalkyl, cycloalkenyl, cycloalkyl, heterocycloalkyl, aryl or heteroaryl radical, these radicals having the values optionally substituted stated above or hereafter: thus the acyl radical represents notably CO-alkyl, CO-aryl or CO-heteroaryl. We may mention for example the formyl, acetyl, propionyl, butyryl or benzoyl radicals, or moreover valeryl, hexanoyl, acryloyl, crotonoyl, carbamoyl, pyrrolidinylcarboxy or moreover furylcarboxy.

By acyloxy radical, we mean the acyl-O— radicals in which acyl has the meaning stated above: we may mention for example the acetoxy or propionyloxy radicals.

By acylamino radical, we mean the acyl-NH— radicals in which acyl has the meaning stated above.

the term aryl radical denotes unsaturated radicals, monocyclic or consisting of carbocyclic condensed rings. As examples of said aryl radical, we may mention the phenyl or naphthyl radicals.

We may mention more particularly the phenyl radical.

By aralkyl we mean the radicals resulting from the combination of the alkyl radicals mentioned above, optionally substituted, and the aryl radicals also mentioned above, optionally substituted: we may mention for example the benzyl, phenylethyl, 2-phenethyl, triphenylmethyl or naphthlenemethyl radicals.

By aryloxy we mean aryl-O— radicals in which the aryl radicals are selected from the aryl radicals mentioned above, which are optionally substituted: mention is made, for example, of phenoxy and naphthyloxy radicals.

the term heterocyclic radical denotes a carbocyclic radical, saturated (heterocycloalkyl) or unsaturated (heteroaryl), made up at most of 6 units interrupted by one or more heteroatoms, identical or different, selected from oxygen, nitrogen or sulfur atoms.

As heterocycloalkyl radicals, we may mention notably the following radicals: dioxolane, dioxane, dithiolane, thiooxolane, thiooxane, oxiranyl, oxolanyl, dioxolanyl, piperazinyl, piperidinyl, pyrrolidinyl, imidazolidinyl, pyrazolidinyl, morpholinyl or moreover tetrahydrofuryl, tetrahydrothienyl, chromanyl, dihydrobenzofuranyl, indolinyl, piperidinyl, perhydropyranyl, pyrindolinyl, tetrahydroquinoleinyl, tetrahydroisoquinoleinyl or thioazolidinyl, piperidyl; tetrahydrofuran-2-yl, imidazolinyl, dihydropyrrolyl, tetrahydropyrrolyl, diazepine, perhydro-1,4-diazepine, tetrahydro-pyrrolo[3,4- c]pyrrol-2-one, tetrahydro-pyrrolo[3,4-c]pyrrole-1,3-dione and 1,4-dioxa-8-aza-spiro[4.5]decane, all these radicals being optionally substituted.

Among the heterocycloalkyl radicals, we may mention notably the following radicals: piperazinyl, piperidinyl, pyrrolidinyl, imidazolidinyl, pyrazolidinyl, morpholinyl, thioazolidinyl, piperidyl; tetrahydro-furan-2-yl, imidazolinyl, dihydropyrrolyl, tetrahydro-pyrrolyl, diazepine, perhydro-1,4-diazepine, tetrahydro-pyrrolo[3,4-c]pyrrol-2-one, tetrahydro-pyrrolo[3,4-c]pyrrole-1,3-dione and 1,4-dioxa-8-aza-spiro[4,5]decane, all these radicals being optionally substituted:

By heterocycloalkylalkyl radical, we mean the radicals in which the heterocycloalkyl and alkyl residues have the meanings given above.

Among the 5-unit heteroaryl radicals we may mention the furyl radicals such as 2-furyl, thienyl radicals such as 2-thienyl and 3-thienyl, pyrrolyl, diazolyl, thiazolyl, thiadiazolyl, thiatriazolyl, isothiazolyl, oxazolyl oxadiazolyl, 3- or 4-isoxazolyl, imidazolyl, pyrazolyl, and isoxazolyl radicals.

Among the 6-unit heteroaryl radicals we may mention notably the pyridyl radicals such as 2-pyridyl, 3-pyridyl and 4-pyridyl, pyrimidyl, pyrimidinyl, pyridazinyl, pyrazinyl and tetrazolyl radicals.

As condensed heteroaryl radicals containing at least one heteroatom selected from sulfur, nitrogen and oxygen, we may mention for example benzothienyl such as 3-benzothienyl, benzofuryl, benzopyranyl, benzofuranyl, benzopyrrolyl, benzimidazolyl, benzoxazolyl, thionaphthyl, indolyl, purinyl, quinoleinyl, isoquinoleinyl and naphthyridinyl.

Among the condensed heteroaryl radicals, we may mention more particularly the radicals benzothienyl, benzofuranyl, indolyl or quinoleinyl, benzimidazolyl, benzothiazolyl, furyl, imidazolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, 1,3,4-thiadiazolyl, thiazolyl, thienyl and triazolyl groups, these radicals being optionally substituted as stated for the heteroaryl radicals.

the term cyclic amine denotes a cycloalkyl radical containing from 3 to 8 units in which a carbon atom is replaced by a nitrogen atom, the cycloalkyl radical having the meaning given above and that can also contain one or more other heteroatoms selected from O, S, SO2, N or NR9 with R9 as defined above, as examples of said cyclic amines we may mention for example the pyrrolidinyl, piperidinyl, morpholinyl, piperazinyl, indolinyl, pyrindolinyl or tetrahydroquinoleinyl radicals, these radicals being optionally substituted.

The term patient denotes human beings but also the other mammals.

The term "Prodrug" denotes a product that can be transformed in vivo by metabolic mechanisms (such as hydrolysis) to a product of formula (I). For example, an ester of a product of formula (I) containing a hydroxyl group can be converted by hydrolysis in vivo to its parent molecule. Or moreover, an ester of a product of formula (I) containing a carboxy group can be converted by hydrolysis in vivo to its parent molecule.

We may mention as examples esters of products of formula (I) containing a hydroxyl group such as the acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexyl-sulfamates and quinates.

Particularly useful esters of products of formula (I) containing a hydroxyl group can be prepared starting from acid residues such as those described by Bundgaard et al., J. Med. Chem., 1989, 32, page 2503-2507: these esters include, notably, substituted (aminomethyl)-benzoates, dialkylamino-methylbenzoates in which the two alkyl groups can be bound to one another or can be interrupted by an oxygen atom or by a nitrogen atom optionally substituted or an alkylated nitrogen atom or moreover (morpholino-methyl)benzoates, e.g. 3- or 4-(morpholinomethyl)-benzoates, and (4-alkylpiperazin-1-yl) benzoates, e.g. 3- or 4-(4-alkylpiperazin-1-yl)benzoates.

The carboxy radical or radicals of the products of formula (I) can be salified or esterified by the various groups familiar to a person skilled in the art among which we may mention, as nonlimiting examples, the following compounds.

among the compounds of salification, inorganic bases such as, for example, an equivalent of sodium, of potassium, of lithium, of calcium, of magnesium or of ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine, among the compounds of esterification, the alkyl radicals for forming alkoxycarbonyl groups such as, for example, methoxycarbonyl, ethoxycarbonyl, tert-butoxy-carbonyl or benzyloxycarbonyl, and these alkyl radicals can be substituted by radicals selected for example from halogen atoms, hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethyl-aminoethyl, benzyl or phenethyl groups.

By esterified carboxy we mean for example radicals such as the alkyloxycarbonyl radicals for example methoxycarbonyl, ethoxycarbonyl, propoxycarbonyl, butyl or tert-butyloxycarbonyl, cyclobutyloxycarbonyl, cyclopentyloxy-carbonyl or cyclohexyloxycarbonyl.

We may also mention radicals formed with the readily cleavable ester residues such as the methoxymethyl, ethoxymethyl radicals; the acyloxyalkyl radicals such as pivaloyloxymethyl, pivaloyloxyethyl, acetoxymethyl or acetoxyethyl; the alkyloxycarbonyloxyalkyl radicals such as the methoxycarbonyloxy-methyl or -ethyl radicals, the isopropyloxycarbonyloxy-methyl or -ethyl radicals.

A list of said ester radicals can be found for example in European patent EP 0 034 536.

By amidated carboxy we mean radicals of the type —CONR6R7 as defined above or hereafter.

By alkyl- or dialkyl-amino radical, we mean radicals in which the alkyl radical or radicals preferably have 1 to 4 carbon atoms such as the methyl, ethyl, propyl, isopropyl, butyl, isobutyl, sec-butyl or tert-butyl radicals: we thus have for example the methylamino, ethylamino, propylamino or butylamino radicals, linear or branched, and the dimethylamino, diethylamino, methylethylamino radicals.

The amino radicals can also contain one or two heterocycles which can optionally contain an additional heteroatom. We may mention for example the pyrrolyl, imidazolyl, indolyl, piperidinyl, morpholinyl and piperazinyl radicals and especially the piperidinyl, morpholinyl or piperazinyl radicals.

By salified carboxy we mean the salts formed for example with an equivalent of sodium, of potassium, of lithium, of calcium, of magnesium or of ammonium. We may also mention the salts formed with organic bases such as methylamine, propylamine, trimethylamine, diethylamine, triethylamine. The sodium salt is preferred.

When the products of formula (I) contain an amino radical salifiable by an acid it is understood that these salts of acids also form part of the invention. We may mention the salts supplied by hydrochloric or methanesulfonic acids for example.

The addition salts with organic or inorganic acids of the products of formula (I) can be, for example, the salts formed with the hydrochloric, hydrobromic, hydriodic, nitric, sulfuric, phosphoric, propionic, acetic, trifluoroacetic, formic, benzoic, maleic, fumaric, succinic, tartaric, citric, oxalic, glyoxylic, aspartic, ascorbic acids, the alkylmonosulfonic acids such as for example methanesulfonic acid, ethanesulfonic acid, propanesulfonic acid, the alkyldisulfonic acids such as for example methanedisulfonic acid, alpha, beta-ethanedisulfonic acid, the arylmonosulfonic acids such as benzenesulfonic acid and the aryldisulfonic acids.

It may be recalled that stereoisomerism can be defined broadly as the isomerism of compounds having the same structural formulas, but in which the various groups are arranged differently in space, such as notably in monosubstituted cyclohexanes in which the substituent can be in the axial or equatorial position, and the various possible rotational conformations of ethane derivatives. However, there is another type of stereoisomerism, due to different spatial arrangements of fixed substituents, either on double bonds, or on rings, which is often called geometric isomerism or cis-trans isomerism. The term stereoisomer is used in the present application in its widest sense and therefore relates to all of the compounds mentioned above.

The present invention thus relates to the products of formula (I) as defined above and in the present invention in which R1 represents alkyl and alkenyl, optionally substituted;
R2 represents alkoxy optionally substituted and R3 represents alkyl and alkoxy, optionally substituted;
R4 represents the hydrogen atom, halogen atoms and the cyano, alkoxy and alkyl radicals, optionally substituted;
R5 represents a hydrogen atom or a halogen atom;
the alkyl, alkenyl and alkoxy radicals represented by R1, R2, R3 or R4 being optionally substituted by one or more identical or different radicals selected from halogen atoms and the following radicals: hydroxyl; oxo; nitro; —NR6R7; —C(=O)—NR6R7; —C(=O)—R9; —C(=O)—OR10; —N(R11)—C(=O)—R9; —N(R11)—C(=O)—OR10; —N(R11)—C(=O)—NR6R7; alkyl, alkoxy, alkylthio, cycloalkyl, heterocycloalkyl, phenyl and heteroaryl, optionally substituted;
R6 and R7, which may be identical or different, are selected from hydrogen and the alkyl, cycloalkyl, heterocycloalkyl, phenyl and heteroaryl radicals, all these radicals being optionally substituted;
or alternatively R6 and R7 form, with the nitrogen atom to which they are bound, a heterocyclic radical unsaturated or else partially or fully saturated made up of 3 to 10 units and containing one or more heteroatoms selected from O, S, N and NR8, this heterocyclic radical being optionally substituted;
R8 represents hydrogen, acyl, alkyl and phenyl, optionally substituted;
R9 represents alkyl, cycloalkyl, heterocycloalkyl, phenyl and heteroaryl, all these radicals being optionally substituted;
R10 represents the values of R9 and hydrogen;
R11 represents hydrogen or alkyl optionally substituted;

the alkoxy, alkylthio, alkyl, cycloalkyl, heterocycloalkyl, phenyl, and heteroaryl radicals, which can be represented by R6, R7, R8, R9, R10 or R11 or which can constitute substituents of R1, R2, R3 and R4 as well as the heterocyclic radical that R6 and R7 can form with the nitrogen atom to which they are attached, being optionally substituted by one or more identical or different radicals selected from halogen atoms and the following radicals: hydroxyl; oxo; nitro; cyano; cycloalkyl; carboxy free or esterified; alkoxy; OCF3; hydroxyalkoxy; amino being optionally substituted by one or two identical or different radicals selected from the acyl, alkyl, phenyl and phenylalkyl radicals, themselves optionally substituted; pyrrolidinyl, piperidyl and piperazinyl, themselves optionally substituted by one or more radicals selected from the following radicals: hydroxyl, alkyl, alkoxy, carboxy free or esterified, phenyl and phenylalkyl; alkyl, phenyl and phenylalkyl optionally substituted;
the above alkyl, phenyl and phenylalkyl radicals being optionally substituted by one or more radicals selected from halogen atoms and the following radicals: hydroxyl, nitro, cyano, alkyl, CF3, alkoxy, hydroxyalkoxy, OCF3, carboxy free or esterified, amino, mono- and di-alkylamino, phenyl, pyrrolidinyl and pyridyl;
the phenyl and phenylalkyl radicals being moreover optionally substituted by a dioxol radical;
all the above alkyl, alkenyl, alkoxy and alkylthio radicals being linear or branched and containing at most 4 carbon atoms;
all the above cycloalkyl radicals containing at most 6 carbon atoms;
all the above heteroaryl and heterocycloalkyl radicals containing at most 10 carbon atoms;
said products of formula (I) being in all possible isomeric forms: racemic, enantiomeric and diastereoisomeric, as well as the addition salts with organic and inorganic acids or with organic and inorganic bases of said products of formula (I).

The present invention thus relates to the products of formula (I) as defined above and in the present invention in which R1 represents alkyl or alkenyl, optionally substituted;
R2 represents alkoxy, optionally substituted;
R3 represents alkyl and alkoxy, optionally substituted;
R4 represents the hydrogen atom, halogen atoms and the cyano and alkyl radicals, optionally substituted;
R5 represents hydrogen or halogen;
the alkyl, alkenyl and alkoxy radicals represented by R1, R2, R3 or R4 being optionally substituted by one or more identical or different radicals selected from halogen atoms; and the following radicals: hydroxyl; —NR6R7; —CO—NR6R7; carboxy free or esterified; alkoxy; heterocycloalkyl, heteroaryl and phenyl optionally substituted by one or more identical or different radicals selected from halogen atoms and the following radicals: hydroxyl, nitro, cyano, alkyl, CF3, carboxy free or esterified, alkoxy and phenyl;
R6 and R7, which may be identical or different, are selected from hydrogen and the alkyl, cycloalkyl, phenyl and heterocyclic radicals such as pyrrolidinyl, piperidyl, pyrimidinyl, thienyl, thiazolyl, pyran, furyl, tetrahydrofuryl, tetrahydrofuran-2-yl, imidazolinyl, piperazinyl, indolyl, pyrrole, benzopyran, quinolyl, pyridyl, purinyl and morpholinyl radicals, all these radicals being optionally substituted;
or alternatively R6 and R7 form, with the nitrogen atom to which they are bound, a heterocyclic radical selected from the following radicals: pyrrolidinyl; imidazolyl; thiazolyl; diazepine; piperidyl; morpholinyl; piperazinyl; perhydro-1,4-diazepine; spiro [4.5]decane; pyrrolyl; dihydropyrrolyl; tetrahydropyrrolyl; tetrahydro-pyrrolo[3,4-c]pyrrolyl; 1-tetrahydro-pyrrolo[3,4-c]pyrrol-2-one; piperidinyl; indolinyl; pyrindolinyl; tetrahydro-quinoleinyl; thiazolidinyl; naphthyridyl; azetidine; or quinazolinyl; these radicals all being optionally substituted;

the alkyl, phenyl and heterocyclic radicals that can be represented by R6 and R7 as well as the heterocycle that can be formed by R6 and R7 with the nitrogen atom to which they are bound, being optionally substituted by one or more radicals selected from halogen atoms and the following radicals: hydroxyl; oxo; nitro; cyano; carboxy free or esterified; alkoxy; OCF3; amino optionally substituted by one or two identical or different radicals selected from acyl, alkyl, hydroxyalkyl, alkoxyalkyl, phenyl and phenylalkyl optionally substituted; pyrrolidinyl; piperidyl; piperazinyl; alkyl, phenyl and phenylalkyl optionally substituted;

the above alkyl, phenyl and phenylalkyl radicals being optionally substituted by one or more identical or different radicals selected from halogen atoms and the radicals hydroxyl, nitro, cyano, alkyl, CF3, alkoxy, hydroxyalkoxy, carboxy free or esterified, phenyl and pyridyl;

all the alkyl and alkoxy radicals being linear or branched and containing at most 4 carbon atoms;

said products of formula (I) being in all possible isomeric forms: racemic, enantiomeric and diastereoisomeric, as well as the addition salts with organic and inorganic acids or with organic and inorganic bases of said products of formula (I).

The present invention thus relates to the products of formula (I) as defined above in which R1, R2, R3, R4 and R5 have the meanings stated above and R6 and R7, which may be identical or different, are selected from the radicals hydrogen, alkyl, hydroxyalkyl, pyrrolidinylalkyl, piperidylalkyl, piperazinylalkyl, phenyl and phenylalkyl in which the alkyl, phenyl and piperazinyl radicals are optionally substituted;

or alternatively R6 and R7 can form, with the nitrogen atom to which they are bound, a heterocyclic radical selected from the following radicals: thiazolyl; diazepine; perhydro-1,4-diazepine; 1-tetrahydro-pyrrolo[3,4-c]pyrrol-2-one; piperidyl; morpholinyl; piperazinyl; all these radicals being optionally substituted;

the above alkyl, phenyl and piperazinyl radicals as well as the heterocycle that can be formed by R6 and R7 with the nitrogen atom to which they are bound, being optionally substituted by one or more identical or different radicals selected from the hydroxyl; oxo; piperidyl; alkyl and phenyl radicals, themselves optionally substituted by one or more identical or different radicals selected from the halogen atoms and the hydroxyl, alkoxy and hydroxyalkoxy radicals; the phenyl radicals being moreover optionally substituted by one or more alkyl radicals;

the alkyl and alkoxy radicals containing at most 4 carbon atoms;

said products of formula (I) being in all possible isomeric forms: racemic, enantiomeric and diastereoisomeric, as well as the addition salts with organic and inorganic acids or with organic and inorganic bases of said products of formula (I).

One subject of the present invention is thus the products of formula (I) as defined above in which R1, R2, R3, R4 and R5 have the meanings given above and R6 and R7, which may be identical or different, are selected from hydrogen, alkyl, hydroxyalkyl, pyrrolidinylalkyl, piperidylalkyl, piperazinylalkyl, phenyl and phenylalkyl radicals in which the alkyl, phenyl and piperazinyl radicals are optionally substituted;

or alternatively R6 and R7 may form with the nitrogen atom to which they are attached a heterocyclic radical selected from the following radicals: thiazolyl; diazepine; perhydro-1,4-diazepine; 1-tetrahydropyrrolo[3,4-c]pyrrol-2-one; piperidyl; morpholinyl; piperazinyl; all these radicals being optionally substituted;

the above alkyl, phenyl and piperazinyl radicals, and also the heterocycle that may be formed by R6 and R7 with the nitrogen atom to which they are attached, being optionally substituted by one or more identical or different radicals selected from the following radicals: hydroxyl; oxo; piperidyl; alkyl and phenyl which are themselves optionally substituted by one or more identical or different radicals selected from halogen atoms and hydroxyl, alkoxy and hydroxyalkoxy radicals;

the phenyl radicals moreover being optionally substituted by one or more alkyl radicals;

the alkyl and alkoxy radicals containing at most 4 carbon atoms;

said products of formula (I) being in all the isomeric forms possible: racemic, enantiomeric and diastereoisomeric, as well as the addition salts with organic and inorganic acids or with organic and inorganic bases of said products of formula (I).

One subject of the present invention is thus the products of formula (I) as defined above in which R1a represents hydrogen, alkyl optionally substituted by one or more identical or different substituents selected from the halogen atoms; the alkoxy radical, itself optionally substituted by hydroxyl or alkoxy; the radical NR6R7 or the radical —C(=O)—NR6R7 as defined in any one of the other claims;

R2a and R3a, which may be identical or different, represent alkoxy;

R4a represents the hydrogen atom; halogen atoms; the dioxolane radical; the —CH=O; —CH=N—OH; —CH=N-phenyl radicals with phenyl optionally substituted by —OH or alkoxy; and the cyano and alkyl radicals, optionally substituted by one or more identical or different radicals selected from halogen atoms, hydroxyl, alkoxy, phenoxy or thiophenylsulfanyl radicals and the radical NR6R7 as defined in any one of the other claims;

R5a represents the hydrogen atom and the atoms of chlorine and fluorine;

said products of formula (I) being in all possible isomeric forms: racemic, enantiomeric and diastereoisomeric, as well as the addition salts with organic and inorganic acids or with organic and inorganic bases of said products of formula (I).

The present invention thus relates to the products of formula (I) as defined above corresponding to formula (Ia):

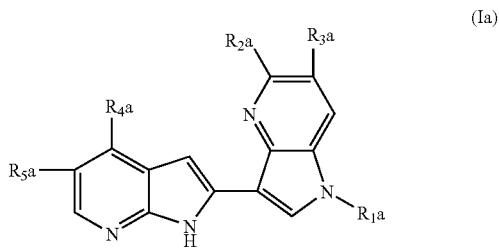

(Ia)

in which:

R1a represents alkyl optionally substituted by the radical NR6R7 as defined above;

R2a and R3a, identical or different, represent alkoxy;

R4a represents the hydrogen atom, halogen atoms and the cyano and alkyl radicals optionally substituted by one or more radicals selected from halogen atoms, the alkoxy radicals and the radical NR6R7 as defined above

R5a represents the hydrogen atom and chlorine and fluorine atoms;

said products of formula (Ia) being in all possible isomeric forms: racemic, enantiomeric and diastereoisomeric, as well as the addition salts with organic and inorganic acids or with organic and inorganic bases of said products of formula (Ia).

Notably R6 and R7 can form, with the nitrogen atom to which they are bound, a heterocyclic radical selected from the following radicals: thiazolyl; diazepine; piperidyl; morpholinyl; and piperazinyl; these radicals being optionally substituted as stated above;

Thus R6 and R7 can form, with the nitrogen atom to which they are bound, a thiazolyl radical; diazepine optionally substituted by an alkyl radical; piperidyl optionally substituted by hydroxyl, alkyl, hydroxyalkyl or piperidyl; morpholinyl and piperazinyl optionally substituted by one or more identical or different radicals selected from the oxo, alkyl and phenyl radicals themselves optionally substituted by one or more identical or different radicals selected from the halogen atoms and the hydroxyl, alkyl, alkoxy and hydroxyalkoxy radicals.

More particularly R6 and R7 can form, with the nitrogen atom to which they are bound, a morpholinyl or piperazinyl radical optionally substituted by one or more identical or different radicals selected from the oxo, alkyl and phenyl radicals, themselves optionally substituted by one or more identical or different radicals selected from the halogen atoms and the hydroxyl, alkyl, alkoxy and hydroxyalkoxy radicals.

The present invention thus relates to the products of formula (I) as defined above in which R1, R2, R3 and R5 have the meanings stated above, and R4 is selected from the hydrogen atom and the chlorine and fluorine atoms, said products of formula (I) being in all possible isomeric forms: racemic, enantiomeric and diastereoisomeric, as well as the addition salts with organic and inorganic acids or with organic and inorganic bases of said products of formula (I).

The present invention thus relates to the products of formula (I) as defined above in which R1, R2, R3 and R4 have the meanings stated above, and R5 represents hydrogen and fluorine, said products of formula (I) being in all possible isomeric forms: racemic, enantiomeric and diastereoisomeric, as well as the addition salts with organic and inorganic acids or with organic and inorganic bases of said products of formula (I).

The present invention thus relates to the products of formula (I) as defined above corresponding to formula (Ib):

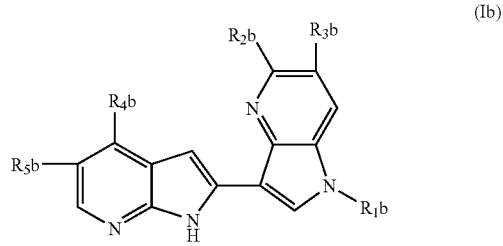

(Ib)

in which:

R1b represents alkyl containing 1 to 2 carbon atoms and optionally substituted by a morpholino and piperazinyl radical, itself optionally substituted by an alkyl radical, R2b and R3b, identical or different, represent alkoxy (notably OCH3)

R4b represents the hydrogen atom, halogen atoms and the CH2NR6R7 radicals, with R6 and R7 as defined above, R5b represents hydrogen and fluorine, said products of formula (Ib) being in all possible isomeric forms: racemic, enantiomeric and diastereoisomeric, as well as the addition salts with organic and inorganic acids or with organic and inorganic bases of said products of formula (Ib).

Among the preferred products of the invention, we may mention more particularly the products of formula (I) with the following names:

5,6-dimethoxy-1-methyl-3-(1H-pyrrolo[2,3-b]pyridin-2-yl)-1H-pyrrolo[3,2-b]pyridine, (16)

5,6-dimethoxy-1-(2-morpholin-4-yl-ethyl)3-(1H-pyrrolo[2,3-b]pyridin-2-yl)-1H-pyrrolo[3,2-b]pyridine, product 20

5,6-dimethoxy-1-[2-(4-methyl-piperazin-1-yl)ethyl]-3-(1H-pyrrolo[2,3-b]pyridin-2-yl)-1H-pyrrolo[3,2-b]pyridine, (22)

3-(4-chloro-1H-pyrrolo[2,3-b]pyridin-2-yl)-5,6-dimethoxy-1-methyl-1H-pyrrolo[3,2-b]pyridine, (30)

3-(4-chloro-1H-pyrrolo[2,3-b]pyridin-2-yl)-5,6-dimethoxy-1-(2-morpholin-4-yl-ethyl)-1H-pyrrolo[3,2-b]-pyridine, (34)

3-(4-chloro-1H-pyrrolo[2,3-b]pyridin-2-yl)-5,6-dimethoxy-1-[2-(4-methylpiperazin-1-yl)ethyl]-1H-pyrrolo[3,2-b]pyridine, (36)

3-(5-fluoro-1H-pyrrolo[2,3-b]pyridin-2-yl)-5,6-dimethoxy-1-(2-morpholin-4-yl-ethyl)-1H-pyrrolo[3,2-b]pyridine 3-(4-chloro-5-fluoro-1H-pyrrolo[2,3-b]pyridin-2-yl)-5,6-dimethoxy-1-(2-morpholin-4-yl-ethyl)-1H-pyrrolo[3,2-b]pyridine said products of formula (I) being in all possible isomeric forms: racemic, enantiomeric and diastereoisomeric, as well as the addition salts with organic and inorganic acids or with organic and inorganic bases of said products of formula (I).

Among the preferred products of the invention, mention may be made particularly of the products of formula (I) with the following names:

3-(4-chloro-5-fluoro-1H-pyrrolo[2,3-b]pyridin-2-yl)-5,6-dimethoxy-1-[2-(4-methylpiperazin-1-yl)ethyl]-1H-pyrrolo[3,2-b]pyridine 3-[4-chloro-5-fluoro-1H-pyrrolo[2,3-b]pyridin-2-yl]-5,6-dimethoxy -1-(3-piperidin-1-ylpropyl)-1H-pyrrolo[3,2-b]pyridine 1-{3-[3-(4-chloro-5-fluoro-1H-pyrrolo[2,3-b]pyridin-2-yl)-5,6-dimethoxypyrrolo[3,2-b]pyridin-1-yl] propyl}piperidin-4-ol -C-(1-{2-[3-(4-chloro-1H-pyrrolo[2,3-b]pyridin-2-yl)-5,6-dimethoxypyrrolo[3,2-b] pyridin-1-yl]ethyl}piperidin-4-yl)methylamine 2-[3-(4-chloro-1H-pyrrolo[2,3-b]pyridin-2-yl)-5,6-dimethoxypyrrolo[3,2-b]pyridin-1-yl]-1-(4-methylpiperazin-1-yl)ethanone {3-[3-(4-chloro-1H-pyrrolo[2,3-b]pyridin-2-yl)-5,6-dimethoxypyrrolo[3,2-b]pyridin-1-yl] propyl}diethylamine 3-(4-chloro-1H-pyrrolo[2,3-b]pyridin-2-yl)-5,6-dimethoxy-1-[3-(4-methyl-perhydro-1,4-diazepin-1-yl)propyl]-1H-pyrrolo[3,2-b]pyridine 2-(5,6-dimethoxy-1-methyl-1H-pyrrolo[3,2-b]pyridin-3-yl)-1H-pyrrolo[2,3-b]pyridine-4-carbonitrile Example 32

2-[3-(4-chloro-1H-pyrrolo[2,3-b]pyridin-2-yl)-5,6-dimethoxypyrrolo[3,2-b]pyridin-1-yl]-N-methoxy-N-methylacetamide

[2-(5,6-dimethoxy-1-methyl-1H-pyrrolo[3,2-b]pyridin-3-yl)-1H-pyrrolo[2,3-b]pyridin-4-ylmethyl]-(4-morpholin-4-ylphenyl)amine

[2-(5,6-dimethoxy-1-methyl-1H-pyrrolo[3,2-b]pyridin-3-yl)-1H-pyrrolo[2,3-b]pyridin-4-carbaldehyde oxime 4-{[2-(5,6-dimethoxy-1-methyl-1H-pyrrolo[3,2-b]pyridin-3-yl)-1H-pyrrolo[2,3-b]pyridin-4-ylmethyl]amino}phenol said products of formula (I) being in all possible isomeric forms: racemic, enantiomeric and diastereoisomeric, as well as the addition salts with organic and inorganic acids or with organic and inorganic bases of said products of formula (I).

The present invention also relates to a method of preparation of the products of formula (I) such as described above as follows:

the 1H-pyrrolo[2,3-b]pyridines of general formula A according to the present invention:

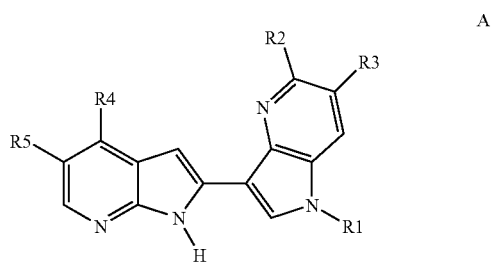

A in which R1, R2, R3, R4 and R5 are defined as before and can be prepared according to the schemes hereunder.

The 1H-pyrrolo[2,3-b]pyridines of general formula A can be obtained by deprotection of the 1H-pyrrolo[2,3-b]pyridines of general formula B possessing a protecting group in position 1. The protecting group can be any group known by a person skilled in the art such as a tosyl, an SEM, a BOC. More particularly, the 1H-pyrrolo[2,3-b]pyridines of general formula 1 can be obtained by deprotection of the derivatives of general formula 2 in classical conditions described by Greene and Wuts in Protective Groups in Organic Synthesis, 3$^{rd}$ edition, Wiley-Interscience, 1999.

In the case where the protecting group is a p-toluene sulfonyl group, N-deprotection of the derivatives of general formula 2 is carried out for example by heating in the presence of a base of sodium hydroxide or of potassium hydroxide in a solvent such as toluene, methanol or ethanol or alternatively for example in the presence of tetrabutylammonium fluoride in a solvent such as tetrahydrofuran at a temperature between 20° C. and the reflux temperature of the solvent.

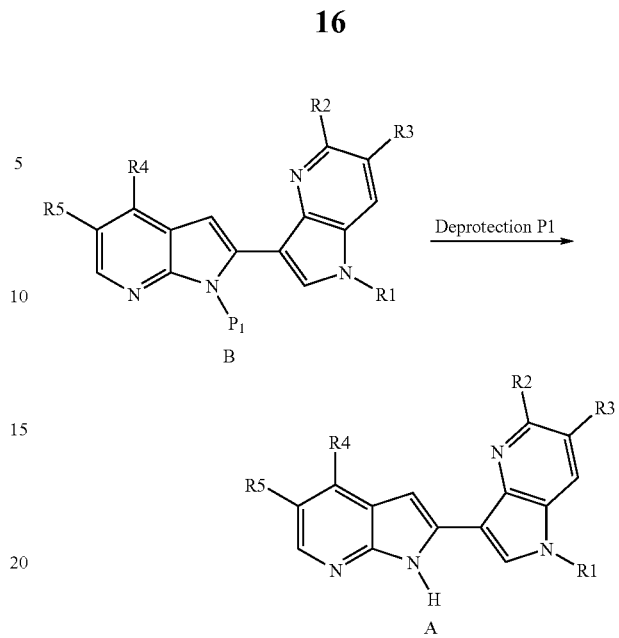

The 1H-pyrrolo[2,3-b]pyridines of general formula B can be obtained by deprotection of the P2 group followed by alkylation by chains of type R1 or their precursors. The protecting group can be any group known by a person skilled in the art such as an SEM or a BOC. The deprotection of the derivatives of general formula B will be carried out in classical conditions described by Greene and Wuts in Protective Groups in Organic Synthesis, 3rd edition, Wiley-Interscience, 1999. More particularly, in the case when the protecting group is to be a BOC, deprotection will be carried out in trifluoroacetic acid or in the presence of triethylsilyl iodide in dichloromethane or trifluoroacetic acid.

The alkylations can be carried out by treatment with an alkyl halide such as methyl iodide or a bromochloroalkane such as bromochloroethane, bromochloropropane or bromochlorobutane in the presence of a strong base such as for example potassium hydroxide, sodium methoxide, potassium carbonate or sodium hydride in a solvent such as dimethylformamide or methanol at a temperature between 20° and 60° C. In the case when the electrophilic reactant is to be a bromochloroalkane, the chlorine remaining on the molecule can be substituted by an iodo then followed by various nucleophilic amines such as dialkylamines such as dimethylamine, diethylamine, or morpholine, piperidine, pyrrolidine, homomorpholine, proline and its derivatives.

More particularly, the 1H-pyrrolo[2,3-b]pyridine of general formula B can be obtained by alkylation of the derivatives of general formula C with an alkyl halide optionally substituted in the end position by:

a cyclic or acyclic amine, optionally substituted,
an alkyl carboxylate
an alkyl ether
a halogen as for example in the conditions described by Oelgen D. et al. (Pharmazie, 57(4), 238, 2002), in the presence of a base such as sodium hydride, in a solvent such as dimethylformamide at a temperature between 20° and the reflux temperature of the solvent.

In the case of the alkyl halides optionally substituted in the end position by a cyclic or acyclic, optionally substituted amine, the conditions described by D. Bogdal et al. (Synthetic Communication, 30 (18), 3341-3352, 2000) in dichloroethane in the presence of bases such as potassium hydroxide, potassium carbonate, a quaternary ammonium such as tetrabutylammonium bromide at a temperature close to 20° C., can optionally be used.

In the case of the alkyl halides optionally substituted in the end position by an alkyl carboxylate, the conditions described by Z. Kaluza et al. (Synlett 1996, (9), 895-896) in the presence of bases such as potassium hydroxide, potassium carbonate, a quaternary ammonium such as tetrabutylammonium bromide at a temperature in the region of 20° C., may optionally be used.

In the case of the alkyl halides optionally substituted in the end position by an alkyl carboxylate, the ester may be saponified to an acid in a solvent such as methanol in the presence of a base such as potassium hydroxide, at a temperature in the region of 20° C.

The acid thus obtained may then be coupled with amines HNR7R8, for instance under the conditions described by S. Vendeville, S. et al. (Bioorg Med Chem Lett 1999, 9 (3), 437-442) in dimethylformamide in the presence of a base such as diisopropylethylamine and in the presence of a coupling agent such as 1-hydroxybenzotriazole, at a temperature in the region of 20° C.

In the case of the alkyl halides optionally substituted in the end position by an alkyl ether, the conditions described by E. Betakis et al. (Synthesis; 1988; 820-823), in the presence of bases such as potassium hydroxide, potassium carbonate or a quaternary ammonium such as tetrabutylammonium bromide at a temperature in the region of 20° C., may optionally be used.

In the case of alkyl halides optionally substituted in the end position by a chlorine atom, the chlorine can be displaced by an iodine with sodium or potassium iodide, as for example in the conditions described by Allen C. F. H. et al. (J. Org Chem, 14, 754, 1949), in a solvent such as methyl ethyl ketone at a temperature between 20° and the reflux temperature of the solvent. The iodides obtained can then be displaced by amines HNR6R7, as for example in the conditions described by Pujol M. D. et al. (Eur. J. Med. Chem., 31(11), 889, 1996), in the presence of a base such as potassium carbonate, in a solvent such as acetonitrile, dimethylformamide or alternatively methyl ethyl ketone at a temperature between 20° and the reflux temperature of the solvent.

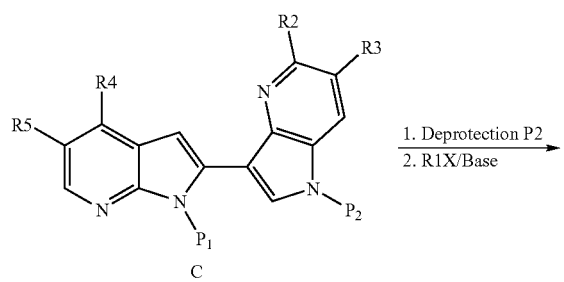

C

1. Deprotection P2
2. R1X/Base

-continued

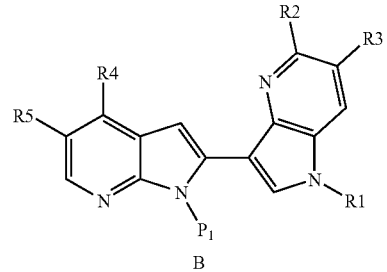

B

The 1H-pyrrolo[2,3-b]pyridines of general formula C can be obtained by coupling between the 1H-pyrrolo[2,3-b]pyridines stannylated in position 2 of general formula D and the 4-azaindoles brominated in position 3 of general formula E. These couplings will be carried out in conditions such as described by Stille (ref Stille coupling) in the presence of catalysts such as palladium tetrakis or PdCl2(PPH3)2 in a solvent such as toluene or DMF.

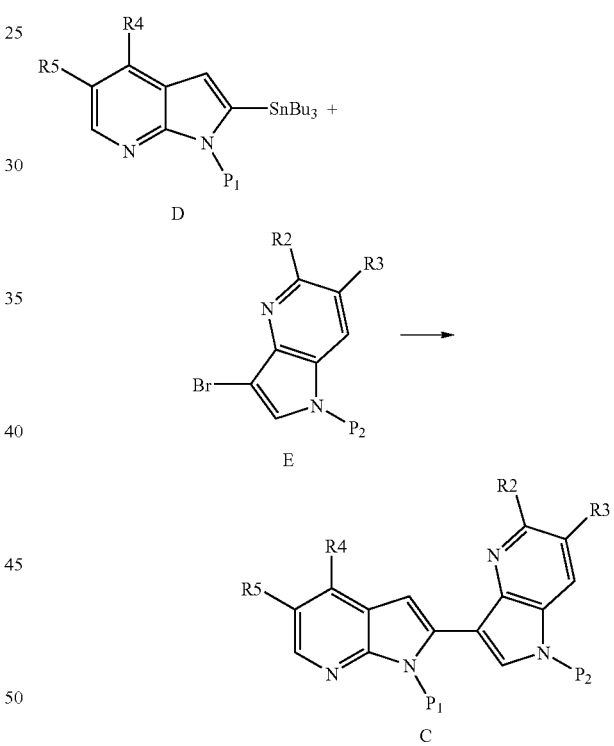

The 1H-pyrrolo[2,3-b]pyridines stannylated in position 2 of general formula D can be obtained starting from the 1H-pyrrolo[2,3-b]pyridines of general formula F after reaction of protection of the nitrogen at 1 by a group that is able to control a reaction of orthometalation at position 2 and trapping of the anion in position 2 by an electrophilic derivative of tin. The bases used will be strong bases such as alkyl, sec-alkyl and tert-alkyl lithium, or sodium amide. The derivatives of tin will be either tributyltin chloride, or hexamethyl distannane.

More particularly, the 1H-pyrrolo[2,3-b]pyridines of general formula G can be obtained in the conditions described in patent WO 03/000688 A1 by protection of the nitrogen atom of the derivatives of general formula F by a group such as for example p-toluene sulfonyl or benzene sulfonyl by treatment with the corresponding sulfonyl chlorides in the presence of a strong base such as sodium hydroxide and of a quaternary ammonium salt such as tetrabutylammonium hydrogen sulfate in a mixture of water and a solvent such as toluene at a temperature close to 20° C.

The 1H-pyrrolo[2,3-b]pyridines of general formula D can be obtained as in the conditions described in the patent cited above, by treatment of the derivatives of general formula G with a strong base such as n-butyllithium or tert-butyllithium in an ethereal solvent such as tetrahydrofuran followed by the addition of a derivative of tin in solution in a solvent such as tetrahydrofuran, at a temperature close to −78° C. The derivatives of tin can be tributyultin chloride or hexamethylstannane.

More particularly, the 1H-pyrrolo[2,3-b]pyridine 7-oxides of general formula L can be obtained by treatment of the derivatives of general formula K with 3-chloro-peroxybenzoic acid in an ethereal solvent such as 1,2-dimethoxyethane at a temperature close to 20° C. in the conditions described in patent WO 03/000688 A1;

the 1H-pyrrolo[2,3-b]pyridines of general formula F with $R_4$=Cl can be obtained starting from the 1H-pyrrolo[2,3-b] pyridine 7-oxides of general formula L by treatment with phosphorus oxychloride at a temperature between 20° C. and 50° C.

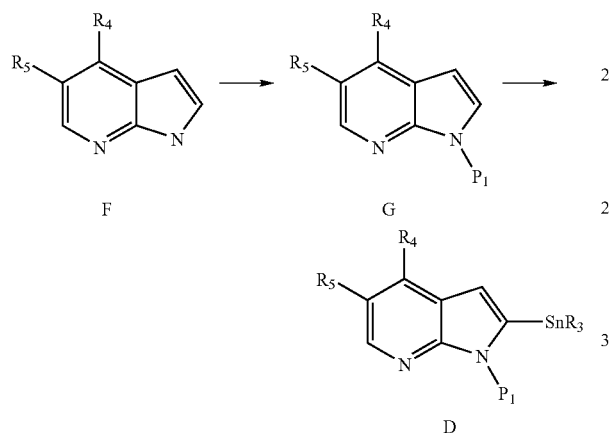

The 1H-pyrrolo[2,3-b]pyridines of general formula F can be obtained starting from 2-aminopyridines of general formula H by halogenation in position 3 followed by Sonogashira coupling with a trimethylsilylacetylene. Alternatively, and in the case where R4 will be a chlorine atom, they can be obtained starting from commercial 1H-pyrrolo[2,3-b]pyridine K by oxidation followed by rearrangement in the presence of a halogenating agent.

More particularly, treatment of the 2-aminopyridines of general formula H with N-iodosuccinimide or N-bromosuccinimide in a solvent such as acetic acid at a temperature between 20° C. and 80° C. as for example in the conditions described by Fuss A. and Koch V. (Synthesis, 1990, 8, 681-5) leads to the 3-halogeno-2-aminopyridines of general formula I.

More particularly, the 3-trimethylsilanylethynyl-pyridin-2-yl-amines of general formula J can be obtained by coupling of Sonogashira type with ethynyl-trimethylsilane as for example in the conditions described by Knochel P. et al. (Tetrahedron, 2003, 59, 1571-1587) starting from 3-halogeno-2-aminopyridines of general formula H in the presence of catalysts such as [1,1'-bis(diphenylphosphino)ferrocene] palladium(II) chloride or bis(triphenylphosphine)-palladium (II) chloride, copper iodide, a base such as triethylamine and optionally lithium chloride in a solvent such as dimethylformamide at a temperature between 20° C. and 120° C.

More particularly, the 1H-pyrrolo[2,3-b]pyridines of general formula F can be obtained by cyclization of the derivatives of general formula J in the presence of a strong base such as potassium tert-butylate or potassium hydride, in a solvent such as 1-methyl-2-pyrrolidinone at a temperature between 20° C. and 120° C.

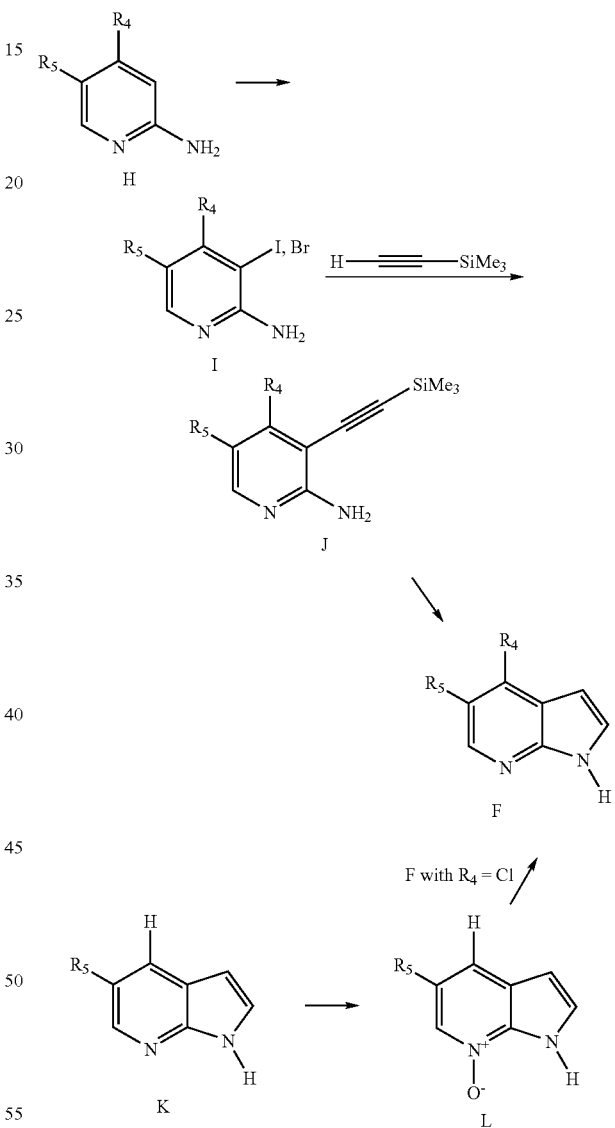

The 4-azaindoles of general formula E can be obtained starting from the derivatives of general formula M after halogenation in position 3 to give 4-azaindoles of general formula N, followed by protection of the nitrogen atom in position 1 by a protecting group such as a BOC, an SEM, an acetyl.

More particularly, 4-azaindoles of general formula M can be halogenated by electrophilic halogenating agents such as bromine, NBS, NIS or iodine in a solvent such as DMF or dichloroethane. The resulting 4-azaindoles N can then be protected by various protecting groups such as described in Greene and Wuts in Protective Groups in Organic Synthesis, 3rd edition, Wiley-Interscience.

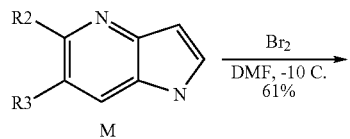

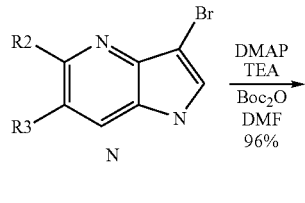

The 4-azaindoles of general formula M can be obtained starting from the 2-iodopyridines of general formula O after a reaction of formylation followed by a reaction of nitration and finally reaction of the resulting 2-formylpyridines P with nitromethane.

We may mention, as references relating to this Henry reaction, the following articles: Rosini, G.; Ballini, R.; Sorrenti, P. *Synthesis* 1983, 1014-1016 as well as: Henry, L. *C. R. Acad. Sci. Paris* 1895, 120, 1265) and also: Novellino, L.; d'Ischia, M.; Prota, G. *Synthesis* 1999, 793-796. More particularly, the -iodopyridines of general formula O can be treated with a strong base such as nBuLi, SecBuLi or tBuLi followed by a formulating reagent such as DMF at a temperature between −78° C. and room temperature to give the 4-formylpyridines of general formula P.

More particularly, the 2-formylpyridines of general formula P can then be nitrated in conventional electrophilic nitration conditions known by a person skilled in the art, such as nitric acid or copper nitrate in sulfuric acid, or acetic anhydride. In this last case, the aldehyde can be obtained as its diacetylacetal R.

More particularly, the diacetylacetal R can be reacted with nitromethane in the presence of a base such as sodium methoxide or ethoxide and will then be cyclized in acidic and/or basic conditions such as sodium acetate in acetic anhydride or paratoluene sulfonic acid in the presence of iron catalysis. The reference for the Borchardt modification of cyclization of the dinitrostyrenes is as follows: Sinhababu, A. K.; Borchardt, R. T. *J. Org. Chem.* 1983, 48, 3347-3349.

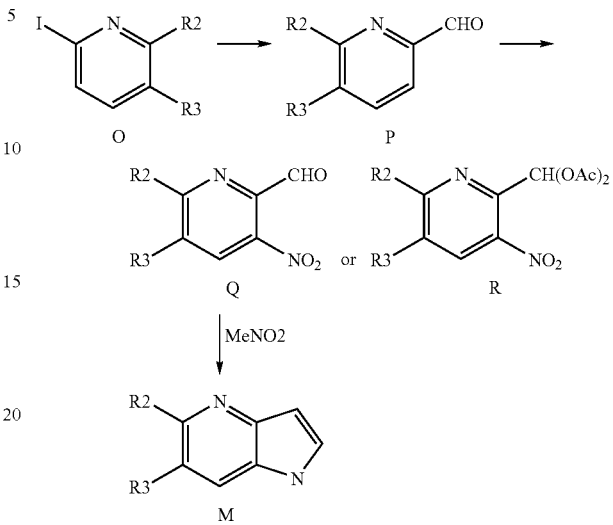

The 2-iodopyridines of general formula O can be obtained starting from pyridines of general formula S in conventional conditions of iodination in the presence of iodine and of a base such as potassium carbonate at room temperature.

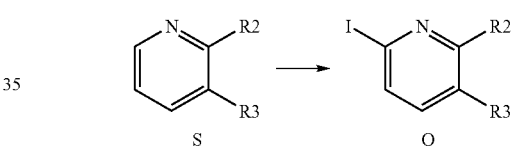

The products of formula (I) of the present invention as described above can be prepared as stated above and notably as stated in the schemes shown below: these schemes thus describe stages in the synthesis of the products of formula (I) of the present invention and form part of the present invention.

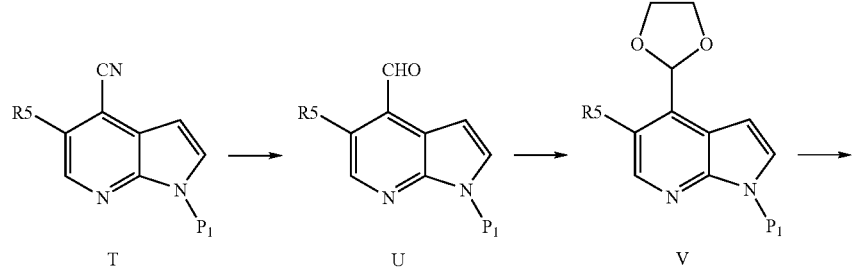

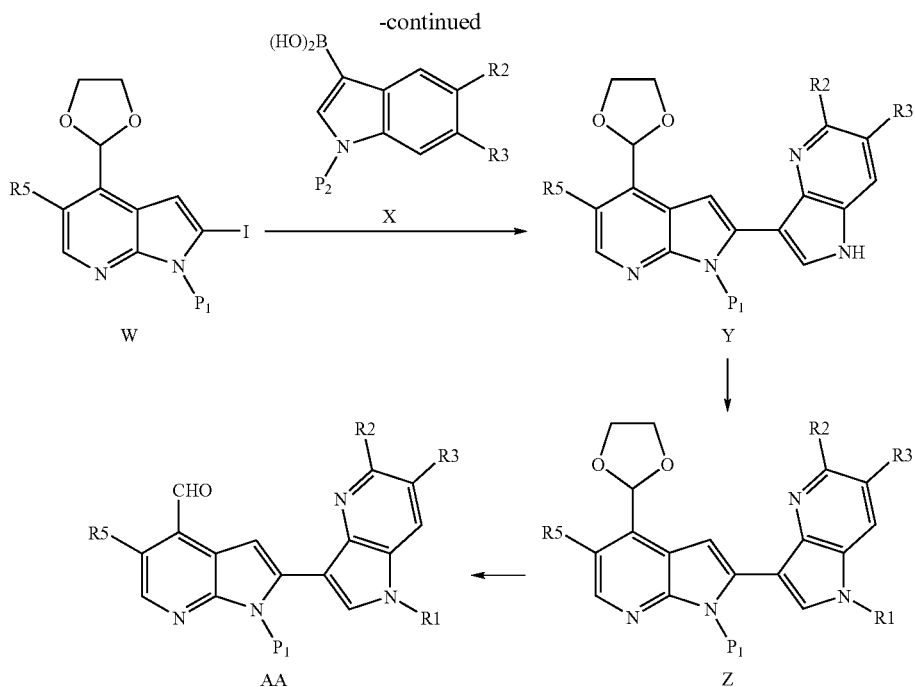

The 4-carbaldehyde-1H-pyrrolo[2,3-b]pyridines of general formula U may be obtained by treating the 4-cyano-1H-pyrrolo[2,3-b]pyridines of general formula T with a reducing agent such as diisobutylaluminum hydride (DIBAH), in an aprotic solvent such as toluene, at a temperature of between −30° C. and 20° C., for instance under the conditions described by Anderson, B. A. et al. (J. Org. Chem., 1997, 62(25), 8634-8639).

More particularly, the 4-(1,3-dioxolane)-1H-pyrrolo[2,3-b]pyridines of general formula V may be obtained by reacting the derivatives of general formula U with ethylene glycol in a solvent such as toluene, in the presence of an acid catalyst such as para-toluenesulfonic acid, at a temperature of between 80° C. and 120° C., for instance under the conditions described by Pasto M. et al. (Tetrahedron: Asymmetry, 1995, 6(9), 2329-2342).

The 4-(1,3-dioxolane)-2-iodo-1H-pyrrolo[2,3-b]pyridines of general formula W may be obtained as under the conditions described in patent WO 03/000688 A1, by treatment of the derivatives of general formula V with a strong base such as n-butyllithium or tert-butyllithium in an ether solvent such as tetrahydrofuran, followed by the addition of iodine dissolved in a solvent such as tetrahydrofuran, at a temperature in the region of −78° C.

More particularly, the 1H-pyrrolo[2,3-b]pyridines of general formula Y may be obtained by a coupling of Suzuki type between the derivatives of general formula X and the derivatives of general formula W, for instance under the conditions described in patent WO 03/000688 A1 in the presence of a catalyst such as tetrakis(triphenylphosphine)palladium, a base such as sodium hydrogencarbonate in aqueous solution, in a solvent such as dimethylformamide at a temperature of between 20° C. and the reflux temperature of the solvent.

More particularly, the 1H-pyrrolo[2,3-b]pyridines of general formula Z may be obtained from the derivatives of general formula Y as described above for the derivatives of general formula B.

More particularly, the 1H-pyrrolo[2,3-b]pyridines of general formula AA may be obtained by treating the derivatives of general formula Z in the presence of an acid such as hydrochloric acid, in a solvent such as tetrahydrofuran at a temperature of between 20° C. and 60° C., for instance under the conditions described by Ishimaru K. et al. (Heterocycles, 2001, 55(8), 1591-1597).

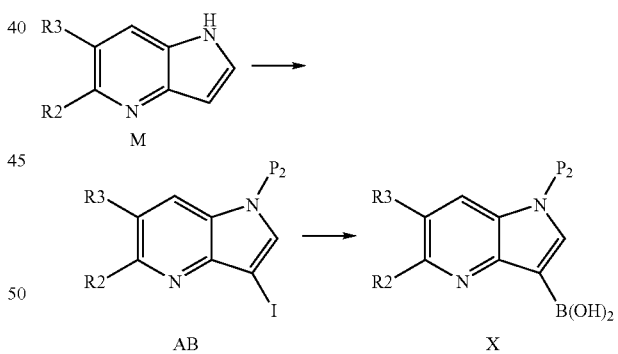

More particularly, the 1H-indoles of general formula AB may be obtained from the derivatives of general formula M as under the conditions described in patent WO 03/000688 A1 by treatment with iodine in the presence of a strong base, for instance potassium hydroxide and an organic base, for instance 4-(dimethylamino)pyridine, followed by the addition of di-tert-butyl dicarbonate in a solvent such as dimethylformamide at a temperature of between 20° C. and 60° C.

More particularly, the 1H-indoles of general formula X may be obtained from the derivatives of general formula AB as under the conditions described in patent WO 03/000688 A1 by treatment with a strong base, for instance n-butyllithium and a boronic ester, for instance tributyl borate in an ether solvent such as tetrahydrofuran at a temperature of between −100° C. and 20° C.

the solvent, for instance under the conditions described by Kaneko, T. et al. (Chem. Pharm. Bull., 2002, 50(7), 922-929);

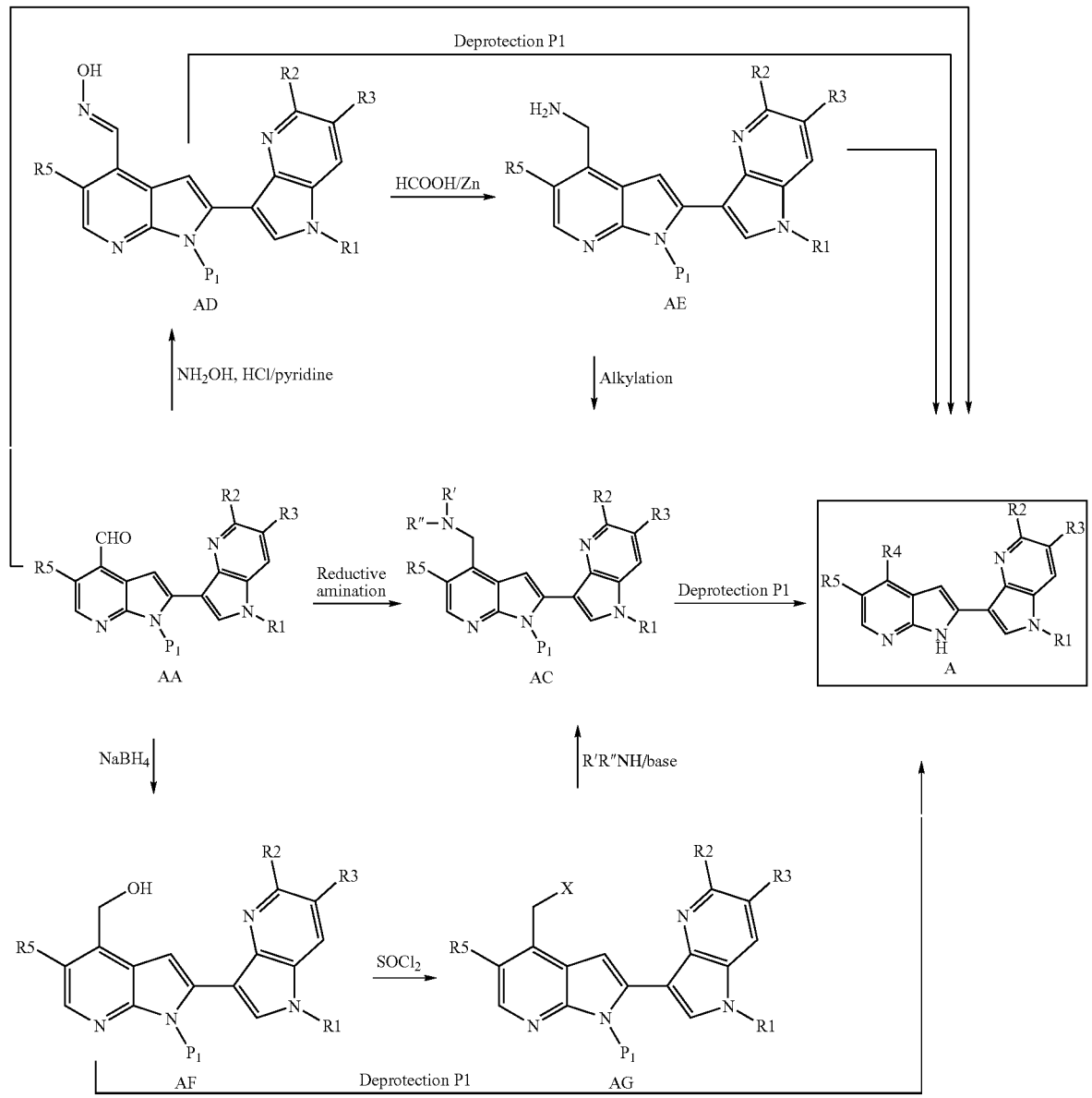

More particularly, the 1H-pyrrolo[2,3-b]pyridines of general formula AC may be obtained by treating the derivatives of general formula AA with an amine, in the presence of a hydride such as sodium borohydride and a dehydrating agent such as magnesium sulfate, in a solvent such as methanol or ethanol at a temperature in the region of 20° C., for instance under the conditions described by Patra, P. K. et al. (Eur. J. Org. Chem., 2001, 22, 4195-4206).

These 1H-pyrrolo[2,3-b]pyridines of general formula AC may also be obtained:
either by treating the derivatives of general formula AE with a halide or a mesylate, in the presence of a base such as sodium carbonate, in a solvent such as acetonitrile at a temperature of between 20° C. and the boiling point of the solvent, for instance under the conditions described above.

or by treating the derivatives of general formula AG with an amine, in the presence of a base such as sodium carbonate, in a solvent such as acetonitrile at a temperature of between 20° C. and the boiling point of the solvent, for instance under the conditions described above.

The 1H-pyrrolo[2,3-b]pyridines of general formula AD may be obtained from the 1H-pyrrolo[2,3-b]pyridines of general formula AA by treatment with hydroxylamine hydrochloride, in a solvent such as pyridine, at a temperature of between 20° C. and 50° C., for instance under the conditions described by Schroeder, M. C. et al. (J. Heterocyclic Chem., 1992, 29(6), 1481-1498).

More particularly, the 4-aminomethyl-1H-pyrrolo[2,3-b] pyridines of general formula AE may be obtained by reducing the oxime AD with a metal such as zinc in the presence of an acid such as acetic acid or formic acid, in a solvent such as water and/or ethanol and at a temperature in the region of 20° C., for instance under the conditions described by Prasitpan, N. et al. (Synth. Commun., 1990, 20(22), 3459-3466).

The 1H-pyrrolo[2,3-b]pyridine-4-methanol compounds of general formula AF may be obtained by reduction of the derivatives of general formula AA with a hydride such as sodium borohydride, in an ether solvent such as tetrahydrofuran, at a temperature in the region of 20° C., for instance under the conditions described by Wang, E. C. et al. (Heterocycles, 2002, 57(11), 2021-2033).

More particularly, the 1H-pyrrolo[2,3-b]pyridines of general formula AG, with X=Cl, may be obtained from the 1H-pyrrolo[2,3-b]pyridine-4-methanol compounds of general formula AF, as under the conditions described by Fucase K. et al. (Tetrahedron Lett., 1991, 32(32), 4019-4022) by treatment with thionyl chloride in the presence of DMF in a solvent such as dichloromethane at a temperature of between 0° C. and 20° C.

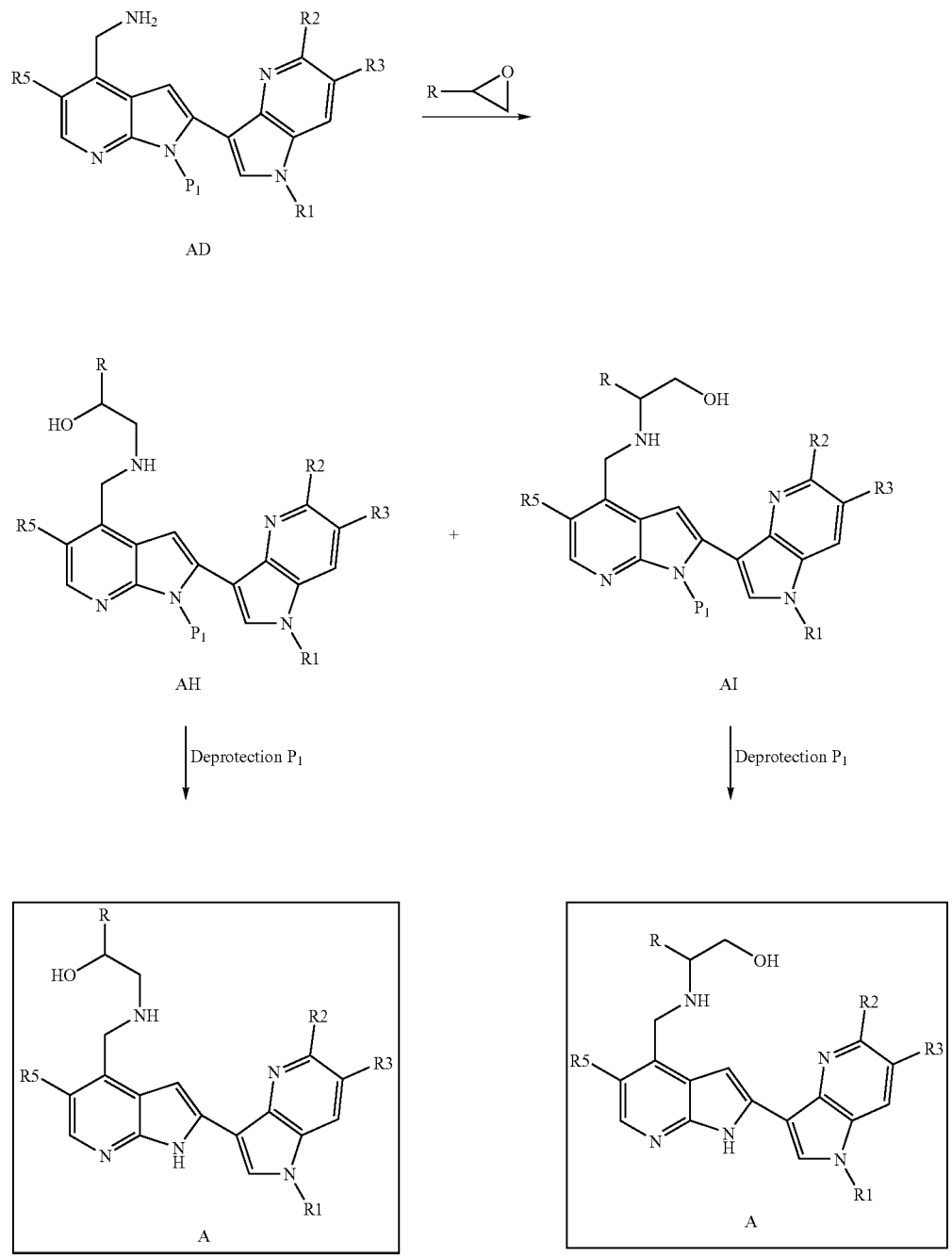

More particularly, the 1H-pyrrolo[2,3-b]pyridines of general formulae AH and AI may be obtained from the 1H-pyrrolo[2,3-b]pyridine-4-methylamines of general formula AD, as under the conditions described by Batra S. et al. (Indian J. Chem. Sect. B. 1996, 35(1), 36-39) by treatment with an epoxide in a solvent such as ethanol at a temperature of between 20° C. and the boiling point of the solvent.

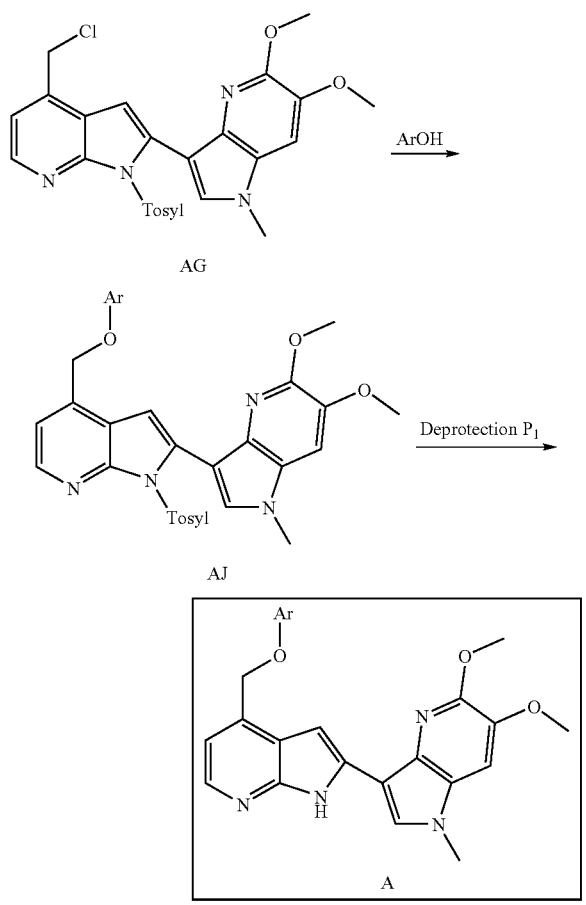

More particularly, the 1H-pyrrolo[2,3-b]pyridines of general formula AJ may be obtained from the 4-chloromethyl-1H-pyrrolo[2,3-b]pyridines of general formula AG, as under the conditions described by Imbos R. et al. (J. Am. Chem. Soc. 2002, 124(2), 184-185) by treatment with a phenol in the presence of a base such as potassium carbonate in a solvent such as acetonitrile at a temperature of between 0° C. and the boiling point of the solvent.

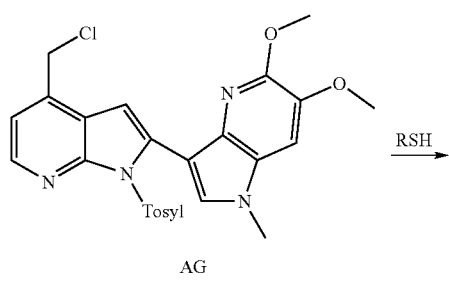

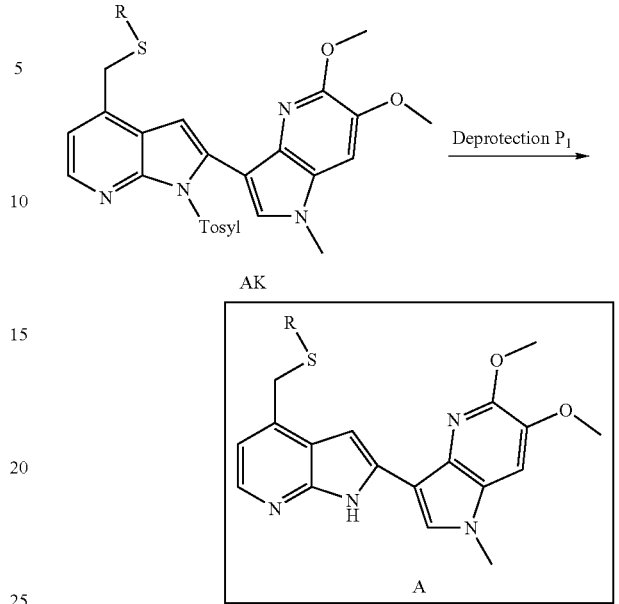

More particularly, the 1H-pyrrolo[2,3-b]pyridines of general formula AK may be obtained from the 4-chloromethyl-1H-pyrrolo[2,3-b]pyridines of general formula AG, as under the conditions described by Terashima K. et al. (Chem. Pharm. Bull, 1995, 43(11), 2021-2023) by treatment with a thiol under phase-transfer conditions, in the presence of a quaternary ammonium such as methyltrioctylammonium bromide and a base such as sodium hydroxide in a solvent such as dichloromethane and water at a temperature of between 0° C. and 20° C.

It may be noted that in the reactions of preparation of the products of formula (I) according to the present invention and notably in the reactions shown in the schemes given below, the intermediates or the products of formula (I) can if necessary be in protected form, any reactive functions being optionally protected by protecting groups.

The intermediates or the products of formula (I), in protected or unprotected form, can be subjected, if desired and if necessary, to obtain products of formula (I) or other products of formula (I) to one or more of the following transformation reactions, in any order:

a) a reaction of esterification of an acid function,
b) a reaction of saponification of ester function to acid function,
c) a reaction of oxidation of an alkylthio group to the corresponding sulfoxide or sulfone,
d) a reaction of transformation of a ketone function to an oxime function,
e) a reaction of reduction of the free or esterified carboxy function to an alcohol function,
f) a reaction of transformation of an alkoxy function to a hydroxyl function, or moreover of a hydroxyl function to an alkoxy function,
g) a reaction of oxidation of an alcohol function to an aldehyde, acid or ketone function,
h) a reaction of transformation of a nitrile radical to a tetrazolyl,
i) a reaction of reduction of nitrated compounds to amino compounds, j) a reaction of elimination of the protecting groups that the protected reactive functions may carry, k) a reaction of salification by an organic or inorganic acid or by a base to obtain the corresponding salt, l) a reaction of resolution of the racemic forms to resolved products, said products of formula (I) thus obtained being in all possible isomeric forms: racemic, enantiomeric and diastereoisomeric.

It may be noted that said reactions of transformation of substituents to other substituents can also be carried out on the starting products as well as on the intermediates as defined above before continuing the synthesis according to the reactions indicated in the method described above.

The products of formula (I) according to the present invention might also be prepared by the application or the adaptation of known methods and notably the methods described in the literature such as for example those described by R. C. Larock in: Comprehensive Organic Transformations, VCH publishers, 1989.

To prepare the products of formula (I), it may therefore be necessary to protect reactive functional groups such as for example hydroxy, amino, imino, thio or carboxy groups, when the latter are desired in the end product but when their participation is undesirable in the reactions of synthesis of the products of formula (I). In particular it is possible to use conventional protecting groups in accordance with the usual standard practices of protection or deprotection such as those described for example by T. W. Greene and P. G. M. Wuts in "Protective Groups in Organic Chemistry" John Wiley and Sons, 1991 or 3rd edition, Wiley-Interscience, 1999.

It may be noted that in the case when the protecting group is a p-toluene sulfonyl group, N-deprotection of the derivatives is effected as for example in the presence of potassium hydroxide in a solvent such as methanol at a temperature between 20° C. and the reflux temperature of the solvent.

Thus, the various reactive functions that may be borne by certain compounds of the reactions defined above can, if necessary, be protected. This is the case for example of the hydroxyl, acyl, or free carboxy radicals or moreover amino and monoalkylamino radicals which can be protected by the appropriate protecting groups.

The following, non-exhaustive list of examples of protection of reactive functions may be mentioned:

hydroxyl groups can be protected for example by alkyl radicals such as tert-butyl, trimethyl-silyl, tert-butyldimethylsilyl, methoxymethyl, tetrahydro-pyranyl, benzyl or acetyl, amino groups can be protected for example by acetyl, trityl, benzyl, tert-butoxycarbonyl, benzyloxycarbonyl, phthalimido radicals or by other radicals known in peptide chemistry, acyl groups such as the formyl group can be protected for example as ketals or of thioketals, cyclic or noncyclic, such as dimethyl or diethylketal or ethylene dioxyketal, or diethylthioketal or ethylenedithioketal, acid functions of the products described above can, if desired, be amidated by a primary or secondary amine for example in methylene chloride in the presence, for example, of 1-ethyl-3-(dimethylaminopropyl) carbodiimide hydrochloride at room temperature:

acid functions can be protected for example as esters formed with readily cleavable esters such as the benzyl or terbutyl esters or esters known in peptide chemistry.

These reactions a) to k) stated above can be carried out, for example, as stated hereafter.

a) The products described above can, if desired, be the object, on any carboxy functions, of reactions of esterification which can be carried out according to the usual methods known by a person skilled in the art.

b) The optional transformations of ester functions to acid function of the products described above can, if desired, be carried out under the usual conditions known by a person skilled in the art, notably by acid or alkaline hydrolysis for example with sodium hydroxide or potassium hydroxide in an alcoholic medium such as, for example, methanol or moreover with hydrochloric or sulfuric acid.

c) Any alkylthio groups of the products described above, in which the alkyl radical is optionally substituted by one or more halogen atoms, notably fluorine, can, if desired, be transformed to the corresponding sulfoxide or sulfone functions in the usual conditions known by a person skilled in the art such as for example with peracids such as for example peracetic acid or metachloroperbenzoic acid or moreover with ozone, oxone, sodium periodate in a solvent such as for example methylene chloride or dioxane at room temperature.

Production of the sulfoxide function can be promoted by an equimolar mixture of the product containing an alkylthio group and of the reagent such as notably a peracid.

Production of the sulfone function can be promoted by a mixture of the product containing an alkylthio group with an excess of the reagent such as notably a peracid.

d) The reaction of transformation of a ketone function to oxime can be carried out in the usual conditions known by a person skilled in the art, such as notably action in the presence of a hydroxylamine optionally O-substituted in an alcohol such as for example ethanol, at room temperature or with heating.

e) Any free or esterified carboxy functions of the products described above can, if desired, be reduced to alcohol function by the methods known by a person skilled in the art: any esterified carboxy functions can, if desired, be reduced to an alcohol function by the methods known by a person skilled in the art and notably with lithium and aluminum hydride in a solvent such as for example tetrahydrofuran or moreover dioxan or ethyl ether.

Any free carboxy functions of the products described above can, if desired, be reduced to alcohol function notably with boron hydride.

f) Any alkoxy functions, such as notably methoxy, of the products described above can, if desired, be converted to hydroxyl function in the usual conditions known by a person skilled in the art, for example with boron tribromide in a solvent such as for example methylene chloride, with pyridine hydrobromide or hydrochloride or moreover with hydrobromic or hydrochloric acid in water or trifluoroacetic acid under reflux.

g) Any alcoholic functions of the products described above can, if desired, be converted to aldehyde or acid function by oxidation in the usual conditions known by a person skilled in the art such as for example by the action of manganese oxide to obtain the aldehydes or of the Jones reagent for obtaining the acids.

h) Any nitrile functions of the products described above can, if desired, be converted to tetrazolyl in the usual conditions known by a person skilled in the art such as for example by cycloaddition of a metal azide such as for example sodium azide or a trialkyltin azide on the nitrile function as is stated in the method described in the article with the following reference:

J. Organometallic Chemistry., 33, 337 (1971) KOZIMA S. et al.

It may be noted that the reaction of conversion of a carbamate to urea and notably of a sulfonylcarbamate to sulfonylurea, can be carried out for example with reflux of a solvent such as for example toluene in the presence of the appropriate amine.

It is understood that the reactions described above can be carried out as stated or moreover, as required, according to other usual methods known by a person skilled in the art.

i) The elimination of protecting groups such as for example those stated above can be carried out in the usual conditions known by a person skilled in the art or as stated above or moreover as stated in the literature: notably by acid or basic hydrolysis carried out with an acid such as hydrochloric, benzene sulfonic or para-toluene sulfonic, formic or trifluoroacetic acid or moreover by catalytic hydrogenation or hydrogenation by a base such as potassium hydroxide, sodium hydroxide or tetrabutylammonium fluoride.

The phthalimido group can be eliminated by hydrazine.

A list of various protecting groups that can be used is given for example in patent FP 2 499 995.

j) The products described above can, if desired, be subjected to reactions of salification for example by an organic or inorganic acid or by an organic or inorganic base according to the usual methods known by a person skilled in the art.

k) Any optically active forms of the products described above can be prepared by resolution of the racemic forms according to the usual methods known by a person skilled in the art.

Possible reactive functions are the hydroxy or amino functions: the usual protecting groups are used for protecting these functions. We may mention for example the following protecting groups of the amino radical: tert-butyl, tert-amyl, trichloro-acetyl, chloroacetyl, benzhydryl, trityl, formyl, benzyloxycarbonyl, paratoluenesulfonyl, acetyl, benzenesulfonyl or benzoyl.

As protecting group of the hydroxy radical we may mention radicals such as formyl, benzyl, acetyl, chloroacetyl, tetrahydropyranyl, trimethylsilyl, tert-butyl dimethylsilyl.

It is understood that the above list is not limitative and that other protecting groups, known in peptide chemistry for example, can be used. A list of said protecting groups is given for example in French patent FP 2,499,995, the contents of which are incorporated here by reference.

Possible reactions of elimination of the protecting groups are carried out as stated in said patent FP 2,499,995. The preferred manner of elimination is acid hydrolysis using acids selected from hydrochloric, benzene sulfonic or paratoluene sulfonic, formic or trifluoroacetic acids. Hydrochloric acid is preferred.

Any reaction of hydrolysis of the >C=NH group to a ketone group is also carried out preferably by means of an acid such as aqueous hydrochloric acid for example under reflux.

The terbutyldimethylsilyl protecting group can be eliminated for example by means of hydrochloric acid.

Any esterification of an OH free radical is carried out under conventional conditions. We may use for example an acid or a functional derivative, for example an anhydride such as acetic anhydride in the presence of a base such as pyridine. Any esterification or salification of a COOH group is carried out under the conventional conditions known by a person skilled in the art.

Any amidation of a COOH radical is carried out under conventional conditions. It is possible to use a primary or secondary amine on a functional derivative of the acid, for example a symmetric or mixed anhydride.

The products covered by the present invention possess interesting pharmacological properties: notably, they have been found to possess protein kinase inhibiting properties.

Among these protein kinases, we may mention notably IGF1R.

Tests given below in the experimental part illustrate the inhibitory activity of the products of the present invention with respect to said protein kinases.

These properties therefore mean that the products of general formula (I) of the present invention can be used as medicinal products for the treatment of malignant tumors.

The products of formula (I) can also be used in the veterinary field.

The invention therefore relates to the application of the pharmaceutically acceptable products of general formula (I), as medicinal products.

The invention relates in particular to the application, as medicinal products, of the products of formula (I) described as examples in the experimental part and especially those with the following names:

5,6-dimethoxy-1-methyl-3-(1H-pyrrolo[2,3-b]pyridin-2-yl)-1H-pyrrolo[3,2-b]pyridine;

5,6-dimethoxy-1-(2-morpholin-4-yl-ethyl)3-(1H-pyrrolo[2,3-b]pyridin-2-yl)-1H-pyrrolo[3,2-b]pyridine;

5,6-dimethoxy-1-[2-(4-methyl-piperazin-1-yl)ethyl]-3-(1H-pyrrolo[2,3-b]pyridin-2-yl)-1H-pyrrolo[3,2-b]pyridine;

3-(4-chloro-1H-pyrrolo[2,3-b]pyridin-2-yl)-5,6-dimethoxy-1-methyl-1H-pyrrolo[3,2-b]pyridine;

3-(4-chloro-1H-pyrrolo[2,3-b]pyridin-2-yl)-5,6-dimethoxy-1-(2-morpholin-4-yl-ethyl)-1H-pyrrolo[3,2-b]pyridine;

3-(4-chloro-1H-pyrrolo[2,3-b]pyridin-2-yl)-5,6-dimethoxy-1-[2-(4-methylpiperazin-1-yl)ethyl]-1H-pyrrolo[3,2-b]pyridine;

3-(5-fluoro-1H-pyrrolo[2,3-b]pyridin-2-yl)-5,6-dimethoxy-1-(2-morpholin-4-yl-ethyl)-1H-pyrrolo[3,2-b]pyridine);

3-(4-chloro-5-fluoro-1H-pyrrolo[2,3-b]pyridin-2-yl)-5,6-dimethoxy-1-(2-morpholin-4-yl-ethyl)-1H-pyrrolo[3,2-b]pyridine;

as well as their prodrugs, said products of formula (I) being in all possible isomeric forms: racemic, enantiomeric and diastereoisomeric, as well as the pharmaceutically acceptable addition salts with organic and inorganic acids or with organic and inorganic bases of said products of formula (I).

A subject of the invention is especially the use, as medicaments, of the products of formula (I) with the following names:

3-(4-chloro-5-fluoro-1H-pyrrolo[2,3-b]pyridin-2-yl)-5,6-dimethoxy-1-[2-(4-methylpiperazin-1-yl)ethyl]-1H-pyrrolo[3,2-b]pyridine 3-[4-chloro-5-fluoro-1H-pyrrolo[2,3-b]pyridin-2-yl]-5,6-dimethoxy-1-(3-piperidin-1-ylpropyl)-1H-pyrrolo[3,2-b]pyridine 1-{3-[3-(4-chloro-5-fluoro-1H-pyrrolo[2,3-b]pyridin-2-yl)-5,6-dimethoxypyrrolo[3,2-b]pyridin-1-yl] propyl}piperidin-4-ol -C-(1-{2-[3-(4-chloro-1H-pyrrolo[2,3-b]pyridin-2-yl)-5,6-dimethoxypyrrolo[3,2-b]pyridin-1-yl]ethyl}piperidin-4-yl)methylamine 2-[3-(4-chloro-1H-pyrrolo[2,3-b]pyridin-2-yl)-5,6-dimethoxypyrrolo[3,2-b]pyridin-1-yl]-1-(4-methylpiperazin-1-yl)ethanone {3-[3-(4-chloro-1H-pyrrolo[2,3-b]pyridin-2-yl)-5,6-dimethoxypyrrolo[3,2-b]pyridin-1-yl]propyl}diethylamine 3-(4-chloro-1H-pyrrolo[2,3-b]pyridin-$^2$-yl)-5,6-dimethoxy-1-[3-(4-methyl-perhydro-1,4-diazepin-1-yl)-propyl]-1H-pyrrolo[3,2-b]pyridine 2-(5,6-dimethoxy-1-methyl-1H-pyrrolo[3,2-b]pyridin-3-yl)-1H-pyrrolo[2,3-b]pyridine-4-carbonitrile Example 32

2-[3-(4-chloro-1H-pyrrolo[2,3-b]pyridin-2-yl)-5,6-dimethoxypyrrolo[3,2-b]pyridin-1-yl]-N-methoxy-N-methylacetamide

[2-(5,6-dimethoxy-1-methyl-1H-pyrrolo[3,2-b]pyridin-3-yl)-1H-pyrrolo[2,3-b]pyridin-4-ylmethyl]-(4-morpholin-4-ylphenyl)amine

[2-(5,6-dimethoxy-1-methyl-1H-pyrrolo[3,2-b]pyridin-3-yl)-1H-pyrrolo[2,3-b]pyridin-4-carbaldehyde oxime 4-{[2-(5,6-dimethoxy-1-methyl-1H-pyrrolo[3,2-b]pyridin-3-yl)-1H-pyrrolo[2,3-b]pyridin-4-ylmethyl]amino}phenol and also said prodrugs thereof, said products of formula (I) being in all the isomeric forms possible: racemic, enantiomeric or diastereoisomeric, as well as the addition salts with organic and inorganic acids or with pharmaceutically acceptable organic and inorganic bases of said products of formula (I).

The products can be administered by the parenteral, buccal, perlingual, rectal or topical route.

The invention also relates to pharmaceutical compositions, characterized in that they contain, as active principle, at least one of the medicinal products of general formula (I).

These compositions can be presented as injectable solutions or suspensions, tablets, coated tablets, capsules, syrups, suppositories, creams, ointments and lotions. These pharmaceutical forms are prepared according to the usual methods. The active principle can be incorporated with the excipients usually employed in these compositions, such as aqueous or nonaqueous vehicles, talc, gum arabic, lactose, starch, magnesium stearate, cocoa butter, fats of animal or vegetable origin, paraffinic derivatives, glycols, various wetting, dispersing or emulsifying agents, preservatives etc.

The usual dose, which varies according to the subject treated and the disorder in question, can be, for example, from 10 mg to 500 mg per day in humans, by the oral route.

The present invention thus relates to the use of products of formula (I) as defined above or of pharmaceutically acceptable salts of said products of formula (I) for the preparation of medicinal products intended to inhibit the activity of protein kinases and notably of one protein kinase.

The present invention thus relates to the use of products of formula (I) as defined above or of pharmaceutically acceptable salts of said products of formula (I) in which the protein kinase is a protein tyrosine kinase.

The present invention thus relates to the use of products of formula (I) as defined above or of pharmaceutically acceptable salts of said products of formula (I) in which the protein kinase is selected from the following group:

IGF1, Raf, EGF, PDGF, VEGF, Tie2, KDR, Flt1-3, FAK, Src, Abl, cKit, cdk1-9, Aurora1-2, cdc7, Akt, Pdk, S6K, Jnk, IR, FLK-1, FGFR1, FGFR2, FGFR3, FGFR4, FGFR5, PLK, Pyk2, CDK7, CDK2 and EGFR.

The present invention thus relates to the use of products of formula (I) as defined above or of pharmaceutically acceptable salts of said products of formula (I) in which the protein kinase is more particularly selected from the following group:

IGF1, cdc7, Aurora1-2, Src, Jnk, FAK, KDR, IR, Tie2, CDK7, CDK2 and EGFR.

The present invention relates especially to the use of products of formula (I) as defined above or of pharmaceutically acceptable salts of said products of formula (I) in which the protein kinase is IGF1R.

The present invention also relates to the use of products of formula (I) as defined above or of pharmaceutically acceptable salts of said products of formula (I) in which the protein kinase is in a cell culture and also this use in a mammal.

The present invention thus relates to the use of products of formula (I) as defined above or of pharmaceutically acceptable salts of said products of formula (I) for the preparation of a medicinal product intended for preventing or treating a disease characterized by dysfunction of the activity of a protein kinase and notably such a disease in a mammal.

The present invention relates to the use of products of formula (I) as defined above or of pharmaceutically acceptable salts of said products of formula (I) for the preparation of a medicinal product intended for preventing or treating a disease included in the following group: disorders of proliferation of blood vessels, fibrotic disorders, disorders of proliferation of mesangial cells, acromegaly, metabolic disorders, allergies, asthma, Crohn's disease, thromboses, diseases of the nervous system, retinopathies, psoriasis, rheumatoid arthritis, diabetes, muscular degeneration, geriatrics, muscular degeneration due to age, oncological diseases, cancers.

The present invention thus relates to the use of products of formula (I) as defined above or of pharmaceutically acceptable salts of said products of formula (I) for the preparation of a medicinal product intended for treating diseases in oncology.

The present invention relates especially to the use of products of formula (I) as defined above or of pharmaceutically acceptable salts of said products of formula (I) for the preparation of a medicinal product intended for treating cancers.

Among these cancers, the present invention relates quite especially to the treatment of solid tumors and to the treatment of cancers that are resistant to cytotoxic agents.

Among these cancers, the present invention relates quite especially to the treatment of cancer of the breast, stomach, colon, lungs, ovaries, uterus, brain, kidney, larynx, lymphatic system, thyroid, urogenital tract, including the bladder and prostate, bone cancer, cancer of the pancreas, and melanomas.

The present invention relates even more particularly to the treatment of cancer of the breast, colon and lungs.

The present invention also relates to the use of products of formula (I) as defined above or of pharmaceutically acceptable salts of said products of formula (I) for the preparation of a medicinal product for the chemotherapy of cancers.

As medicinal products according to the present invention intended for the chemotherapy of cancers, the products of formula (I) according to the present invention can be used alone or in combination with chemotherapy or radiotherapy or alternatively in combination with other therapeutic agents.

The present invention thus relates notably to pharmaceutical compositions as defined above, additionally containing active principles of other medicinal products for chemotherapy against cancer.

Said therapeutic agents can be commonly-used antitumor agents.

As examples of known inhibitors of protein kinases, we may mention notably butyrolactone, flavopiridol, 2-(2-hydroxyethylamino)-6-benzylamino-9-methylpurine, olomucine, Glivec and Iressa.

The products of formula (I) according to the present invention can thus also be used advantageously in combination with antiproliferative agents: as examples of said antiproliferative agents, though without being limited to this list, we may mention aromatase inhibitors, antiestrogens, inhibitors of topoisomerase I, inhibitors of topoisomerase II, agents that act on the microtubules, alkylating agents, inhibitors of histone deacetylase, inhibitors of farnesyl transferase, inhibitors of COX-2, inhibitors of MMP, inhibitors of mTOR, antineoplastic antimetabolites, platinum compounds, compounds causing decrease in activity of protein kinases and also anti-angiogenic compounds, gonadoreline agonists, anti-androgens, bengamides, biphophonates and trastuzumab.

We may thus mention as examples anti-microtubule agents such as the taxoids, vinka-alkaloids, alkylating agents such as cyclophosphamide, DNA-intercalating agents such as cisplatinum, agents that interact with topoisomerase such as camptothecine and derivatives, anthracyclines such as adriamycin, antimetabolites such as 5-fluorouracil and derivatives and analogs.

The present invention therefore relates to products of formula (I) as protein kinase inhibitors, said products of formula (I) being in all possible isomeric forms: racemic, enantiomeric and diastereoisomeric, as well as the pharmaceutically acceptable addition salts with organic and inorganic acids or with organic and inorganic bases of said products of formula (I) as well as their prodrugs.

The present invention relates especially to products of formula (I) as defined above as inhibitors of IGF1R.

The starting products for synthesis of the products of formula (I) according to the present invention can be known, described in the documents, by a person skilled in the art, commercially available or can be prepared according to usual methods known by a person skilled in the art or moreover according to the methods described in the accompanying schemes.

The following experimental part more particularly illustrates examples 1 to 67 of the present application Scheme 1: Synthesis of 5,6-dimethoxy-1-methyl-3-(1H-pyrrolo[2,3-b]pyridin-2-yl)-1H-pyrrolo[3,2-b]pyridine (example 1 or product 16)

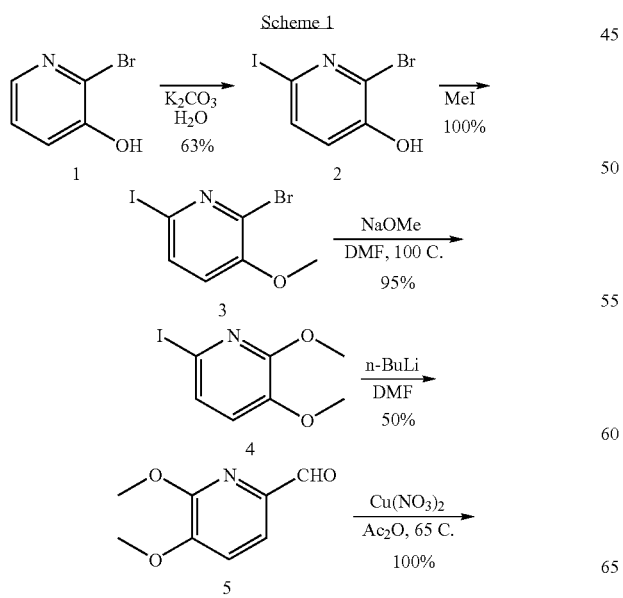

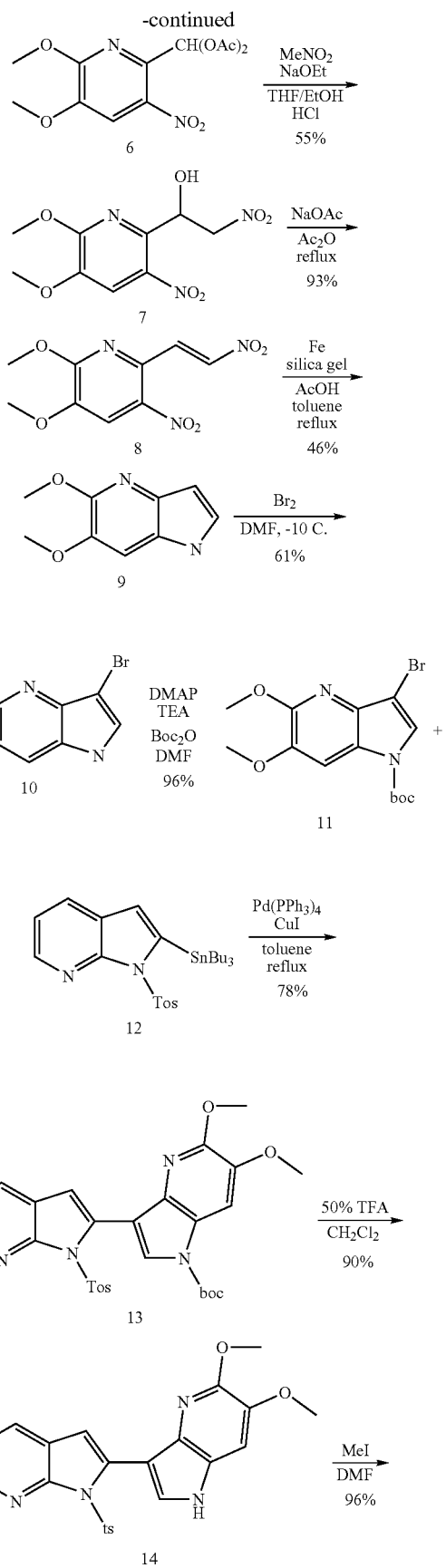

-continued
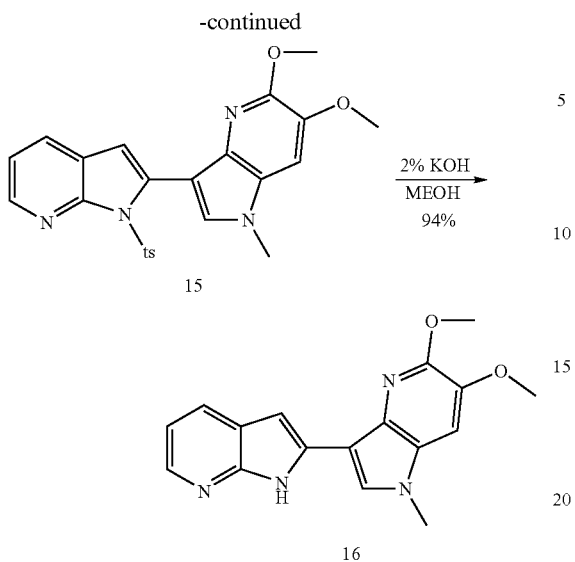
15
16
Scheme 2: Synthesis of 5,6-dimethoxy-1-(2-morpholin-4-yl-ethyl)3-(1H-pyrrolo[2, 3-b]pyridin-2-yl)-1H-pyrrolo[3,2-b]pyridine, (example 2 or product 20)
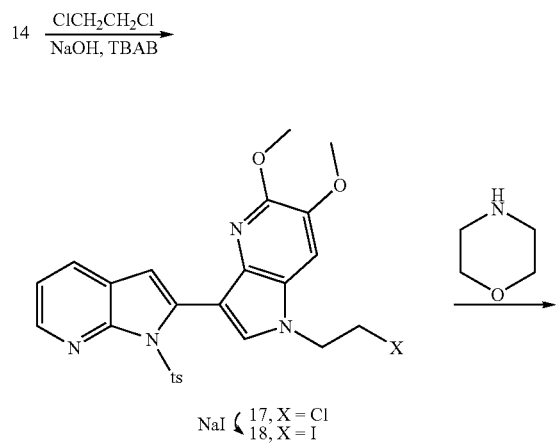
Scheme 2
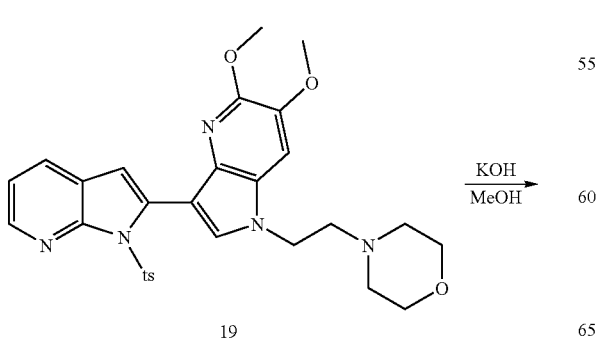
-continued
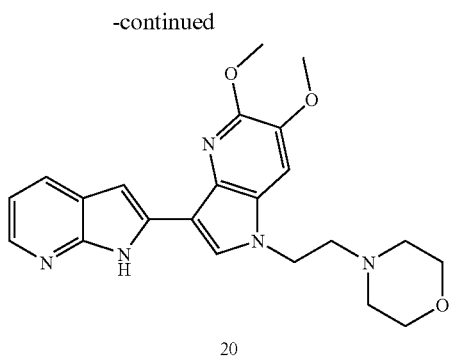
20
Scheme 3: Synthesis of 5,6-dimethoxy-1-[2-(4-methyl-piperazin-1-yl)ethyl]-3-(1H-pyrrolo[2,3-b]pyridin-2-yl)-1H-pyrrolo[3,2-b]pyridine, (example 3 or product 22)
Scheme 3
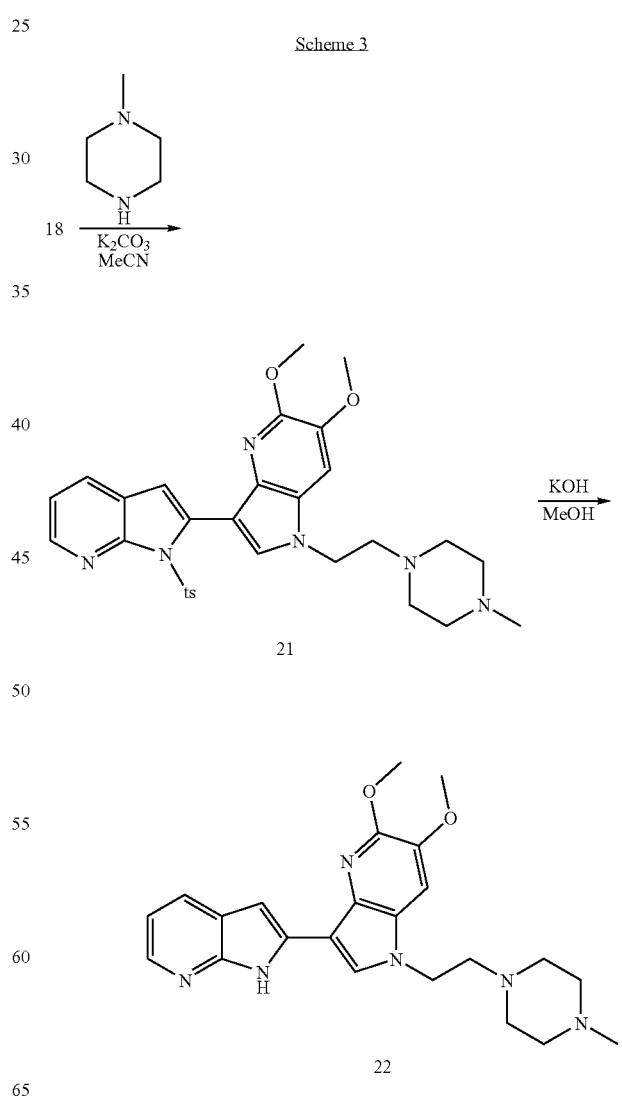

Scheme 4: Synthesis of 3-(4-chloro-1H-pyrrolo[2,3-b]pyridin-2-yl)-5,6-dimethoxy-1-methyl-1H-pyrrolo[3,2-b]pyridine, (example 4 or product 30)
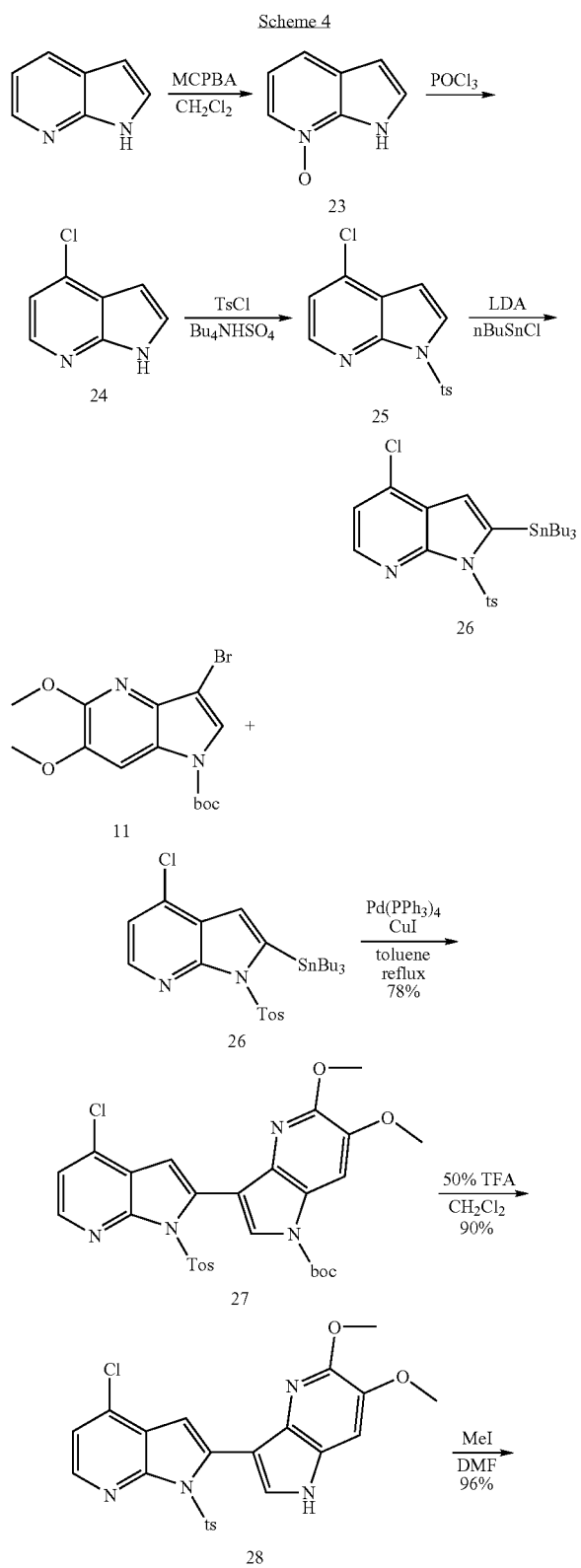
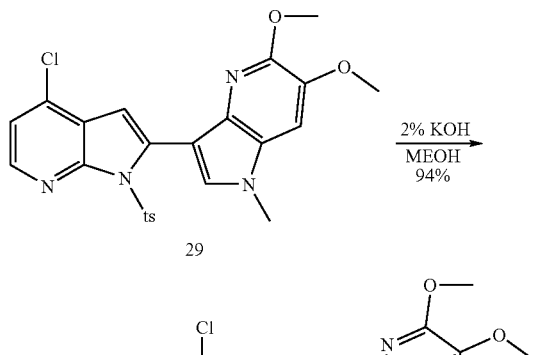
Scheme 5: synthesis of 3-(4-chloro-1H-pyrrolo[2,3-b]pyridin-2-yl)-5,6-dimethoxy-1-(2-morpholin-4-yl-ethyl)-1H-pyrrolo[3,2-b]pyridine, 34. (example 5 or product 34)
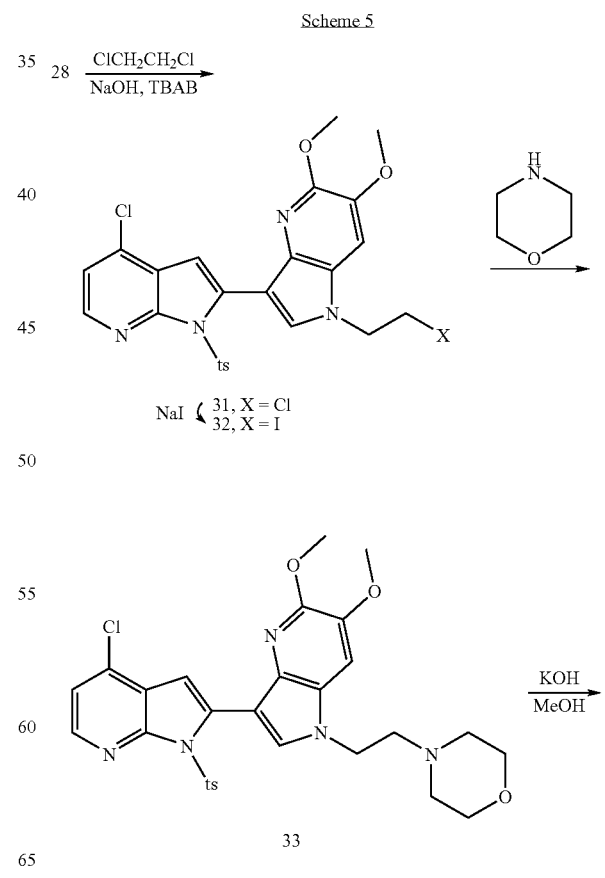

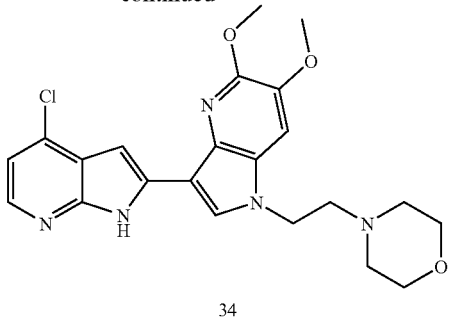

34

Scheme 6: synthesis of 3-(4-chloro-1H-pyrrolo[2,3-b]pyridin-2-yl)-5,6-dimethoxy-1-[2-(4-methylpiper-azin-1-yl)ethyl]-1H-pyrrolo[3,2-b]pyridine, 36. (example 6 or product 36)

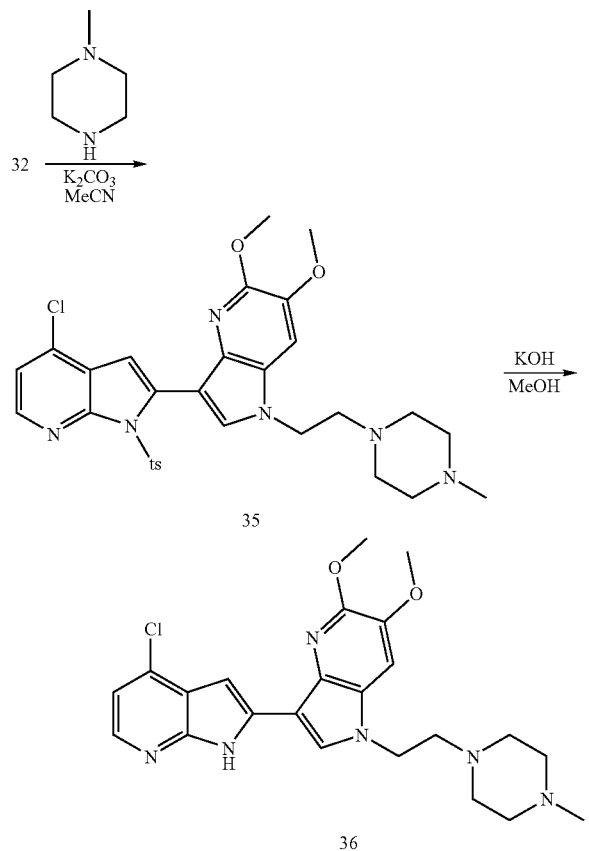

In the preparations following examples 1 to 8 for mass spectrometry, the spectra were obtained by electron impact (EI) and/or chemical desorption-ionization (CI) (reacting gas: ammonia) on a Finnigan SSQ 7000 spectrometer.

General methods of synthesis for the preparation of examples 1 to 8. Unless stated otherwise, the products were obtained from industrial suppliers and were used without further purification. All the reactions were conducted under an inert atmosphere with anhydrous reagents and solvents.

Flash chromatography was carried out on an Isco Combi-Flash Companion™ using Advantage FlashReady™ prepacked silica cartridges and the solvent systems described. Thin-layer chromatography was carried out with 0.25 mm silica gel-coated plates 60F-254 (EM) and visualized with iodine vapor, UV light or a staining reagent such as a solution of $KMnO_4$.

The infrared spectra (IR) were recorded in an IR-TF Nexus 670 spectrometer (Nicolet) with samples prepared in the manner stated, and are expressed as wavenumbers ($cm^{-1}$). The $^1H$ NMR spectra were recorded in Varian Gemini and/or Mercury 300, Unity 400 or Unity plus and/or Inova spectrometers at 500 MHz, the chemical shifts (δ) being expressed in ppm relative to tetramethylsilane (0.0 ppm) or to chloroform ($CDCl_3$, 7.26 ppm) as reference. The $^{13}C$-NMR spectra were recorded on a Varian Unity instrument (13C frequency of 100.57 MHz), the chemical shifts (δ) being expressed in ppm relative to $CDCl_3$ (77.0 ppm), unless indicated otherwise. The mass spectra (MS) were obtained in a Finnigan MAT model TSQ 700 mass spectrometer by chemical ionization at 120 eV with methane (CI, 120 eV). Liquid chromatography—mass spectrometry (LC-MS) was carried out on a Micromass LCT with an interface to a Gilson 215 liquid handler. Analysis by high-resolution mass spectrometry (exact mass spectra) was carried out in ESI mode at a mass resolution of 10 000 by means of a Micromass QTOF mass spectrometer. The exact values of the masses were determined for the protonated molecular ions (M+1), where M denotes the molecular ion.

The examples whose preparation now follows, whether preparations of products or preparations of pharmaceutical compositions, illustrate the present invention though without limiting it.

EXAMPLE 1

5,6-Dimethoxy-1-methyl-3-(1H-pyrrolo[2,3-b]pyridin-2-yl)-1H-pyrrolo[3,2-b]pyridine, 16

Stage 1(a): 2-Bromo-6-iodopyridin-3-ol, 2

Add $I_2$ (21.0 g, 82.7 mmol) in solid form, a little at a time, in the space of 5 min, to a solution of 2-bromo-3-pyridinol (14.0 g, 80.8 mmol) and of $K_2CO_3$ (22.3 g, 161 mmol) in $H_2O$ (180 mL). Stir the reaction medium at room temperature for 2 h, then cool it (ice/$H_2O$) to 0-5° C. and neutralize it to pH 6 by adding 2N HCl. A precipitate forms, which is filtered, washed with $H_2O$ and dried under vacuum at 70° C. to give 2 (19.48, 80.7%) in solid form, of an ivory color: $^1H$ NMR ($CDCl_3$) δ 7.54 (d, 1H, J=8.1 Hz), 6.98 (d, 1H, J=8.1 Hz), 5.55 (s broad, 1H); m/z obs.=299.4 (M+1).

Stage 1(b): 2-Bromo-6-iodo-3-methoxypyridine, 3

Add $K_2CO_2$ (6.22 g, 45.1 mmol) and methyl iodide (24.6 g, 10.77 mL, 173.3 mmol) to 2-bromo-6-iodopyridin-3-ol, 2 (14.9 g, 49.5 mmol), dissolved in DMF (30 mL). Heat the reaction medium at 100° C. for 2 h, then leave it to cool to room temperature. Then stop the reaction with $H_2O$ and stir it for a further 30 min. The precipitate is then filtered, washed with $H_2O$ and dried in air to give 3 (15.7 g, 100%) in solid form, light brown: $^1H$ NMR ($CDCl_3$) δ 7.61 (d, 1H, J=8.4 Hz), 6.86 (d, 1H, J=8.4 Hz), 3.93 (s, 3H); m/z obs.=314 (M+1), 315.

Stage 1(c): 6-Iodo-2,3-dimethoxypyridine, 4

Add NaOMe (1.4 equiv., 1.25 g, 23.14 mmol) to 2-bromo-6-iodo-3-methoxypyridine, 3 (4.95 g, 15.76 mmol) dissolved in DMF (10 mL), and stir the reaction medium, heating at 100° C. under N₂ for 1 h. After cooling, the reaction mixture is shared between saturated NaHCO₃ and CH₂Cl₂, and the organic phase is dried (MgSO₄) and concentrated. Purification on SiO₂ (EtOAc at 10%/heptane) gives 4 (3.13 g, 74.9% as a white solid: $^1$H NMR (CDCl₃) δ 7.25 (d, 1H, J=7.8 Hz), 6.76 (d, 1H, J=8.1 Hz), 4.03 (s, 3H), 3.87 (s, 3H); m/z obs.=266 (M+1).

Stage 1(d):
5,6-Dimethoxypyridine-2-carboxyaldehyde, 5

Add nBuLi (2.5 M, 1.2 equiv., 2.72 mL, 6.8 mmol) dropwise in the space of 10 min to 6-iodo-2,3-dimethoxypyridine, 4 (1.5 g, 5.66 mmol) dissolved in THF (30 mL) and stirred at −70° C. under N₂. Stir the reaction medium for 30 min at −70° C., allow its temperature to return to 0° C., then add DMF (1.32 mL) and continue stirring at 0° C. for 1 h. Then leave the reaction medium to return to room temperature, stir it for 1 h, then stop the reaction with NH₄Cl/H₂O (2.0 g/5 mL). The usual procedure (EtOAc/brine, drying with MgSO₄) leads to a raw oil which is submitted to flash chromatography (SiO₂, EtOAc at 10%/heptane) to give 5 (0.47 g, 50%) as a white solid: $^1$H NMR (CDCl₃) δ 9.86 (s, 1H), 7.61 (d, 1H, J=7.8 Hz), 7.12 (d, 1H, J=7.8 Hz), 4.10 (s, 3H), 3.96 (s, 3H); m/z obs.=168 (M+1)

Stage 1(e):
Acetoxy-(5,5-dimethoxy-3-nitropyridin-2-yl)methyl acetate, 6

Add cupric nitrate (0.7 g, 2.47 mmol) to 5,6-dimethoxy-pyridine-2-carboxaldehyde, 5 (200 mg, 1.2 mmol) dissolved in acetic anhydride (13 mL) and heated to 65° C. After 2 h has elapsed, the reaction is incomplete according to TLC (EtOAc at 40%/heptane), therefore add an extra amount of cupric nitrate (400 mg), and continue stirring with heating at 65° C. for a further 1 h. Leave the reaction medium to cool, pour it onto an ice/H₂O mixture, neutralize it with solid NaHCO₃, extract it with EtOAc, wash with NaHCO₃, dry (MgSO₄) and concentrate, to obtain 6 (0.337 g, 100%), as a yellow solid: $^1$H NMR (CDCl₃) δ 8.09 (s, 1H), 7.80 (s, 1H), 4.13 (s, 3H), 4.00 (s, 3H), 2.20 (s, 6H); Rf (EtOAc at 40%/heptane)=0.30.

Stage 1(f): 1-(5,6-Dimethoxy-3-nitropyridin-2-yl)-2-nitroethanol, 7

Add MeNO₂ (83 µL, 1.53 mmol) to acetoxy-(5,5-dimethoxy-3-nitropyridin-2-yl)methyl acetate, 6 (270 mg, 0.957 mmol) dissolved in EtOH at 50%/THF (20 mL), then add NaOEt (135 mg, 1.9 mmol) and stir the reaction medium at room temperature overnight. After 16 h, concentrate the reaction mixture under vacuum, add 2N HCl to pH 4 then saturated NaHCO₃, extract with EtOAc (3×), wash with saturated NaHCO₃, dry (MgSO₄) and concentrate, to obtain a raw solid which gives, after flash chromatography (EtOAc at 20%/heptane), 7 as a pale yellow solid: $^1$H NMR (CDCl₃) δ 7.84 (s, 1H), 6.15 (m, 1H), 5.01 (dd, 1H, J=12.4, 4.0 Hz), 4.76 (dd, 1H, J=6.9, 12.6 Hz), 4.30 (d, 1H, J=8.1), 4.16 (s, 3H), 4.02 (s, 3H); Rf (EtOAc at 40%/heptane)=0.20; m/z obs.=274 (M+1).

Stage 1(g): 2,3-Dimethoxy-5-nitro-6-(2-nitrovinyl) pyridine, 8

Bring 1-(5,6-dimethoxy-3-nitropyridin-2-yl)-2-nitroethanol, 7 (173 mg, 0.63 mmol) and NaOAc (208 mg, 2.53 mmol) to reflux in Ac₂O (5.0 mL), following the reaction by LC-MS. After 45 min, pour the reaction mixture onto an ice/H₂O mixture, neutralize with NaHCO₃, extract with EtOAc, wash with saturated NaHCO₃, dry (MgSO₄) and concentrate. Purify the raw product by flash chromatography (EtOAc at 20%/heptane) to give 8 (144 mg, 89.2%) as an ivory-colored solid, which is an 8:2 mixture of isomers: $^1$H NMR (CDCl₃) δ 8.68 (d, 0.8 H, J=12.9 Hz), 8.57 (d, 1.6 H, J=13 Hz), 7.99 (d, 0.83 H, J=12.9 Hz), 7.72 (d, 1H, J=11.7 Hz), 7.3 (d, 0.15 H, J=12 Hz), 4.18 (s, 2.6 H), 4.15 (s, 0.56 H), is 4.05 (s, 2.8 H), 3.97 (0.54 H); Rf (EtOAc at 40%/heptane, two spots)=0.4 and 0.42; m/z obs.=256 (M+1).

Stage 1(h):
5,6-Dimethoxy-1H-pyrrolo[3,2-b]pyridine, 9

Heat a mixture of 2,3-dimethoxy-5-nitro-6-(2-nitrovinyl) pyridine, 8 (144 mg, 0.565 nmmol), Fe (0.6 g, 0.565 nmmol), SiO₂ (0.565 g) under reflux in ACOH (3.4 mL) and toluene (5.7 mL). After 1 h, leave the reaction medium to cool to room temperature. Filter the reaction mixture and wash the solid with CH₂Cl₂ and discard. Then wash the filtrate with aqueous Na₂SO₃ at 1%/Na₂S₂O₅, then with saturated NaHCO₃, dry (MgSO₄) and concentrate under vacuum. Purify the raw product by flash chromatography (EtOAc at 40%/heptane) to give 9 (46 mg, 46%) as a fawn-colored solid: $^1$H NMR (CDCl₃) δ 8.04 (s broad, 1H), 7.19 (m, 1H), 7.12 (s, 1H), 6.55 (m, 1H), 4.09 (s, 3H), 3.90 (s, 3H); Rf (EtOAc at 40%/heptane)=0.10; m/z obs.=178.94 (M+1).

Stage 1(i):
3-Bromo-5,6-dimethoxy-1H-pyrrolo[3,2-b]pyridine, 10

Add Br (1.08 equiv., 160 mg, 0.936 mmol) in DMF (5 mL) to 5,6-dimethoxy-1H-pyrrolo[3,2-b]pyridine, 9 (165 mg, 0.927 mmol), and KOH (1.10 equiv., 67 mg, 1.02 mmol) dissolved in DMF (10 mL), at a temperature of −5 to −10° C. in the space of 45 minutes. Once addition is completed, dilute the reaction medium with EtOAc (200 mL), wash with saturated NaHCO₃, dry (MgSO₄) and concentrate under vacuum. The raw product is submitted to flash chromatography on SiO₂ (EtOAc at 20%/heptane) to give 10 (147 mg, 61%) as an ivory-colored solid: $^1$H NMR (CDCl₃) δ 8.10 (s broad, 1H), 7.21 (d, 1H, J=2.7 Hz), 7.11 (s, 1H), 4.15 (s, 3H), 3.93 (s, 3H); Rf (EtOAc at 40%/heptane)=0.15; m/z obs.=258 (M+1).

Stage 1(j): t-Butyl 3-bromo-5,6-dimethoxy-pyrrolo [3,2-b]pyridine-1-carboxylate, 11

Add DMAP (0.075 equiv., 1.3 mg, 0.0108 mmol), Et₃N (1.2 equiv., 17.5 mg, 24 µL, 0.1728 mmol) and Boc₂O (1.25 equiv., 40 mg, 0.18 mmol) to 3-bromo-5,6-dimethoxy-1H-pyrrolo[3,2-b]pyridine, 10 (37 mg, 0.144 mmol) in DMF (5.0 mL), at 0 C. Leave the reaction medium to return to room temperature, while stirring. After 2 h, dilute the reaction mixture with EtOAc, wash with saturated NaHCO₃, dry (MgSO₄) and concentrate, to give 11 (51 mg, 100%) as a white solid: $^1$H NMR (CDCl₃) δ 7.89 (s broad, 1H), 7.59 (s, 1H), 4.13 (s, 3H), 3.94 (s, 3H), 1.66 (s, 9H); Rf (EtOAc at 40%/heptane)=0.55; m/z obs.=358 (M+1).

Stage 1(k): 1-(Toluene-4-sulfonyl)-2-tributylotannanyl-1H-pyrrolo[2,3-b]pyridine, 12

Add n-BuLi (2.5 M, 0.85 mL) dropwise, in the space of 10 min, to a solution of N-tosyl-7-azaindole (0.5 g, 1.84 nmmol)

in THF (20 mL) at −78° C. After stirring the reaction medium for 30 min at −78° C., add Bu$_3$SnCl dropwise (0.575 mL, 2.12 mmol), and leave the reaction to return gradually to room temperature. After 16 h, stop the reaction with H$_2$O and extract with EtOAc, wash with brine, dry (MgSO$_4$) and concentrate, to give a raw oil which is submitted to flash chromatography immediately, on SiO$_2$ pretreated with Et$_3$N/CH$_2$Cl$_2$, which is washed with CH$_2$Cl$_2$. Elution with EtOAc at 5%/heptane gives 12 (0.62 g, 60%) as a colorless oil: $^1$H NMR (CDCl$_3$) δ 8.27 (d, 1H, J=6 Hz), 7.98 (d, 2H, J=8 Hz), 7.74 (d, 1H, J=9), 7.23 (d, 2H, J=12), 7.07 (dd, 1H, J=4.8, 7.8 Hz), 6.67 (s, 1H), 2.35 (s, 3H), 1.58 (m, 6H), 1.38 (m, 6H), 1.27 (m, 6H), 0.89 (m, 9H). TLC (EtOAc at 10%/heptane) Rf=0.15, m/z obs.=562 (M+1).

Stage 1(l): t-Butyl 5,6-dimethoxy-3-[1-(toluene-4-sulfanyl)-1H-pyrrolo[2,3-b]pyridin-2-yl]pyrrolo[3,2-b]pyridine-1-carboxylate, 13

Dissolve 4-azaindole 11 (435 mg, 1.22 mmol) and 7-azaindole 12 (752 mg, 1.34 mmol) in toluene (20 mL) and bubble N$_2$ in the reaction mixture for 30 min, then add Pd(PPh$_3$)$_4$ (141 mg, 0.122 mmol) and CuI (23.2 mg, 0.122 mmol), and heat the reaction medium at 120° C. for 20 h. On completion of the reaction, according to LC-MS, the reaction mixture is concentrated under vacuum and purified by flash chromatography (EtOAc at 15%/heptane) to give 13 (519.6 mg, 77.8%) as a pale yellow solid: $^1$H NMR (CDCl$_3$) δ 8.40 (dd, 1H, J=4.8, 1.8 Hz), 7.95 (s broad, 1H), 7.83 (d, 2H, J=8.4 Hz), 7.77 (dd, 2H, J=7.6, 1.6 Hz), 7.13 (m, 3H), 6.84 (s, 1H), 3.97 (s, 6H), 2.31 (s, 3H), 1.71 (s, 9H). TLC (EtOAc at 40%/heptane) Rf=0.35, m/z obs.=549.28 (M+1).

Stage 1(m): 5,6-Dimethoxy-3-[1-(toluene-4-sulfanyl)-1H-pyrrolo[2,3-b]pyridin-2-yl]-1H-pyrrolo[3,2-b]pyridine, 14

Treat bisazaindole 13 (0.52 g, 0.95 mmol) with TFA at 50%/CH$_2$Cl$_2$ (25 mL) and stir at room temperature for 2.5 h. Then concentrate the reaction medium under vacuum to give a yellow oil which solidifies when Et$_2$O is added. The solid is dissolved in EtOAc, washed with saturated NaHCO$_3$, dried (MgSO$_4$) and concentrated, to give 14 (384 mg, 90%) as a yellow solid: $^1$H NMR (CDCl$_3$) δ 8.48 (s broad, 1H), 8.38 (dd, 1H, J=4.8, 1.5 Hz), 7.73 (m, 3H), 7.54 (s broad, 1H), 7.15 (m, 2H), 7.05 (d, 2H, J=7.8 Hz), 6.95 (s, 1H), 4.00 (s, 3H), 3.90 (s, 3H), 2.28 (s, 3H). TLC (EtOAc at 40%/heptane) Rf=0.05, m/z obs.=449 (M+1).

Stage 1(n): 5,6-Dimethoxy-1-methyl-3-[1-(toluene-4-sulfanyl)-1H-pyrrolo[2,3-b]pyridin-2-yl]-1H-pyrrolo[3,2-b]pyridine, 15

Add iodomethane (1.5 equiv., 118 mg, 52 μL, 0.83 mmol) to bisazaindole 14 (248 mg, 0.554 mmol) and NaOH (5.0 equiv., 111 mg, 2.77 nmmol, dissolved in 1.0 mL of H$_2$O) stirred in DMF (20 mL) at 0° C., under N$_2$, and monitor the reaction by LC-MS. After 1.5 h, dilute the reaction medium with EtOAc (200 mL), wash with saturated NaHCO$_3$, dry (MgSO$_4$) and concentrate under vacuum. The raw product is submitted to flash chromatography to give 15 (245 mg, 95.7%) as a white solid: $^1$H NMR (CDCl$_3$) δ 8.35 (dd, 1H, J=4.8, 1.8 Hz), 7.69 (m, 3H), 7.48 (s, 1H), 7.09 (m, 2H), 7.03 (d, 2H, J=8.4 Hz), 6.97 (s, 1H), 4.01 (s, 3H), 3.98 (s, 3H), 3.86 (s, 3H), 2.27 (s, 3H). TLC (EtOAc at 40%/heptane) Rf=0.05, m/z obs.=463.29 (M+1).

Stage 1(o): 5,6-Dimethoxy-1-methyl-3-(1H-pyrrolo[2,3-b]pyridin-2-yl)-1H-pyrrolo[3,2-b]pyridine, 16

Treat bisazaindole 15 (245 mg, 0.53 mmol) with KOH (0.9 g) in MeOH (40 mL) and heat it under reflux under N$_2$ for 7 h. Concentrate the reaction medium under vacuum and dilute the residue with EtOAc (200 mL), wash with saturated NaHCO$_3$, dry (MgSO$_4$) and concentrate. Flash chromatography gives 16 (154 mg, 94.5%) as a white solid: $^1$H NMR (CDCl$_3$) δ 10.76 (s broad, 1H), 8.18 (d, 1H, J=3.9 Hz), 7.79 (d, 1H, J=7.5 Hz), 7.40 (s, 1H), 7.00 (m, 2H), 6.53 (s, 1H), 4.21 (s, 3H), 3.93 (s, 3H), 3.75 (s, 3H). TLC (5% MeOH/CH$_2$Cl$_2$) Rf=0.2, m/z obs.=309.36 (M+1).

EXAMPLE 2

Synthesis of 5,6-dimethoxy-1-(2-morpholin-4-yl-ethyl)-3-(1H-pyrrolo[2,3-b]pyridin-2-yl)-1H-pyrrolo[3,2-b]pyridine, 20

Stage 2(a): 1-(2-Chloroethyl)-5,6-dimethoxy-3-[1-(toluene-4-sulfonyl)-1H-pyrrolo[2,3-b]pyridin-2-yl]-1H-pyrrolo[3,2-b]-pyridine, 17

Add 1,2-dichloroethane (1.4 mL) to bisazaindole 14 (120 mg, 0.268 mmol), then NaOH (500 mg in 1.4 mL of H$_2$O) and tetrabutylammonium bromide (8.0 mg, 0.025 mmol). Heat the reaction medium at 50° C. for 16 h. Leave the reaction medium to cool to room temperature, extract it with CH$_2$Cl$_2$ (3×), dry the combined extracts (MgSO$_4$) and concentrate them under vacuum. The raw product is submitted to flash chromatography to give 17 (93 mg, 68%) as an ivory-colored solid: $^1$H NMR (CDCl$_3$) δ 8.40 (dd, 1H, J=4.8, 1.5 Hz), 7.75 (dd, 1H, J=5, 1.2 Hz), 7.70 (d, 2H, J=8 Hz), 7.59 (s, 1H), 7.15 (m, 2H), 7.04 (d, 2H, J=8 Hz), 7.01 (s, 1H), 4.52 (t, 2H), 4.05 (s, 3H), 4.0 (s, 3H), 3.92 (t, 2H), 2.3 (s, 3H). TLC (EtOAc at 40%/heptane) Rf=0.05, m/z obs.=512 (M+1).

Stage 2(b): 1-(2-Iodoethyl)-5,6-dimethoxy-3-[1-(toluene-4-sulfonyl)-1H-pyrrolo[2,3-b]pyridin-2-yl]-1H-pyrrolo[3,2-b]-pyridine, 18

Add NaI (1.10 equiv., 30 mg, 0.20 mmol) to bisazaindole 17 (93 mg, 0.182 mmol) in 2-butanone (10 mL). After 16 h of reflux, the reaction mixture is concentrated under vacuum and the residue is dissolved in EtOAc (100 mL), washed with brine, dried (MgSO$_4$) and concentrated, to give 18 (105 mg, 91%) as an ivory-colored solid: TLC (EtOAc at 40%/heptane) Rf=0.08, m/z obs.=604 (M+1).

Stage 2(c): 5,6-Dimethoxy-1-(2-morpholin-4-yl-ethyl)-3-[1-(toluene-4-sulfonyl)-1H-pyrrolo[2,3-b]pyridin-2-yl]-1H-pyrrolo[3,2-b]pyridine, 19

Stir bisazaindole iodide 18 (52 mg, 0.0862 mmol), morpholine (1.10 equiv., 8.26 mg, 8.3 μL, 0.0948 mmol) and K$_2$CO$_3$ (13 mg, 0.0942 mmol), with heating at 60° C. in CH$_3$CN (6 mL) under N$_2$, for 24. LC-MS shows that the reaction is only 50% complete. Add extra morpholine (17 μL) and continue stirring at 60° C. After 48 h, the reaction medium is concentrated under vacuum and the residue is submitted to flash chromatography to give 19 (48 mg, 99%) as a white solid: $^1$H NMR (CDCl$_3$) δ 8.38 (dd, 1H, J=4.5, 1.2 Hz), 7.75 (dd, 1H, J=4.5, 1.2 Hz), 7.68 (d, 2H, J=8.4 Hz), 7.62 (s, 1H), 7.14 (m, 2H), 7.05 (d, 2H, J=8.4 Hz), 7.02 (s, 1H), 4.28 (t, 2H), 4.05 (s, 3H), 4.0 (s, 3H), 3.74 (m, 4H), 2.90 (t, 2H), 2.55

(m, 4H), 2.29 (s, 3H). TLC (MeOH at 4%/CH$_2$Cl$_2$, 0.25% of NH$_3$) Rf=0.65, m/z obs.=562.15 (M+1)

Stage 2(d): 5,6-Dimethoxy-1-(2-morpholin-4-yl-ethyl)-3-(1H-pyrrolo[2,3-b]pyridin-2-yl)-1H-pyrrolo[3,2-b]pyridine, 20

Bring bisazaindole 19 (48 mg, 0.0856 mmol) to reflux in KOH at 3%/MeOH for 8 h, then continue heating at 55° C. for 16 h. The reaction medium is then concentrated under vacuum, the residue is diluted with EtOAc, washed with saturated NaHCO$_3$, dried (MgSO$_4$), and concentrated until a residual oil is obtained. The latter is submitted to flash chromatography to give 20 (19.7 mg, 56.6%) as a white solid: $^1$H NMR (CDCl$_3$) δ 10.77 (s broad, 1H), 8.20 (d, 1H, J=4.5 Hz), 7.82 (d, 1H, J=7.5 Hz), 7.57 (s, 1H), 7.13 (s, 1H), 7.03 (m, 1H), 6.57 (d, 1H, J=1.5 Hz), 4.23 (s, 3H), 4.22 (t, 2H, J=6.6 Hz), 3.96 (s, 3H), 3.70 (t, 4H, J=4.6 Hz), 2.77 (t, 2H, J=6.4 Hz), 2.49 (t, 4H, J=4.6 Hz). TLC (MeOH at 4%/CH$_2$Cl$_2$, 0.25% of NH$_3$) Rf=0.20, m/z obs.=408.26 (M+1).

EXAMPLE 3

Synthesis of 5,6-dimethoxy-1-[2-(4-methyl-piperazin-1-yl)ethyl]-3-(1H-pyrrolo[2,3-b]pyridin-2-yl)-1H-pyrrolo[3,2-b]pyridine, 22

Stage 3(a): 5,6-Dimethoxy-1-[2-(4-methylpiperazin-1-yl)ethyl]-3-[1-(toluene-4-sulfonyl)-1H-pyrrolo[2,3-b]pyridin-2-yl]-1H-pyrrolo[3,2-b]pyridine, 21

Add K$_2$CO$_3$ (1.1 equiv., 13.2 mg, 0.095 mmol) to bisazaindole iodide 18 (52 mg, 0.0862 mmol) in CH$_3$CN (6.0 mL) at 60° C., then add 1-methylpiperazine (1.10 equiv., 9.515 mg, 10.55 µL, 0.095 mmol). After stirring for 2 h at 60° C., add extra K$_2$CO$_3$ (13.2 mg) and 1-methylpiperazine (21 µL) and continue stirring at 60° C. for 30 h. The reaction mixture is then concentrated to give a residue, which is treated with 2N HCl and washed with CH$_2$Cl$_2$. The aqueous phase is then treated with 2N NaOH until pH>10 and extracted with CH$_2$Cl$_2$, dried (MgSO$_4$) and concentrated under vacuum, to give 21 (10 mg, 20.2%) as an ivory-colored solid: $^1$H NMR (CDCl$_3$) δ 8.35 (dd, 1H, J=4.4, 1.1 Hz), 7.72 (dd, 1H, J=4.4, 1.1 Hz), 7.67 (d, 2H, J=8.4 Hz), 7.60 (s, 1H), 7.15 (m, 2H), 7.03 (d, 2H, J=8.4 Hz), 6.98 (s, 1H), 5.28 (s, 3H), 4.26 (t, 2H), 4.00 (s, 3H), 3.97 (s, 3H), 2.86 (t, 2H), 2.55 (m broad, 8H), 2.30 (s, 3H). TLC (MeOH at 10%/CH$_2$Cl$_2$, 0.25% of NH$_3$) Rf=0.35, m/z obs.=575 (M+1).

Stage 3(b): 5,6-Dimethoxy-1-[2-(4-methylpiperazin-1-yl)-ethyl]-3-(1H-pyrrolo[2,3-b]pyridin-2-yl)-1H-pyrrolo[3,2-b]pyridine, 22

Bring bisazaindole 21 (10 mg, 0.017 mmol) to reflux in KOH at 3%/MeOH (10 mL) for 5 h. Concentrate the reaction mixture, dilute the residue with H$_2$O, add 2N HCl to adjust the pH to 8, extract with CH$_2$Cl$_2$, dry (MgSO$_4$) and concentrate. Purification by flash chromatography leads to 22 (3.4 mg, 46.6%) as an ivory-colored solid: $^1$H NMR (CDCl$_3$) δ 10.77 (s broad, 1H), 8.22 (d, 1H, J=4.5 Hz), 7.84 (d, 1H, J=7.4 Hz), 7.59 (s, 1H), 7.15 (s, 1H), 7.03 (m, 1H), 6.58 (d, 1H, J=1.2 Hz), 4.73 (s, 3H), 4.25 (s, 3H) overlapping with (t, 2H), 3.99 (s, 3H), 2.80 (t, 2H), 2.51 (m broad, 8H). TLC (MeOH at 10%/CH$_2$Cl$_2$, 0.25% of NH$_3$) Rf=0.40, m/z obs.=421.14 (M+1).

EXAMPLE 4

Synthesis of 3-(4-chloro-1H-pyrrolo[2,3-b]pyridin-2-yl)-5,6-dimethoxy-1-methyl-1H-pyrrolo[3,2-b]pyridine, 30

Stage 4(a): 1H-Pyrrolo[2,3-b]pyridin-7-ol, 23

Add 7-azaindole (5.67 g, 48.0 mmol) in solution in CH$_2$Cl$_2$ (47 mL), dropwise in the space of 35 min to a solution of MCPBA (77%, 21.52 g, 96.0 mmol) in CH$_2$Cl$_2$ (140 mL) stirred at 0° C., under N$_2$. Leave the reaction medium to return to room temperature and stir it for 1.5 h. The reaction mixture is then filtered and concentrated under vacuum. The residual oil is treated with Et$_2$O (50 mL) and the solid precipitate is filtered, suspended in H$_2$O (50 mL) and alkalized with a saturated aqueous solution of K$_2$CO$_3$ to pH 10. The aqueous phase is then extracted with CHCl$_3$ (7×), dried (MgSO$_4$) and concentrated, to give 23 (3.18 g, 49%) as a brown oil: $^1$H NMR (DMSO-d$_6$) δ 12.5 (s broad, 1H), 8.14 (s broad, 1H), 7.70 (d, 1H, J=7.5 Hz), 7.45 (d, 1H, J=3.0 Hz), 7.06 (t, 1H, J=6.9 Hz), 6.58 (d, 1H, J=3.0 Hz), m/z obs.=135.1 (M+1), 118.1 (M−16).

Stage 4(b): 4-Chloro-1H-pyrrolo[2,3-b]pyridine, 24

Azaindole 23 (3.18 g, 0.0237 mmol) is refluxed in POCl$_3$ (50 mL) for 8 h, after which the POCl$_3$ is eliminated from the reaction medium by vacuum distillation and the residue is treated with H$_2$O and saturated NaHCO$_3$. The precipitate is collected by filtration and dried in air. Purification by flash chromatography leads to 24 (0.84 g, 22%) as a white crystalline solid: $^1$H NMR (CDCl$_3$) δ 9.5 (s broad, 1H), 8.18 (d, 1H, J=5.4 Hz), 7.36 (dd, 1H, J=3.5, 2.3 Hz), 7.11 (d, 1H, J=5.1 Hz), 6.61 (dd, 1H, J=3.6, 1.8 Hz), TLC (EtOAc at 40%/heptane) Rf=0.10, m/z obs.=152.86 (M+1), 154.86, 193.93 (M+Na).

Stage 4(c): 4-Chloro-1-(toluene-4-sulfonyl)-1H-pyrrolo[2,3-b]pyridine, 25

Add NaOH (3.6 g, 90.2 mmol) as solution in H$_2$O (14 mL) to a solution of 4-chloroazaindole 24 (0.84 g, 5.50 mmol), TsCl (1.154 g, 6.053 mmol) and Bu$_4$NHSO$_4$ (16 µL, 50% in H$_2$O) in toluene (16 mL). After stirring the reaction medium for 2.5 h at room temperature, the two-phase reaction medium is then extracted with EtOAc (2×), dried (MgSO$_4$) and concentrated under vacuum. Flash chromatography gives 25 (1.33 g, 78%) as a white solid: $^1$H NMR (CDCl$_3$) δ 8.28 (d, 1H, J=5.1 Hz), 8.04 (dd, 2H, J=8.5, 2.0 Hz), 7.75 (d, 2H, J=4.0 Hz), 7.26 (d, 1H, J=8.4 Hz), 7.17 (d, 1H, J=5.1 Hz), 6.67 (d, 1H, J=4.2 Hz), 2.37 (s, 3H), TLC (EtOAc at 40%/heptane) Rf=0.50, m/z obs.=307 (M+1), 308.9.

Stage 4(d): 4-Chloro-1-(toluene-4-sulfonyl)-2-tributylstannanyl-1H-pyrrolo[2,3-b]pyridine, 26

Add LDA (1.5 equiv., 0.74 mL, 1.47 mmol) dropwise in the space of 5 min to azaindole 25 (0.3 g, 0.98 mmol) in THF (15 mL), stirred at −78° C., under N$_2$. After stirring the reaction medium for 0.5 h, add Bu$_3$SnCl dropwise (475 mg, 400 µL, 1.47 mmol) and stir the reaction medium for a further 0.5 h. Then allow the reaction medium to return to room temperature, stop the reaction with $H_2O$, dilute with EtOAc (200 mL), wash with brine, dry ($MgSO_4$) and concentrate. The residue is submitted to flash chromatography to give 26 (0.46 g, 79%) as a colorless oil: $^1$H NMR ($CDCl_3$) δ 8.15 (d, 1H, J=5.1 Hz), 7.97 (dd, 2H, J=8.0, 1.5 Hz), 7.27 (d, 2H, J=8.4 Hz), 7.09 (d, 1H, J=5.2 Hz), 6.75 (s, 1H), 2.36 (s, 3H), 1.65-1.20 (m, 12H), 0.93 (t, 9H), TLC (EtOAc at 40%/heptane) Rf=0.65.

Stage 4 (e): t-Butyl 3-[4-chloro-1-(toluene-4-sulfonyl)-1H-pyrrolo[2,3-b]pyridin-2-yl]-5,6-dimethoxy-pyrrolo[3,2-b]pyridine-1-carboxylate, 27

Bubble a solution of dimethoxyazaindole 11 (0.25 g, 0.70 mmol) and azaindole 26 (0.458 g, 0.77 mmol) in toluene (15 mL) with $N_2$ for 15 min, then add CuI (14 mg, 0.07 mmol) and Pd(PPh$_3$)$_4$ (81 mg, 0.07 mmol) and agitate the mixture with the stream of $N_2$ for 0.5 h, then heat at 120° C. under $N_2$ for 20 h. Purification of the reaction mixture on $SiO_2$ (flash chromatography, 40 g cartridge, elution with EtOAc at 10-30%/heptane) gives bisazaindole 27 (0.28 g, 68%) as a white solid: $^1$H NMR ($CDCl_3$) δ 8.29 (d, 1H, J=5.4 Hz), 7.86 (s apparent overlapping d, 3H), 7.15 (m, 4H), 6.94 (s, 1H), 3.97 (s, 6H), 2.32 (s, 3H), 1.71 (s, 9H), TLC (EtOAc at 40%/heptane) Rf=0.40.

Stage 4(f): 3-[4-Chloro-1-(toluene-4-sulfonyl)-1H-pyrrolo[2,3-b]pyridin-2-yl]-5,6-dimethoxy-1H-pyrrolo[3,2-b]pyridine, 28

Dissolve bisazaindole 27 (0.28 g, 0.48 mmol) in TFA at 50%/$CH_2Cl_2$ (8.0 mL) and stir at room temperature for 5 h. The reaction medium is concentrated under vacuum, and the residue is dissolved in EtOAc (100 mL), washed with saturated $NaHCO_3$ (3×), dried ($MgSO_4$) and concentrated, to give 28 (0.222 g, 96%) as an amorphous solid: TLC (EtOAc at 40%/heptane) Rf=0.05.

Stage 4(g): 3-[4-Chloro-1-(toluene-4-sulfonyl)-1H-pyrrolo[2,3-b]pyridin-2-yl]-5,6-dimethoxy-1-methyl-1H-pyrrolo[3,2-b]pyridine, 29

Add KOH (5.0 equiv., 21.6 mg) then MeI (5.0 equiv., 55.0 mg, 24 µL) to bisazaindole 28 (37.3 mg, 0.0772 mmol) stirred in DMF (5.0 mL) at 0° C., and stir the reaction medium at for 1.5 h. Then allow the reaction medium to return to room temperature, dilute it with EtOAc, wash it with saturated $NaHCO_3$, dry ($MgSO_4$) and concentrate, to obtain 29 (40 mg, 100%) as an amorphous solid: TLC (EtOAc at 40%/heptane) Rf=0.10.

Stage 4(h): 3-(4-Chloro-1H-pyrrolo[2,3-b]pyridin-2-yl)-5,6-dimethoxy-1-methyl-1H-pyrrolo[3,2-b]pyridine, 30

Reflux bisazaindole 29 (40 mg, 0.081 mmol) in KOH at 4%/MeOH (10 mL) for 5.5 h and then concentrate the reaction under vacuum. Purification on $SiO_2$ (MeOH at 2-4%/$CH_2Cl_2$) leads to 30 (13 mg, 47.3%) as a white solid: $^1$H NMR ($CDCl_3$) δ 10.92 (s broad, 1H), 8.07 (d, 1H, J=5.3 Hz), 7.49 (s, 1H), 7.05 (s apparent overlapping d, 2H, J=5.2 Hz), 6.62 (s, 1H), 4.22 (s, 3H), 3.96 (s, 3H), 3.81 (s, 3H), TLC (EtOAc at 40%/heptane), Rf=0.40, m/z obs.=343.3 (M+1), 345.3.

EXAMPLE 5

Synthesis of 3-(4-chloro-1H-pyrrolo[2,3-b]pyridin-2-yl)-5,6-dimethoxy-1-(2-morpholin-4-yl-ethyl)-1H-pyrrolo[3,2-b]pyridine, 34

Stage 5(a): 1-(2-Chloroethyl)-3-[4-chloro-1-(toluene-4-sulfonyl)-1H-pyrrolo[2,3-b]pyridin-2-yl]-5,6-dimethoxy-1H-pyrrolo[3,2-b]pyridine, 31

Heat a mixture of bisazaindole 28 (180 mg, 0.373 mmol), 1,2-dichloroethane (2.0 mL), 9N NaOH (2.0 mL) and tetrabutylammonium bromide (16 mg), with stirring, at 50° C. for 16 h. Then leave the reaction medium to cool to room temperature, extract it with $CH_2Cl_2$ (3×), dry ($Na_2SO_4$) and concentrate under vacuum. Purification on $SiO_2$ by flash chromatography gives 31 (110 mg, 54%) as a yellow solid: $^1$H NMR ($CDCl_3$) δ 8.40 (d, 1H, J=5.4 Hz), 7.76 (d, 1H, J=5.2 Hz), 7.70 (d, 2H, J=8.4 Hz), 7.59 (s, 1H), 7.15 (m, 2H), 7.06 (d, 2H, J=8.4 Hz), 7.02 (s, 1H), 4.51 (t, 2H, J=6.4 Hz), 4.06 (s, 3H), 4.00 (s, 3H), 3.90 (t, 2H, J=6.4 Hz), 2.30 (s, 3H), TLC (EtOAc at 40%/heptane) Rf=0.20.

Stage 5(b): 3-[4-Chloro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine, 32

Dissolve chlorobisazaindole 31 (110 mg, 0.202 mmol) and NaI (33.5 mg, 0.222 mmol) in 2-butanone (10 mL) and reflux for 24 h. The reaction medium is then concentrated under vacuum, the residue is dissolved in EtOAc, washed with brine, dried ($Na_2SO_4$) and concentrated, to give 32 (124 mg, 96.6%) as a yellow solid: $^1$H NMR ($CDCl_3$) δ 8.25 (d, 1H, J=5.4 Hz), 7.71 (d, 2H, J=8.4 Hz), 7.65 (s, 1H), 7.10 (m, 5H), 4.53 (t, 2H, J=6.4 Hz), 4.03 (s, 3H), 3.99 (s, 3H), 3.50 (t, 2H, J=6.4 Hz), 2.31 (s, 3H), TLC (EtOAc at 40%/heptane) Rf=0.20, m/z obs.=636.9 (M+1), 638.9, 639.94.

Stage 5(c): 3-[4-Chloro-1-(toluene-4-sulfonyl)-1H-pyrrolo[2,3-b]pyridin-2-yl]-5,6-dimethoxy-1-(2-morpholin-4-yl-ethyl)-1H-pyrrolo[3,2-b]pyridine, 33

Add morpholine (3.5 equiv., 25.9 mg, 26.1 µmol, 0.30 mmol) and $K_2CO_3$ (11.7 mg, 0.085 mmol) to bisazaindole 32 (54 mg, 0.0848 mmol) in $CH_3CN$ (6.0 mL). After heating at 60° C. for 30 h, concentrate the reaction medium under vacuum and submit the residue of raw product to flash chromatography on $SiO_2$ (MeOH at 2-4%/$CH_2Cl_2$) to obtain 33 (40 mg, 79.2%) as an ivory-colored solid: $^1$H NMR ($CDCl_3$) δ 8.26 (d, 1H, J=5.4 Hz), 7.72 (d, 2H, J=8.4 Hz), 7.66 (s, 1H), 7.16 (m, 3H), 7.09 (d, 2H, J=8.1 Hz), 4.29 (t, 2H, J=6.6 Hz), 4.05 (s, 3H), 4.01 (s, 3H), 3.73 (m, 4H), 2.86 (t, 2H, J=6.6 Hz), 2.55 (m, 4H), 2.33 (s, 3H), TLC (MeOH at 4%/$CH_2Cl_2$, 0.25% of $NH_3$) Rf=0.25, m/z obs.=597.56 (M+1)

Stage 5(d): 3-(4-Chloro-1H-pyrrolo[2,3-b]pyridin-2-yl)-5,6-dimethoxy-1-(2-morpholin-4-ylethyl)-1H-pyrrolo[3,2-b]-pyridine, 34

Treat bisazaindole 33 (40 mg, 0.067 mmol) with KOH at 3%/MeOH (10 mL) and reflux for 16 h. Concentrate the reaction medium under vacuum and divide the residue between EtOAc and saturated $NaHCO_3$. The organic phase is washed with saturated $NaHCO_3$, dried ($Na_2SO_4$) and submitted to flash chromatography on $SiO_2$ (MeOH at 2-4%/$CH_2Cl_2$) to give 34 (19.0 mg, 64.2%) as a white solid: $^1$H NMR ($CDCl_3$) δ 10.94 (s broad, 1H), 8.07 (d, 1H, J=5.0 Hz), 7.62 (s, 1H), 7.14 (s, 1H), 7.05 (d, 1H, J=5.3 Hz), 6.66 (d, 1H, J=1.9 Hz), 4.23 (s overlapping t, 5H, J=6.4 Hz), 3.97 (s, 3H), 3.70 (t, 4H, J=4.6 Hz), 2.79 (t, 2H, J=6.4 Hz), 2.50 (t, 4H, J=4.6 Hz), TLC (MeOH at 4%/$CH_2Cl_2$, 0.25% of $NH_3$) Rf=0.25, m/z obs.=442.1 (M+1).

EXAMPLE 6

Synthesis of 3-(4-Chloro-1H-pyrrolo[2,3-b]pyridin-2-yl)-5,6-dimethoxy-1-[2-(4-methylpiperazin-1-yl)ethyl]-1H-pyrrolo[3,2-b]pyridine, 36

Stage 6(a): 3-[4-Chloro-1-(toluene-4-sulfonyl)-1H-pyrrolo[2,3-b]pyridin-2-yl]-5,6-dimethoxy-1-[2-(4-methylpiperazin-1-yl)ethyl]-1H-pyrrolo[3,2-b]pyridine, 35

Add 1-methylpiperazine (3.5 equiv., 35.2 mg, 39.1 μmol, 0.352 mmol) and $K_2CO_3$ (13.8 mg, 0.10 mmol) to bisazaindole 32 (64 mg, 0.10 mmol) in $CH_3CN$ (6.0 mL). After heating at 60° C. for 48 h, the reaction medium is concentrated under vacuum and the residue of raw product is submitted to flash chromatography on $SiO_2$ (MeOH at 2-4%/$CH_2Cl_2$/heptane) to give 35 (40 mg, 64.3%) as a white solid: $^1$H NMR ($CDCl_3$) δ 8.23 (d, 1H, J=5.4 Hz), 7.68 (d, 2H, J=8.1 Hz), 7.61 (s, 1H), 7.10 (m, 5H), 4.25 (t, 2H, J=6.6 Hz), 4.01 (s, 3H), 3.97 (s, 3H), 2.83 (t, 2H, J=6.9 Hz), 2.57-2.46 (m broad, 8H), 2.28 (s, 3H), TLC (MeOH at 10%/$CH_2Cl_2$, 0.25% of $NH_3$) Rf=0.45, m/z obs.=609.04 (M+1).

Stage 6(b): 3-(4-Chloro-1H-pyrrolo[2,3-b]pyridin-2-yl)-5,6-dimethoxy-1-[2-(4-methylpiperazin-1-yl)ethyl]-1H-pyrrolo[3,2-b]pyridine, 36

Reflux bisazaindole 35 (40 mg, 0.066 mmol) in KOH at 3%/MeOH (10 mL) for 16 h, then concentrate under vacuum. The residue is dissolved in EtOAc, washed with saturated $NaHCO_3$, dried ($Na_2SO_4$) and submitted to flash chromatography on $SiO_2$ (MeOH at 4%/$CH_2Cl_2$, 0.25% of $NH_3$) to give 36 (18 mg, 60.2%) as a white solid: $^1$H NMR ($CDCl_3$. δ 10.94 (s broad, 1H), 8.07 (d, 1H, J=5.2 Hz), 7.61 (s, 1H), 7.15 (s, 1H), 7.05 (d, 1H, J=5.2 Hz), 6.65 (d, 1H, J=2 Hz), 4.23 (s overlapping t, 5H, J=6.5 Hz), 3.97 (s, 3H), 2.79 (t, 2H, J=6.5 Hz), 2.55-2.45 (m broad, 8H), 2.29 (s, 3H), TLC (MeOH at 10%/$CH_2Cl_2$, 0.25% of $NH_3$) Rf=0.35, m/z obs.=455.11 (M+1).

EXAMPLE 7

3-(5-fluoro-1H-pyrrolo[2,3-b]pyridin-2-yl)-5,6-dimethoxy-1-(2-morpholin-4-ylethyl)-1H-pyrrolo[3,2-b]pyridine Stage 7(a): 5-fluoro-3-iodopyridin-2-ylamine The 5-fluoro-3-iodopyridin-2-ylamine can be prepared as follows:
A mixture of 9.9 g of 5-fluoropyridin-3-ylamine and 21.85 g of N-iodosuccinimide in 400 $cm^3$ of acetic acid is stirred for about 6 hours at a temperature close to 70° C. After dry concentration at reduced pressure (13 kPa), the residue is absorbed in 250 $cm^3$ of water; the pH is adjusted to about 8 by addition of sodium hydrogencarbonate. The aqueous phase is extracted five times with 150 $cm^3$ of dichloromethane. The combined organic phases are washed three times with 100 $cm^3$ of water, then five times with 50 $cm^3$ of a 10% aqueous solution of sodium thiosulfate, dried over sodium sulfate, filtered and concentrated to dryness at reduced pressure (13 kPa). After flash chromatography on a silica column (eluent: dichloromethane), 11 g of 5-fluoro-3-iodopyridin-2-ylamine is obtained as a solid with the following characteristics:
melting point: melting at 76° C. (Köfler apparatus)
$^1$H NMR spectrum (300 MHz)—δ in ppm—in DMSO-d6: 5.98 (s broad, 2H); from 7.93 to 7.98 (m, 2H).
mass spectrum: MS-EI: 238(+)=M(+)

Stage 7(b): 5-fluoro-3-trimethylsilanylethynyl-pyridin-2-ylamine

5-Fluoro-3-trimethylsilanylethynyl-pyridin-2-ylamine can be prepared as follows:
Add 12.47 $cm^3$ of ethynyltrimethylsilane, 2.24 g of copper iodide, 2.74 g of lithium chloride, 41.33 $cm^3$ of triethylamine and 2.15 g of [1,1'-bis(diphenyl-phosphino)ferrocene]palladium(II) chloride to a solution of 14 g of 5-fluoro-3-iodo-pyridin-2-ylamine in 440 $cm^3$ of dimethylformamide, degassed with argon. The solution obtained is brought to a temperature close to 55° C. for about 5 hours. After it returns to a temperature close to 20° C., the mixture is concentrated at reduced pressure (13 kPa); the residue is absorbed in 300 $cm^3$ of water, and extracted three times with 100 $cm^3$ of ethyl acetate. The combined organic phases are washed three times with 100 $cm^3$ of water, dried over magnesium sulfate, filtered and concentrated at reduced pressure (13 kPa). In this way, after flash chromatography on a silica column (eluent: dichloromethane), 7.91 g of 5-fluoro-3-trimethylsilanylethynylpyridin-2-ylamine is obtained as a solid with the following characteristics:
melting point: melting at 65° C. (Köfler apparatus)
mass spectrum: EI m/z=208 $M^+$; m/z=193 $(M-CH_3)^+$ base peak Stage 7(c): 5-fluoro-1H-pyrrolo[2,3-b]pyridine 5-Fluoro-1H-pyrrolo[2,3-b]pyridine can be prepared as follows:
A mixture of 3.80 g of 5-fluoro-3-trimethylsilanylethynylpyridin-2-ylamine and 3.40 g of potassium tert-butylate in 100 $cm^3$ of 1-methyl-pyrrolidin-2-one is brought close to 130° C. for about 4 hours. After it returns to a temperature close to 20° C., the mixture is poured onto 1000 $cm^3$ of an aqueous solution saturated with sodium chloride and extracted 5 times with 250 $cm^3$ of diethyl oxide. The organic phases are combined, washed 5 times with 100 $cm^3$ of an aqueous solution saturated with sodium chloride, dried over magnesium sulfate, filtered and concentrated to dryness at reduced pressure (13 kPa). 2.35 g of 5-fluoro-1H-pyrrolo[2,3-b]pyridine is obtained as a solid with the following characteristics:
melting point: melting at 110° C. (Köfler apparatus)
mass spectrum: EI m/z=136 $M^{+\cdot}$ base peak m/z=109 $(M-HCN)^+$ Stage 7(d): 5-fluoro-1-(toluene-4-sulfonyl)-1H-pyrrolo[2,3-b]pyridine 5-Fluoro-1-(toluene-4-sulfonyl)-1H-pyrrolo [2,3-b]pyridine can be prepared as follows:
A mixture of 2.30 g of 5-fluoro-1H-pyrrolo[2,3-b]pyridine, 3.54 g of 4-methyl-benzenesulfonyl chloride, of 7.56 g of sodium hydroxide dissolved in 55 $cm^3$ of water, and 0.115 g of tetrabutylammonium hydrogen sulfate in 125 $cm^3$ of toluene is stirred for about 24 hours at around 20° C. The mixture is diluted with 500 cm³ of ethyl acetate; the organic phase is washed three times with 200 cm³ of water, dried over magnesium sulfate, filtered and concentrated to dryness at reduced pressure (13 kPa). The residue is purified by flash chromatography on a silica column [eluent: dichloromethane]. 3.85 g of 5-fluoro-1-(toluene-4-sulfonyl)-1H-pyrrolo[2,3-b]pyridine is obtained as a solid with the following characteristics:

melting point: melting at 160° C. (Köfler apparatus)
mass spectrum: EI m/z=290 M+; m/z=226 (M-SO$_2$)+·; m/z=155 C$_7$H$_7$O$_2$S+; m/z=91C$_7$H$_7$+ base peak Stage 7(e): 5-fluoro-1-(toluene-4-sulfonyl)-2-tributylstannanyl-1H-pyrrolo[2,3-b]pyridine 5-Fluoro-1-(toluene-4-sulfonyl)-2-tributylstannanyl-1H-pyrrolo[2,3-b]pyridine can be prepared as in example 1 stage 1(k) but starting from 2 g of 5-fluoro-1-(toluene-4-sulfonyl)-1H-pyrrolo[2,3-b]pyridine, 2.58 g of tributyltin chloride, 4.95 cm³ of a 1.6M solution of n-butyllithium in hexane in 100 cm³ of tetrahydrofuran. In this way, after flash chromatography on a silica column [eluent: cyclohexane/ethyl acetate (95/5 by volume)], 2.70 g of 5-fluoro-1-(toluene-4-sulfonyl)-2-tributylstannanyl-1H-pyrrolo[2,3-b]pyridine is obtained as an oil with the following characteristics:

Rf TLC silica [eluent: cyclohexane/ethyl acetate/triethylamine (95/5/1 by volume)]=0.41
$^1$H NMR spectrum (400 MHz)—δ—in ppm—in DMSO-d6: 0.89 (t, J=7.0 Hz, 9H); from 1.15 to 1.70 (m, 18H); 2.37 (s, 3H); 6.87 (m, 1H); 7.43 (d broad, J=8.5 Hz, 2H); 7.86 (d broad, J=8.5 Hz, 2H); 7.90 (dd, J=3.0 and 9.0 Hz, 1H); 8.26 (dd, J=1.5 and 3.0 Hz, 1H).
Mass spectrum: MS-EI: 579(+)=M(+)

Stage 7(f): Tert-butyl 3-[5-fluoro-1-(toluene-4-sulfonyl)-1H-pyrrolo[2,3-b]pyridin-2-yl]-5,6-dimethoxy-pyrrolo[3,2-b]pyridine-1-carboxylate Tert-butyl 3-[5-fluoro-1-(toluene-4-sulfonyl)-1H-pyrrolo[2,3-b]pyridin-2-yl]-5,6-dimethoxy-pyrrolo[3,2-b]pyridine-1-carboxylate can be prepared as in example 1 stage 1(l) but starting from 1.30 g of 5-fluoro-1-(toluene-4-sulfonyl)-2-tributylstannanyl-1H-pyrrolo[2,3-b]pyridine, 0.73 g of tert-butyl 3-bromo-5,6-dimethoxy-pyrrolo[3,2-b]pyridine-1-carboxylate, 0.039 g of copper iodide, and 0.236 g of palladium tetrakis(triphenylphosphine) in 60 cm³ of toluene. In this way, after flash chromatography on a silica column [eluent: cyclohexane/ethyl acetate (70/30 by volume)], 0.48 g of tert-butyl 3-[5-fluoro-1-(toluene-4-sulfonyl)-1H-pyrrolo[2,3-b]pyridin-2-yl]-5,6-dimethoxy-pyrrolo[3,2-b]pyridine-1-carboxylate is obtained as a meringue with the following characteristics:

Rf TLC silica [eluent: cyclohexane/ethyl acetate (50/50 by volume)]=0.39
$^1$H NMR spectrum (300 MHz)—δ in ppm—in DMSO-d6: 1.71 (s, 9H); 2.33 (s, 3H); 3.87 (s, 3H); 3.92 (s, 3H); 7.03 (s, 1H); 7.34 (d broad, J=8.5 Hz, 2H); 7.76 (d broad, J=8.5 Hz, 2H); 7.91 (s, 1H); 7.96 (dd, J=2.5 and 8.5 Hz, 1H); 8.02 (s, 1H); 8.36 (dd, J=1.5 and 2.5 Hz, 1H).

Stage 7(g): 3-[5-fluoro-1-(toluene-4-sulfonyl)-1H-pyrrolo[2,3-b]pyridin-2-yl]-5,6-dimethoxy-1H-pyrrolo[3,2-b]pyridine 3-[5-Fluoro-1-(toluene-4-sulfonyl)-1H-pyrrolo[2,3-b]pyridin-2-yl]-5,6-dimethoxy-1H-pyrrolo[3,2-b]pyridine can be prepared as in example 1 stage 1(m) but starting from 0.78 g of tert-butyl 3-[5-fluoro-1-(toluene-4-sulfonyl)-1H-pyrrolo[2,3-b]pyridin-2-yl]-5,6-dimethoxy-pyrrolo[3,2-b]pyridine-1-carboxylate, and 10 cm³ of trifluoroacetic acid in 45 cm³ of dichloromethane. In this way, after flash chromatography on a silica column [eluent: dichloromethane/ethyl acetate (95/5 by volume)], 0.40 g of 3-[5-fluoro-1-(toluene-4-sulfonyl)-1H-pyrrolo[2,3-b]pyridin-2-yl]-5,6-dimethoxy-1H-pyrrolo[3,2-b]pyridine is obtained as a solid with the following characteristics:

Rf TLC silica [eluent: dichloromethane/ethyl acetate (90/10 by volume)]=0.29
$^1$H NMR spectrum (300 MHz)—δ in ppm—in DMSO-d6: 2.31 (s, 3H); 3.86 (s, 3H); 3.88 (s, 3H); 6.98 (s, 1H); 7.28 (d broad, J=8.5 Hz, 2H); 7.40 (s broad, 1H); 7.67 (m, 3H); 7.86 (dd, J=3.0 and 8.5 Hz, 1H); 8.28 (dd, J=1.5 and 3.0 Hz, 1H); 11.4 (s broad, 1H).
Mass spectrum: MS-EI: 466(+)=M(+)

Stage 7(h): 1-(2-chloroethyl)-3-[5-fluoro-1-(toluene-4-sulfonyl)-1H-pyrrolo[2,3-b]pyridin-2-yl]-5,6-dimethoxy-1H-pyrrolo[3,2-b]pyridine 1-(2-Chloroethyl)-3-[5-fluoro-1-(toluene-4-sulfonyl)-1H-pyrrolo[2,3-b]pyridin-2-yl]-5,6-dimethoxy-1H-pyrrolo[3,2-b]pyridine can be prepared as in example 2 stage 2(a) but starting from 0.40 g of 3-[5-fluoro-1-(toluene-4-sulfonyl)-1H-pyrrolo[2,3-b]pyridin-2-yl]-5,6-dimethoxy-1H-pyrrolo[3,2-b]pyridine, 0.0055 g of tetrabutylammonium bromide, 0.32 g of potassium hydroxide and 0.276 g of potassium carbonate in 30 cm³ of 1,2-dichloroethane. In this way, 0.45 g of 1-(2-chloro-ethyl)-3-[5-fluoro-1-(toluene-4-sulfonyl)-1H-pyrrolo[2,3-b]pyridin-2-yl]-5,6-dimethoxy-1H-pyrrolo[3,2-b]pyridine is obtained as a meringue with the following characteristics:

Rf TLC silica [eluent: dichloromethane/ethyl acetate (90/10 by volume)]=0.68
$^1$H NMR spectrum (300 MHz)—δ in ppm—in DMSO-d6: 2.31 (s, 3H); 3.87 (s, 3H); 3.90 (s, 3H); 4.08 (t, J=6.0 Hz, 2H); 4.65 (t, J=6.0 Hz, 2H); 6.97 (s, 1H); 7.27 (d broad, J=8.5 Hz, 2H); 7.67 (d broad, J=8.5 Hz, 2H); 7.71 (s, 1H); 7.77 (s, 1H); 7.87 (dd, J=3.0 and 9.0 Hz, 1H); 8.30 (dd, J=1.5 and 3.0 Hz, 1H).
Mass spectrum: MS-EI: 528(+)/ . . . =M(+)/ . . . (1 Cl present)

Stage 7(i): 3-[5-fluoro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine 3-[5-Fluoro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine can be prepared as in example 2 stage 2(b) but starting from 0.45 g of 1-(2-chloro-ethyl)-3-[5-fluoro-1-(toluene-4-sulfonyl)-1H-pyrrolo[2,3-b]pyridin-2-yl]-5,6-dimethoxy-1H-pyrrolo[3,2-b]pyridine and 0.19 g of sodium iodide in 40 cm³ of 2-butanone. In this way, 0.53 g of 3-[5-fluoro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine is obtained as a meringue with the following characteristics:

Rf TLC silica [eluent: dichloromethane/ethyl acetate (95/5 by volume)]=0.48
$^1$H NMR spectrum (300 MHz)—δ in pp—in DMSO-d6: 2.31 (s, 3H); 3.68 (t, J=6.5 Hz, 2H); 3.87 (s, 3H); 3.90 (s, 3H); 4.65 (t, J=6.5 Hz, 2H); 6.96 (s, 1H); 7.28 (d broad, J=8.5 Hz, 2H); 7.68 (d broad, J=8.5 Hz, 2H); 7.71 (s, 1H); 7.79 (s, 1H); 7.88 (dd broad, J=3.0 and 8.5 Hz, 1H); 8.31 (m, 1H).

Mass spectrum: MS-EI: 620(+)=M(+)

Stage 7(j): 3-[5-fluoro-1-(toluene-4-sulfonyl)-1H-pyrrolo[2,3-b]pyridin-2-yl]-5,6-dimethoxy-1-(2-morpholin-4-ylethyl)-1H-pyrrolo[3,2-b]pyridine 3-[5-Fluoro-1-(toluene-4-sulfonyl)-1H-pyrrolo[2,3-b]pyridin-2-yl]-5,6-dimethoxy-1-(2-morpholin-4-yl-ethyl)-1H-pyrrolo[3,2-b]pyridine can be prepared as in example 2 stage 2(c) but starting from 0.53 g of 3-[5-fluoro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine, 0.13 g of potassium carbonate and 0.150 g of morpholine in 60 cm$^3$ of acetonitrile. In this way, 0.47 g of 3-[5-fluoro-1-(toluene-4-sulfonyl)-1H-pyrrolo[2,3-b]pyridin-2-yl]-5,6-dimethoxy-1-(2-morpholin-4-yl-ethyl)-1H-pyrrolo[3,2-b]pyridine is obtained as a resin with the following characteristics:

Rf TLC silica [eluent: dichloromethane/methanol (95/5 by volume)]=0.52

$^1$H NMR spectrum (400 MHz)—δ in ppm—in DMSO-d6: 2.30 (s, 3H); 2.49 (m partially masked, 4H); 2.76 (t, J=6.0 Hz, 2H); 3.57 (m, 4H); 3.87 (s, 3H); 3.89 (s, 3H); 4.38 (t, J=6.0 Hz, 2H); 6.97 (s broad, 1H); 7.24 (d broad, J=8.5 Hz, 2H); 7.63 (m, 3H); 7.76 (s, 1H); 7.87 (dd broad, J=3.0 and 9.5 Hz, 1H); 8.29 (dd, J=2.0 and 3.0 Hz, 1H).

Stage 7(k): 3-(5-fluoro-1H-pyrrolo[2,3-b]pyridin-2-yl)-5,6-dimethoxy-1-(2-morpholin-4-ylethyl)-1H-pyrrolo[3,2-b]pyridine 3-(5-Fluoro-1H-pyrrolo[2,3-b]pyridin-2-yl)-5,6-dimethoxy-1-(2-morpholin-4-ylethyl)-1H-pyrrolo[3,2-b]pyridine can be prepared as in example 2 stage 2(d) but starting from 0.470 g of 3-[5-fluoro-1-(toluene-4-sulfonyl)-1H-pyrrolo[2,3-b]pyridin-2-yl]-5,6-dimethoxy-1-(2-morpholin-4-ylethyl)-1H-pyrrolo[3,2-b]pyridine, and 1 g of potassium hydroxide in 100 cm$^3$ of methanol. In this way, after flash chromatography on a silica column [eluent: dichloromethane/methanol (98/2 by volume)], 0.180 g of 3-(5-fluoro-1H-pyrrolo[2,3-b]pyridin-2-yl)-5,6-dimethoxy-1-(2-morpholin-4-yl-ethyl)-1H-pyrrolo[3,2-b]pyridine is obtained as a solid with the following characteristics:

melting point: melting at 218° C. (Köfler apparatus)

$^1$H NMR spectrum (400 MHz)—δ in ppm—in DMSO-d6: 2.47 (m, 4H); 2.71 (t, J=6.5 Hz, 2H); 3.58 (m, 4H); 3.89 (s, 3H); 4.07 (s, 3H); 4.33 (t, J=6.5 Hz, 2H); 7.22 (d, J=2.0 Hz, 1H); 7.65 (s, 1H); 7.75 (dd, J=2.5 and 9.5 Hz, 1H); 8.03 (s, 1H); 8.06 (dd, J=1.5 and 2.5 Hz, 1H); 11.85 (s broad, 1H).

Mass spectrum: MS-EI: 425(+)=M(+)

EXAMPLE 8

3-(4-chloro-5-fluoro-1H-pyrrolo[2,3-b]pyridin-2-yl)-5,6-dimethoxy-1-(2-morpholin-4-yl-ethyl)-1H-pyrrolo[3,2-b]pyridine Stage 8(a): 5-fluoro-1H-pyrrolo[2,3-b]pyridine 7-oxide 5-Fluoro-1H-pyrrolo[2,3-b]pyridine 7-oxide can be obtained as in example 4 stage 4(a) but starting from 2.7 g of 5-fluoro-1H-pyrrolo[2,3-b]pyridine, and 6.22 g of 3-chloro-perbenzoic acid in 70 cm$^3$ of dimethoxyethane. In this way, after flash chromatography on a silica column [eluent: dichloromethane/methanol (95/5 by volume)], 1.70 g of 5-fluoro-1H-pyrrolo[2,3-b]pyridine 7-oxide is obtained as a powder with the following characteristics:

melting point: melting at 178° C. (Köfler apparatus)

IR spectrum: KBr 3128; 3085; 2919; 2863; 2734; 2629; 2406; 1588; 1507; 1349; 1256; 1206; 1129; 1077; 990; 804; 723; 670 and 466 cm$^{-1}$ Stage 8(b): 4-chloro-5-fluoro-1H-pyrrolo[2,3-b]pyridine 4-Chloro-5-fluoro-1H-pyrrolo[2,3-b]pyridine can be obtained as in example 4 stage 4(b) but starting from 1.7 g of 5-fluoro-1H-pyrrolo[2,3-b]pyridine 7-oxide in 10 cm$^3$ of phosphorus oxychloride. In this way, 1.3 g of 4-chloro-5-fluoro-1H-pyrrolo[2,3-b]pyridine is obtained as a solid with the following characteristics:

Rf TLC silica [eluent: dichloromethane/methanol (98/2 by volume)]=0.19

$^1$H NMR spectrum (300 MHz)—δ in ppm—in DMSO-d6: 6.56 (m, 1H); 7.70 (m, 1H); 8.35 (d, J=2.5 Hz, 1H); 12.15 (m broad, 1H)

Mass spectrum: MS-EI:170(+)=M(+)

Stage 8c: 4-chloro-5-fluoro-1-(toluene-4-sulfonyl)-1H-pyrrolo[2,3-b]pyridine

4-Chloro-5-fluoro-1-(toluene-4-sulfonyl)-1H-pyrrolo[2,3-b]pyridine can be prepared as in example 7 stage 7(d) but starting from 1.30 g of 4-chloro-5-fluoro-1H-pyrrolo[2,3-b]pyridine, 1.60 g of 4-methyl-benzenesulfonyl chloride, 3.40 g of sodium hydroxide dissolved in 16 cm$^3$ of water, and 0.052 g of tetrabutylammonium hydrogen sulfate in 200 cm$^3$ of toluene. In this way, after flash chromatography on a silica column [eluent: dichloromethane], 1.90 g of 4-chloro-5-fluoro-1-(toluene-4-sulfonyl)-1H-pyrrolo[2,3-b]pyridine is obtained as a powder with the following characteristics:

melting point: melting at 125° C. (Köfler apparatus)

$^1$H NMR spectrum (300 MHz)—δ in ppm—in DMSO-d6: 2.36 (s, 3H); 6.93 (d, J=3.0 Hz, 1H); 7.44 (d broad, J=8.0 Hz, 2H); 7.99 (d broad, J=8.0 Hz, 2H); 8.12 (d, J=3.0 Hz, 1H); 8.52 (d, J=2.5 Hz, 1H)

Mass spectrum: MS-EI:324(+)=M(+)

Stage 8(d): 4-chloro-5-fluoro-1-(toluene-4-sulfonyl)-2-tributylstannanyl-1H-pyrrolo[2,3-b]pyridine 4-Chloro-5-fluoro-1-(toluene-4-sulfonyl)-2-tributylstannanyl-1H-pyrrolo[2,3-b]pyridine can be prepared as in example 7 stage 7(e) but starting from 3.8 g of 4-chloro-5-fluoro-1-(toluene-4-sulfonyl)-1H-pyrrolo[2,3-b]pyridine, 3.65 cm$^3$ of chloride of tributyltin, 7.92 cm$^3$ of a 1.6M solution of tert-butyllithium in hexane in 100 cm$^3$ of tetrahydrofuran. In this way, after flash chromatography on a silica column [eluent: cyclohexane/ethyl acetate (95/5 by volume)], 5.66 g of 4-chloro-5-fluoro-1-(toluene-4-sulfonyl)-2-tributylstannanyl-1H-pyrrolo[2,3-b]pyridine is obtained as an oil with the following characteristics:

Rf TLC silica [eluent: cyclohexane/ethyl acetate (75/25 by volume)]=0.73

$^1$H NMR spectrum (300 MHz)—δ in ppm—in DMSO-d6: 0.88 (t, J=7.5 Hz, 9H); from 1.10 to 1.70 (m, 18H); 2.35 (s, 3H); 6.82 (m, 1H); 7.43 (d broad, J=8.0 Hz, 2H); 7.84 (d broad, J=8.0 Hz, 2H); 8.39 (d, J=2.5 Hz, 1H)

Mass spectrum: MS-EI:614(+)=M(+)

Stage 8(e): Tert-butyl 3-[4-chloro-5-fluoro-1-(toluene-4-sulfonyl)-1H-pyrrolo[2,3-b]pyridin-2-yl]-5,6-dimethoxypyrrolo[3,2-b]pyridine-1-carboxylate Tert-butyl 3-[4-chloro-5-fluoro-1-(toluene-4-sulfonyl)-1H-pyrrolo[2,3-b]pyridin-2-yl]-5,6-dimethoxy-pyrrolo[3,2-b]pyridine-1-carboxylate can be prepared as in example 7 stage 7(f) but starting from 5.20 g of 4-chloro-5-fluoro-1-(toluene-4-sulfonyl)-2-tributylstannanyl-1H-pyrrolo[2,3-b]pyridine, 3.10 g of tert-butyl 3-bromo-5,6-dimethoxypyrrolo[3,2-b]pyridine-1-carboxylate, 0.146 g of copper iodide, and 0.889 g of palladium tetrakis(triphenylphosphine) in 160 cm$^3$ of toluene. In this way, after flash chromatography on a silica column [eluent: cyclohexane/ethyl acetate (75/25 by volume)], 3.30 g of tert-butyl 3-[4-chloro-5-fluoro-1-(toluene-4-sulfonyl)-1H-pyrrolo[2,3-b]pyridin-2-yl]-5,6-dimethoxy-pyrrolo[3,2-b]pyridine-1-carboxylate is obtained as a solid with the following characteristics:

Rf TLC silica [eluent: cyclohexane/ethyl acetate (75/25 by volume)]=0.32

$^1$H NMR spectrum (300 MHz)—δ in ppm—in DMSO-d6: 1.71 (s, 9H); 2.32 (s, 3H); 3.85 (s, 3H); 3.90 (s, 3H); 7.13 (s, 1H); 7.34 (d broad, 2H); 7.79 (d broad, J=8.0 Hz, 2H); 7.90 (s, 1H); 8.09 (s, 1H); 8.49 (d, J=2.5 Hz, 1H)

Mass spectrum: MS-EI:600(+)=M(+)

Stage 8(f): 3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine 3-[4-Chloro-5-fluoro-1-(toluene-4-sulfonyl)-1H-pyrrolo[2,3-b]pyridin-2-yl]-5,6-dimethoxy-1H-pyrrolo[3,2-b]pyridine can be prepared as in example 7 stage 7(g) but starting from 3.2 g of tert-butyl 3-[4-chloro-5-fluoro-1-(toluene-4-sulfonyl)-1H-pyrrolo[2,3-b]pyridin-2-yl]-5,6-dimethoxy-pyrrolo[3,2-b]pyridine-1-carboxylate, and 30 cm$^3$ of trifluoroacetic acid in 150 cm$^3$ of dichloromethane. In this way, 2.50 g of 3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine is obtained as a solid with the following characteristics:

Rf TLC silica [eluent: cyclohexane/ethyl acetate (50/50 by volume)]=0.34.

$^1$H NMR spectrum (300 MHz)—δ in ppm—in DMSO-d6: 2.31 (s, 3H); 3.86 (s, 3H); 3.88 (s, 3H); 7.07 (s, 1H); 7.30 (d broad, J=8.5 Hz, 2H); 7.39 (s, 1H); 7.70 (d broad, J=8.5 Hz, 2H); 7.73 (s, 1H); 8.41 (d, J=2.5 Hz, 1H); 11.45 (s broad, 1H)

Mass spectrum: MS-EI:501(+)=M(+)

Stage 8(g): 1-(2-chloroethyl)-3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine 1-(2-Chloroethyl)-3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine can be prepared as in example 7 stage 7(h) but starting from 0.50 g of 3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine, 0.0065 g of tetrabutylammonium bromide, 0.44 g of potassium hydroxide and 0.32 g of potassium carbonate in 50 cm$^3$ of 1,2-dichloroethane. In this way, 0.56 g of 1-(2-chloro-ethyl)-3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine is obtained as a solid with the following characteristics:

RfTLC silica [eluent: cyclohexane/ethyl acetate (90/10 by volume)]=0.43

$^1$H NMR spectrum (400 MHz)—δ in ppm—in DMSO-d6: 2.30 (s, 3H); 3.86 (s, 3H); 3.89 (s, 3H); 4.07 (t, J=6.0 Hz, 2H); 4.64 (t, J=6.0 Hz, 2H); 7.06 (s, 1H); 7.29 (d broad, J=8.0 Hz, 2H); from 7.68 to 7.73 (m, 3H); 7.85 (s, 1H); 8.45 (d, J=2.5 Hz, 1H)

Mass spectrum: MS-EI:562(+)=M(+)

Stage 8(h): 3-[4-chloro-5-fluoro-1-(toluene-4-sulfonyl)-1H-pyrrolo[2,3-b]pyridin-2-yl]-1-(2-iodo-ethyl)-5,6-dimethoxy-1H-pyrrolo[3,2-b]pyridine 3-[4-Chloro-5-fluoro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine can be prepared as in example 7 stage 7(i) but starting from 0.56 g of 1-(2-chloroethyl)-3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine and 0.22 g of sodium iodide in 80 cm$^3$ of 2-butanone. In this way, 0.36 g of 3-[4-chloro-5-fluoro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine is obtained as a solid with the following characteristics:

Rf TLC silica [eluent: cyclohexane/ethyl acetate (98/2 by volume)]=0.44

$^1$H NMR spectrum (300 MHz)—δ in ppm—in DMSO-d6: 2.30 (s, 3H); 3.67 (t, J=6.0 Hz, 2H); 3.86 (s, 3H); 3.89 (s, 3H); 4.64 (t, J=6.0 Hz, 2H); 7.03 (s, 1H); 7.30 (d broad, J=9.0 Hz, 2H); from 7.67 to 7.73 (m, 3H); 7.84 (s, 1H); 8.43 (d, J=2.5 Hz, 1H)

Mass spectrum: MS-EI:654(+)=M(+)

Stage 8(i): 3-[4-chloro-5-fluoro-1-(toluene-4-sulfonyl)-1H-pyrrolo[2,3-b]pyridin-2-yl]-5,6-dimethoxy-1-(2-morpholin-4-ylethyl)-1H-pyrrolo[3,2-b]pyridine 3-[4-Chloro-5-fluoro-1-(toluene-4-sulfonyl)-1H-pyrrolo[2,3-b]pyridin-2-yl]-5,6-dimethoxy-1-(2-morpholin-4-ylethyl)-1H-pyrrolo[3,2-b]pyridine can be prepared as in example 7 stage 7(j) but starting from 0.35 g of 3-[4-chloro-5-fluoro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine, 0.082 g of potassium carbonate and of 0.093 g of morpholine in 44 cm$^3$ of acetonitrile. In this way, after flash chromatography on a silica column [eluent: dichloromethane/methanol (98/2 by volume)], 0.22 g of 3-[4-chloro-5-fluoro-1-(toluene-4-sulfonyl)-1H-pyrrolo[2,3-b]pyridin-2-yl]-5,6-dimethoxy-1-(2-morpholin-4-ylethyl)-1H-pyrrolo[3,2-b]pyridine is obtained as a resin with the following characteristics:

Rf TLC silica [eluent: dichloromethane/methanol (98/2 by volume)]=0.16

$^1$H NMR spectrum (300 MHz)—δ in ppm—in DMSO-d6: 2.30 (s, 3H); from 2.45 to 2.55 (m masked, 4H); 2.76 (m, 2H); 3.55 (m, 4H); 3.83 (s, 3H); 3.89 (s, 3H); 4.38 (m, 2H); 7.07 (s, 1H); 7.28 (d broad, J=8.0 Hz, 2H); from 7.62 to 7.69 (m, 3H); 7.83 (s, 1H); 8.42 (d, J=2.5 Hz, 1H)

Mass spectrum: MS-EI:613(+)=M(+)

Stage 8(j): 3-(4-chloro-5-fluoro-1H-pyrrolo[2,3-b]pyridin-2-yl)-5,6-dimethoxy-1-(2-morpholin-4-ylethyl)-1H-pyrrolo[3,2-b]pyridine 3-(4-Chloro-5-fluoro-1H-pyrrolo(2,3-b)pyridin-2-yl)-5,6-dimethoxy-1-(2-morpholin-4-ylethyl)-1H-pyrrolo[3,2-b]pyridine can be prepared as in example 7 stage 7(k) but starting from 0.220 g of 3-[4-chloro-5-fluoro-1-(toluene-4-sulfonyl)-1H-pyrrolo[2,3-b]pyridin-2-yl]-5,6-dimethoxy-1-

(2-morpholin-4-ylethyl)-1H-pyrrolo[3,2-b]pyridine, and 0.52 g of potassium hydroxide in 40 cm³ of methanol. In this way, after flash chromatography on a silica column [eluent: dichloromethane/methanol (98/2 by volume)], 0.128 g of 3-(4-chloro-5-fluoro-1H-pyrrolo[2,3-b]pyridin-2-yl)-5,6-dimethoxy-1-(2-morpholin-4-ylethyl)-1H-pyrrolo[3,2-b]pyridine is obtained as a solid with the following characteristics:

melting point: melting at 206° C. (Köfler apparatus)

$^1$H NMR spectrum (300 MHz)—δ in ppm—in DMSO-d6: 2.47 (m, partially masked, 4H); 2.72 (t, J=6.0 Hz, 2H); 3.58 (m, 4H); 3.88 (s, 3H); 4.06 (s, 3H); 4.33 (t, J=6.0 Hz, 2H); 7.28 (s, 1H); 7.67 (s, 1H); 8.05 (s, 1H); 8.19 (d, J=2.5 Hz, 1H); 12.2 (m broad, 1H)

Mass spectrum: MS-EI:459(+)=M(+)

EXAMPLE 9

3-[4-Chloro-5-fluoro-1H-pyrrolo[2,3-b]pyridin-2-yl]-5,6-dimethoxy-1H-pyrrolo[3,2-b]pyridine A suspension of 0.2 g of 3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine and 0.580 g of potassium hydroxide in 40 cm³ of methanol is refluxed for about 5 hours. After concentrating under reduced pressure (13 kPa), the solid is taken up in 50 cm³ of water, filtered off by suction and washed with 10 cm³ of water. After recrystallization from 40 cm³ of acetonitrile, 0.110 g of 3-[4-chloro-5-fluoro-1H-pyrrolo[2,3-b]pyridin-2-yl]-5,6-dimethoxy-1H-pyrrolo[3,2-b]pyridine is obtained as a solid with the following characteristics:

melting point: melting at 283-284° C. (Buchï)

$^1$H NMR spectrum (300 MHz)—δ in ppm—in DMSO-d6: 3.83 (s, 3H); 4.03 (s, 3H); 7.30 (s, 1H); 7.41 (broad s, 1H); 8.02 (s, 1H); 8.18 (d, J=2.5 Hz, 1H); 11.4 (very broad m, 1H); 12.15 (broad m, 1H).

Mass spectrum: ES m/z=347 MH⁺ base peak

EXAMPLE 10

3-(4-Chloro-5-fluoro-1H-pyrrolo[2,3-b]pyridin-2-yl)-5,6-dimethoxy-1-[2-(4-methylpiperazin-1-yl)ethyl]-1H-pyrrolo[3,2-b]pyridine Stage 10(a): 3-[4-Chloro-5-fluoro-1-(toluene-4-sulfonyl)-1H-pyrrolo[2,3-b]pyridin-2-yl]-5,6-dimethoxy-1-[2-(4-methylpiperazin-1-yl)-ethyl]-1H-pyrrolo[3,2-b]pyridine 3-[4-Chloro-5-fluoro-1-(toluene-4-sulfonyl)-1H-pyrrolo[2,3-b]pyridin-2-yl]-5,6-dimethoxy-1-[2-(4-methylpiperazin-1-yl)ethyl]-1H-pyrrolo[3,2-b]pyridine can be prepared as in example 2 stage 2(c), but starting with 0.18 g of 3-[4-chloro-5-fluoro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine, 0.042 g of potassium carbonate and 0.055 g of 1-methylpiperazine in 25 cm³ of acetonitrile. After flash chromatography on a column of silica [eluent: dichloromethane/methanol (95/5 by volume)], 0.065 g of 3-[4-chloro-5-fluoro-1-(toluene-4-sulfonyl)-1H-pyrrolo[2,3-b]pyridin-2-yl]-5,6-dimethoxy-1-[2-(4-methylpiperazin-1-yl)ethyl]-1H-pyrrolo[3,2-b]pyridine is thus obtained as a resin with the following characteristics:

Rf TLC silica [eluent: dichloromethane/methanol (95/5 by volume)]=0.084

Mass spectrum: ES m/z=627 MH⁺

Stage 10(b): 3-(4-Chloro-5-fluoro-1H-pyrrolo[2,3-b]pyridin-2-yl)-5,6-dimethoxy-1-[2-(4-methylpiperazin-1-yl)ethyl]-1H-pyrrolo[3,2-b]pyridine 3-(4-Chloro-5-fluoro-1H-pyrrolo[2,3-b]pyridin-2-yl-5,6-dimethoxy-1-[2-(4-methylpiperazin-1-yl)ethyl]-1H-pyrrolo[3,2-b]pyridine can be prepared as in example 2, stage 2(d), but starting with 0.065 g of 3-[4-chloro-5-fluoro-1-(toluene-4-sulfonyl)-1H-pyrrolo[2,3-b]pyridin-2-yl]-5,6-dimethoxy-1-[2-(4-methylpiperazin-1-yl)ethyl]-1H-pyrrolo[3,2-b]pyridine and 0.116 g of potassium hydroxide in 25 cm³ of methanol. After flash chromatography on a column of silica [eluent: dichloromethane/methanol (90/10 by volume)], 0.030 g of 3-(4-chloro-5-fluoro-1H-pyrrolo[2,3-b]pyridin-2-yl)-5,6-dimethoxy-1-[2-(4-methylpiperazin-1-yl)ethyl-1H-pyrrolo[3,2-b]pyridine is thus obtained as a solid with the following characteristics:

Rf TLC silica [eluent: dichloromethane/methanol (90/10 by volume)]=0.15

$^1$H NMR spectrum (300 MHz)—δ in ppm—in DMSO-d6: 2.13 (s, 3H); 2.29 (broad m, 4H); from 2.42 to 2.55 (partially masked m, 4H); 2.70 (broad t, J=6.5 Hz, 2H); 3.88 (s, 3H); 4.05 (s, 3H); 4.31 (broad t, J=6.5 Hz, 2H); 7.26 (broad s, 1H); 7.65 (s, 1H); 8.04 (s, 1H); 8.18 (d, J=2.5 Hz, 1H); 12.15 (broad s, 1H)

Mass spectrum: IE m/z=472 M⁺; m/z=113 $C_6H_{13}N_2^+$ base peak; m/z=70 $C_4H_8N^+$

EXAMPLE 11

3-[4-Chloro-5-fluoro-1H-pyrrolo[2,3-b]pyridin-2-yl]-5,6-dimethoxy-1-(3-piperidin-1-ylpropyl)-1H-pyrrolo[3,2-b]pyridine Stage 11(a): 3-[4-Chloro-5-fluoro-1-(toluene-4-sulfonyl)-1H-pyrrolo[2,3-b]pyridin-2-yl]-1-(3-chloropropyl)-5,6-dimethoxy-1H-pyrrolo[3,2-b]pyridine 3-[4-Chloro-5-fluoro-1-(toluene-4-sulfonyl)-1H-pyrrolo[2,3-b]pyridin-2-yl]-1-(3-chloropropyl)-5,6-dimethoxy-1H-pyrrolo[3,2-b]pyridine can be prepared as in example 2, stage 2(a), but starting with 1.8 g of 3-[4-chloro-5-fluoro-1-(toluene-4-sulfonyl)-1H-pyrrolo[2,3-b]pyridin-2-yl]-5,6-dimethoxy-1H-pyrrolo[3,2-b]pyridine, 0.046 g of tetrabutylammonium bromide, 1.34 g of potassium hydroxide and 1.16 g of potassium carbonate in 150 cm³ of 1-bromo-3-chloropropane. 2 g of 3-[4-chloro-5-fluoro-1-(toluene-4-sulfonyl)-1H-pyrrolo[2,3-b]pyridin-2-yl]-1-(3-chloropropyl)-5,6-dimethoxy-1H-pyrrolo[3,2-b]pyridine are thus obtained as a resin with the following characteristics:

Rf TLC silica [eluent: cyclohexane/ethyl acetate (50/50 by volume)]=0.63

Mass spectrum: ES m/z=577 MH⁺ base peak

Stage 11(b): 3-[4-Chloro-5-fluoro-1-(toluene-4-sulfonyl)-1H-pyrrolo[2,3-b]pyridin-2-yl]-1-(3-iodopropyl)-5,6-dimethoxy-1H-pyrrolo[3,2-b]pyridine 3[4-Chloro-5-fluoro-1-(toluene-4-sulfonyl)-1H-pyrrolo[2,3-b]pyridin-2-yl]-1-(3-iodopropyl)-5,6-dimethoxy-1H-pyrrolo[3,2-b]pyridine can be prepared as in example 2, stage 2(b), but starting with 2.07 g of 3-[4-(chloro-5-fluoro-1-(toluene-4-sulfonyl)-1H-pyrrolo[2,3-b]pyridin-2-yl]-1-(3-chloropropyl)-5,6-dimethoxy-1H-pyrrolo[3,2-b]pyridine and 1.07 g of sodium iodide in 150 cm³ of 2-butanone. 2.3 g of 3-[4-chloro-5-fluoro-1-(toluene-4-sulfonyl)-1H-pyrrolo[2, 3-b]pyridin-2-yl]-1-(3-iodopropyl)-5,6-dimethoxy-1H-pyrrolo[3,2-b]pyridine are thus obtained as a resin with the following characteristics:

Rf TLC silica [eluent: cyclohexane/ethyl acetate (50/50 by volume)]=0.67

Mass spectrum: IE m/z=668 $M^+$ base peak; m/z=513 $(M-C_7H_7SO_2)^+$; m/z=386 $(m/z=513-I)^+$.

Stage 11(c): 3-[4-Chloro-5-fluoro-1-(toluene-4-sulfonyl)-1H-pyrrolo[2,3-b]pyridin-2-yl]-5,6-dimethoxy-(3-piperidin-1-ylpropyl)-1H-pyrrolo[3,2-b]pyridine 3-[4-Chloro-5-fluoro-1-(toluene-4-sulfonyl)-1H-pyrrolo[2,3-b]pyridin-2-yl]-5,6-dimethoxy-(3-piperidin-1-ylpropyl)-1H-pyrrolo[3,2-b]pyridine can be prepared in the following manner:

a solution of 0.3 g of 3-[4-chloro-5-fluoro-1-(toluene-4-sulfonyl)-1H-pyrrolo[2,3-b]pyridin-2-yl]-1-(3-iodopropyl)-5,6-dimethoxy-1H-pyrrolo[3,2-b]pyridine and 0.382 g of piperidine in 40 $cm^3$ of dichloromethane is refluxed for about 6 hours. After diluting the reaction mixture with 100 $cm^3$ of dichloromethane, the solution is washed with three times 40 $cm^3$ of water, dried over magnesium sulfate, filtered and concentrated to dryness under reduced pressure (13 kPa). After flash chromatography on a column of silica [eluent: dichloromethane/methanol (98/2 by volume)], 0.175 g of 3-[4-chloro-5-fluoro-1-(toluene-4-sulfonyl)-1H-pyrrolo[2,3-b]pyridin-2-yl]-5,6-dimethoxy-(3-piperidin-1-ylpropyl)-1H-pyrrolo[3,2-b]pyridine is thus obtained as a resin with the following characteristics:

Rf TLC silica [eluent: dichloromethane/methanol (90/10 by volume)]=0.26

Mass spectrum: ES m/z=626 $MH^+$ base peak

Stage 11(d): 3-[4-Chloro-5-fluoro-1H-pyrrolo[2,3-b]pyridin-2-yl]-5,6-dimethoxy-1-(3-piperidin-1-ylpropyl)-1H-pyrrolo[3,2-b]pyridine 3-[4-Chloro-5-fluoro-1H-pyrrolo[2,3-b]pyridin-2-yl]-5,6-dimethoxy-1-(3-piperidin-1-ylpropyl)-1H-pyrrolo[3,2-b]pyridine can be prepared as in example 2, stage 2(d), but starting with 0.175 g of 3-[4-chloro-5-fluoro-1-(toluene-4-sulfonyl)-1H-pyrrolo[2,3-b]pyridin-2-yl]-5,6-dimethoxy-(3-piperidin-1-ylpropyl)-1H-pyrrolo[3,2-b]pyridine and 0.314 g of potassium hydroxide in 40 $cm^3$ of methanol. After flash chromatography on a column of silica [eluent: dichloromethane/methanol (95/5 by volume)], 0.086 g of 3-[4-chloro-5-fluoro-1H-pyrrolo[2,3-b]pyridin-2-yl]-5,6-dimethoxy-1-(3-piperidin-1-ylpropyl)-1H-pyrrolo[3,2-b]pyridine is thus obtained as a solid with the following characteristics:

melting point: melting at 110-114° C. (Köfler block)

$^1$H NMR spectrum (300 MHz)—δ in ppm—in DMSO-d6: 1.37 (m, 2H); 1.50 (m, 4H); 1.95 (m, 2H); 2.20 (t, J=7.0 Hz, 2H); 2.28 (m, 4H); 3.88 (s, 3H); 4.05 (s, 3H); 4.24 (t, J=7.0 Hz, 2H); 7.26 (d, J=2.0 Hz, 1H); 7.59 (s, 1H); 8.04 (s, 1H); 8.18 (d, J=2.5 Hz, 1H); 12.1 (broad s, 1H).

Mass spectrum: IE m/z=471 $M^+$; m/z=360 $(M-C_7H_{13}N)^+$ base peak; m/z=98 $C_6H_{12}N^+$

EXAMPLE 12

1-{3-[3-(4-Chloro-5-fluoro-1H-pyrrolo[2,3-b]pyridin-2-yl)-5,6-dimethoxypyrrolo[3,2-b]pyridin-1-yl]propyl}piperidin-4-ol Stage 12(a): 1-(3-{3-[4-Chloro-5-fluoro-1-(toluene-4-sulfonyl)-1H-pyrrolo[2,3-b]pyridin-2-yl]-5,6-dimethoxy-pyrrolo[3,2-b]pyridin-1-yl}propyl)piperidin-4-ol 1-(3-{3-[4-Chloro-5-fluoro-1-(toluene-4-sulfonyl)-1H-pyrrolo[2,3-b]pyridin-2-yl]-5,6-dimethoxypyrrolo[3,2-b]pyridin-1-yl}propyl)piperidin-4-ol can be prepared as in example 11, stage 11(c), but starting with 0.300 g of 3-[4-chloro-5-fluoro-1-(toluene-4-sulfonyl)-1H-pyrrolo[2,3-b]pyridin-2-yl]-1-(3-iodopropyl)-5,6-dimethoxy-1H-pyrrolo[3,2-b]pyridine and 0.454 g of piperidin-4-ol in 40 $cm^3$ of dichloromethane. After flash chromatography on a column of silica [eluent: dichloromethane/methanol (95/5 by volume)], 0.178 g of 1-(3-{3-[4-chloro-5-fluoro-1-(toluene-4-sulfonyl)-1H-pyrrolo[2,3-b]pyridin-2-yl]-5,6-dimethoxy-pyrrolo[3,2-b]pyridin-1-yl}propyl)piperidin-4-ol is thus obtained as a meringue with the following characteristics:

Rf TLC silica [eluent: dichloromethane/methanol (90/10 by volume)]=0.14

Mass spectrum: ES m/z=642 $MH^+$ base peak

Stage 12(b): 1-{3-[3-(4-Chloro-5-fluoro-1H-pyrrolo[2,3-b]pyridin-2-yl)-5,6-dimethoxypyrrolo[3,2-b]pyridin-1-yl]propyl}piperidin-4-ol 1-{3-[3-(4-Chloro-5-fluoro-1H-pyrrolo[2,3-b]pyridin-2-yl)-5,6-dimethoxypyrrolo[3,2-b]pyridin-1-yl]propyl}piperidin-4-ol can be prepared as in example 2, stage 2(d), but starting with 0.178 g of 1-(3-{3-[4-chloro-5-fluoro-1-(toluene-4-sulfonyl)-1H-pyrrolo[2,3-b]pyridin-2-yl]-5,6-dimethoxypyrrolo[3,2-b]pyridin-1-yl}propyl)piperidin-4-ol and 0.31 g of potassium hydroxide in 40 $cm^3$ of methanol. After flash chromatography on a column of silica [eluent: dichloromethane/methanol (90/10 by volume)], 0.102 g of 1-{3-[3-(4-chloro-5-fluoro-1H-pyrrolo[2,3-b]pyridin-2-yl)-5,6-dimethoxypyrrolo[3,2-b]pyridin-1-yl]propyl}piperidin-4-ol is thus obtained as a solid with the following characteristics:

melting point: melting at 188° C. (Köfler block)

$^1$H NMR spectrum (300 MHz)—δ in ppm—in DMSO-d6: 1.41 (m, 2H); 1.71 (m, 2H); from 1.88 to 2.00 (m, 4H); 2.20 (t, J=6.5 Hz, 2H); 2.65 (m, 2H); 3.43 (m, 1H); 3.88 (s, 3H); 4.05 (s, 3H); 4.23 (t, J=6.5 Hz, 2H); 4.52 (d, J=4.0 Hz, 1H); 7.26 (d, J=2.0 Hz, 1H);7.59 (s, 1H); 8.03 (s, 1H); 8.18 (d, J=2.5 Hz, 1H); 12.15 (broad s, 1H).

Mass spectrum: IE m/z=487 $M^+$; m/z=360 $(M-C_7H_{13}NO)^+$ base peak; m/z=114 $C_6H_{12}NO^+$

EXAMPLE 13

3-(4-Chloro-5-fluoro-1H-pyrrolo[2,3-b]pyridin-2-yl)-5,6-dimethoxy-1-[3-(4-methylperhydro-1,4-diazepin-1-yl)propyl]-1H-pyrrolo[3,2-b]pyridine Stage 13(a): 3-[4-Chloro-5-fluoro-1-(toluene-4-sulfonyl)-1H-pyrrolo[2,3-b]pyridin-2-yl]-5,6-dimethoxy-1-[3-(4-methylperhydro-1,4-diazepin-1-yl)propyl]-1H-pyrrolo[3,2-b]-pyridine 3-[4-Chloro-5-fluoro-1-(toluene-4-sulfonyl)-1H-pyrrolo[2,3-b]pyridin-2-yl]-5,6-dimethoxy-1-[3-(4-methylperhydro-1,4-diazepin-1-yl)propyl]-1h-pyrrolo[3,2-b]pyridine can be prepared as in example 11, stage 11(c), but starting with 0.300 g of 3-[4-chloro-5-fluoro-1-(toluene-4-sulfonyl)-1H-pyrrolo[2,3-b]pyridin-2-yl]-1-(3-iodopropyl)-5,6-dimethoxy-1H-pyrrolo[3,2-b]pyridine and 0.512 g of 1-methylperhydro-1,4-diazepine in 40 cm$^3$ of dichloromethane. After flash chromatography on a column of silica [eluent: chloroform/methanol/28% aqueous ammonia (24/3/0.5 by volume)], 0.145 g of 3-[4-chloro-5-fluoro-1-(toluene-4-sulfonyl)-1H-pyrrolo[3,2-b]pyridin-2-yl]-5,6-dimethoxy-1-[3-(4-methylperhydro-1,4-diazepin-1-yl)propyl]-1H-pyrrolo[3,2-b]pyridine is thus obtained as a resin with the following characteristics:

Rf TLC silica [eluent: chloroform/methanol/28% aqueous ammonia (24/3/0.5 by volume)]=0.33

Mass spectrum: ES m/z=655 MH$^+$ base peak

Stage 13(b): 3-(4-Chloro-5-fluoro-1H-pyrrolo[2,3-b]pyridin-2-yl)-5,6-dimethoxy-1-[3-(4-methylperhydro-1,4-diazepin-1-yl)propyl]-1H-pyrrolo[3,2-b]pyridine 3-(4-Chloro-5-fluoro-1H-pyrrolo[2,3-b]pyridin-2-yl)-5,6-dimethoxy-1-[3-(4-methylperhydro-1,4-diazepin-1-yl)propyl]-1H-pyrrolo[3,2-b]pyridine can be prepared as in example 2, stage (2d), but starting with 0.145 g of 3-[4-chloro-5-fluoro-1-(toluene-4-sulfonyl)-1H-pyrrolo[2,3-b]pyridin-2-yl]-5,6-dimethoxy-1-[3-(4-methylperhydro-1,4-diazepin-1-yl)propyl]-1H-pyrrolo[3,2-b]pyridine and 0.25 g of potassium hydroxide in 40 cm$^3$ of methanol. After flash chromatography on a column of silica [eluent: chloroform/2M ammoniacal methanol (74/7 by volume)], 0.062 g of 3-(4-chloro-5-fluoro-1H-pyrrolo[2,3-b]pyridin-2-yl)-5,6-dimethoxy-1-[3-(4-methylperhydro-1,4-diazepin-1-yl)propyl]-1H-pyrrolo[3,2-b]pyridine is thus obtained as a solid with the following characteristics:

melting point: melting at 140-145° C. (Köfler block)

$^1$H NMR spectrum (300 MHz)—δ in ppm—in DMSO-d6: 1.70 (m, 2H); 1.92 (m, 2H); 2.23 (s, 3H); 2.39 (t, J=6.5 Hz, 2H); from 2.47 to 2.55 (partially masked m, 4H); 2.60 (m, 4H); 3.88 (s, 3H); 4.05 (s, 3H); 4.24 (t, J=6.5 Hz, 2H); 7.26 (s, 1H); 7.59 (s, 1H); 8.03 (s, 1H); 8.17 (d, J=2.5 Hz, 1H); 12.15 (broad s, 1H).

Mass spectrum: IE m/z=500 M$^+$; m/z=360 (M-C$_8$H$_{16}$N$_2$)$^+$ base peak

EXAMPLE 14

3-(4-Chloro-5-fluoro-1H-pyrrolo[2,3-b]pyridin-2-yl)-5,6-dimethoxy-1-(3-morpholin-4-ylpropyl)-1H-pyrrolo[3,2-b]pyridine Stage 14(a): 3-[4-Chloro-5-fluoro-1-(toluene-4-sulfonyl)-1H-pyrrolo[2,3-b]pyridin-2-yl]-5,6-dimethoxy-1-(3-morpholin-4-ylpropyl)-1H-pyrrolo[3,2-b]pyridine 3-[4-Chloro-5-fluoro-1-(toluene-4-sulfonyl)-1H-pyrrolo[2,3-b]pyridin-2-yl]-5,6-dimethoxy-1-(3-morpholin-4-ylpropyl)-1H-pyrrolo[3,2-b]pyridine can be prepared as in example 2, stage 2(c), but starting with 0.300 g of 3-[4-chloro-5-fluoro-1-(toluene-4-sulfonyl)-1H-pyrrolo[2,3-b]pyridin-2-yl]-1-(2-iodopropyl)-5,6-dimethoxy-1H-pyrrolo[3,2-b]pyridine, 0.068 g of potassium carbonate and 0.078 g of morpholine in 40 cm$^3$ of acetonitrile. 0.255 g of 3-[4-chloro-5-fluoro-1-(toluene-4-sulfonyl)-1H-pyrrolo[2,3-b]pyridin-2-yl]-5,6-dimethoxy-1-(3-morpholin-4-ylpropyl)-1H-pyrrolo[3,2-b]pyridine is obtained as a resin with the following characteristics:

Rf TLC silica [eluent: dichloromethane/methanol (95/5 by volume)]=0.28

Mass spectrum: IE m/z=627 M$^+$; m/z=514 (M-C$_6$H$_{11}$NO)$^+$; m/z=472 (M-C$_7$H$_7$SO$_2$)$^+$; m/z=359 (m/z=514-C$_7$H$_7$SO$_2$)$^+$ base peak; m/z=100 C$_5$H$_{10}$NO$^+$ Stage 14(b): 3-(4-Chloro-5-fluoro-1H-pyrrolo[2,3-b]pyridin-2-yl)-5,6-dimethoxy-1-(3-morpholin-4-ylpropyl)-1H-pyrrolo[3,2-b]pyridine 3-(4-Chloro-5-fluoro-1H-pyrrolo[2,3-b]pyridin-2-yl)-5,6-dimethoxy-1-(3-morpholin-4-ylpropyl)-1H-pyrrolo[3,2-b]pyridine can be prepared as in example 2, stage (2d), but starting with 0.255 g of 3-[4-chloro-5-fluoro-1-(toluene-4-sulfonyl)-1H-pyrrolo[2,3-b]pyridin-2-yl]-5,6-dimethoxy-1-(3-morpholin-4-ylpropyl)-1H-pyrrolo[3,2-b]-pyridine and 0.455 g of potassium hydroxide in 100 cm$^3$ of methanol. After flash chromatography on a column of silica [eluent: dichloromethane/methanol (95/5 by volume)], 0.100 g of 3-(4-chloro-5-fluoro-1H-pyrrolo[2,3-b]pyridin-2-yl)-5,6-dimethoxy-1-(3-morpholin-4-ylpropyl)-1H-pyrrolo[3,2-b]-pyridine is thus obtained as a solid with the following characteristics:

melting point: melting at 189° C. (Köfler block)

$^1$H NMR spectrum (300 MHz)—δ in ppm—in DMSO-d6: 1.96 (m, 2H); 2.24 (t, J=7.0 Hz, 2H); 2.31 (m, 4H); 3.57 (m, 4H); 3.88 (s, 3H); 4.06 (s, 3H); 4.26 (t, J=7.0 Hz, 2H); 7.27 (s, 1H); 7.61 (s, 1H); 8.03 (s, 1H); 8.18 (d, J=2.5 Hz, 1H); 12.15 (broad m, 1H).

Mass spectrum: ES m/z=474 MH$^+$ base peak

EXAMPLE 15

C-(1-{3-[3-(4-Chloro-5-fluoro-1H-pyrrolo[2,3-b]pyridin-2-yl)-5,6-dimethoxypyrrolo[3,2-b]pyridin-1-yl]propyl}piperidin-4-yl)methylamine Stage 15(a): C-[1-(3-{3-[4-Chloro-5-fluoro-1-(toluene-4-sulfonyl)-1H-pyrrolo[2,3-b]pyridin-2-yl]-5,6-dimethoxypyrrolo[3,2-b]pyridin-1-yl}propyl)piperidin-4-yl]methylamine C-[1-(3-{3-[4-Chloro-5-fluoro-1-(toluene-4-sulfonyl)-1H-pyrrolo[2,3-b]pyridin-2-yl]-5,6-dimethoxypyrrolo[3,2-b]pyridin-1-yl}propyl)piperidin-4-yl]methylamine can be prepared as in example 11, stage (c), but starting with 0.300 g of 3-[4-chloro-5-fluoro-1-(toluene-4-sulfonyl)-1H-pyrrolo[2,3-b]pyridin-2-yl]-1-(3-iodopropyl)-5,6-dimethoxy-1H-pyrrolo[3,2-b]pyridine and 0.512 g of C-piperidin-4-ylmethylamine in 50 cm$^3$ of dichloromethane. After flash chromatography on a column of silica [eluent: chloroform/methanol/28% aqueous ammonia (12/3/0.5 by volume)], 0.150 g of C-[1-(3-{3-[4-chloro-5-fluoro-1-(toluene-4-sulfonyl)-1H-pyrrolo[2,3-b]pyridin-2-yl]-5,6-dimethoxypyrrolo[3,2-b]pyridin-1-yl}propyl)piperidin-4-yl]methylamine is thus obtained as a resin with the following characteristics:

Rf TLC silica [eluent: chloroform/methanol/28% aqueous ammonia (12/3/0.5 by volume)]=0.60

Mass spectrum: IC m/z=655 MH$^+$ base peak

Stage 15(b): C-(1-{3-[3-(4-Chloro-5-fluoro-1H-pyrrolo[2,3-b]pyridin-2-yl)-5,6-dimethoxypyrrolo[3,2-b]pyridin-1-yl]propyl}piperidin-4-yl)methylamine C-(1-{3-[3-(4-Chloro-5-fluoro-1H-pyrrolo[2,3-b]pyridin-2-yl)-5,6-dimethoxypyrrolo[3,2-b]pyridin-1-yl]propyl}piperidin-4-yl)methylamine can be prepared as in example 2, stage (2d), but starting with 0.150 g of C-[1-(3-{3-(4-chloro-5-fluoro-1-(toluene-4-sulfonyl)-1H-pyrrolo[2,3-b]pyridin-2-yl)-5,6-dimethoxypyrrolo[3,2-b]pyridin-1-yl}propyl)piperidin-4-yl]methylamine and 0.256 g of potassium hydroxide in 50 cm³ of methanol. After flash chromatography on a column of silica [eluent: chloroform/2M ammoniacal methanol (90/10 by volume)], 0.035 g of C-(1-{3-[3-(4-chloro-5-fluoro-1H-pyrrolo[2,3-b]pyridin-2-yl)-5,6-dimethoxypyrrolo[3,2-b]pyridin-1-yl]propyl}piperidin-4-yl)methylamine is thus obtained as a solid with the following characteristics:

melting point: melting at 135° C. (Köfler block)

$^1$H NMR spectrum (300 MHz)—δ in ppm in DMSO-d6: from 1.01 to 1.21 (m, 3H); 1.65 (m, 2H); 1.79 (m, 2H); 1.95 (m, 2H); 2.21 (t, J=7.0 Hz, 2H); 2.40 (d, J=5.5 Hz, 2H); 2.80 (m, 2H); 3.88 (s, 3H); 4.05 (s, 3H); 4.23 (t, J=7.0 Hz, 2H); 7.26 (s, 1H); 7.59 (s, 1H); 8.03 (s, 1H); 8.18 (d, J=2.5 Hz, 1H); from 11.4 to 12.4 (very broad m, 1H).

Mass spectrum: IE m/z=500 M$^+$; m/z=360 (M-C$_8$H$_{16}$N$_2$)$^+$ base peak

EXAMPLE 16

3-(4-Chloro-5-fluoro-1H-pyrrolo[2,3-b]pyridin-2-yl)-5,6-dimethoxy-1-[3-(4-methylpiperazin-1-yl)propyl]-1H-pyrrolo[3,2-b]pyridine Stage 16(a): 3-[4-Chloro-5-fluoro-1-(toluene-4-sulfonyl)-1H-pyrrolo[2,3-b]pyridin-2-yl]-5,6-dimethoxy-1-[3-(4-methylpiperazin-1-yl)propyl]-1H-pyrrolo[3,2-b]pyridine 3-[4-Chloro-5-fluoro-1-(toluene-4-sulfonyl)-1H-pyrrolo[2,3-b]pyridin-2-yl]-5,6-dimethoxy-1-[3-(4-methylpiperazin-1-yl)propyl]-1H-pyrrolo[3,2-b]pyridine can be prepared as in example 2, stage 2(c), but starting with 0.300 g of 3-[4-chloro-5-fluoro-1-(toluene-4-sulfonyl)-1H-pyrrolo[2,3-b]pyridin-2-yl]-1-(2-iodopropyl)-5,6-dimethoxy-1H-pyrrolo[3,2-b]pyridine, 0.068 g of potassium carbonate and 0.090 g of 1-methylpiperazine in 50 cm³ of acetonitrile. 0.192 g of 3-[4-chloro-5-fluoro-1-(toluene-4-sulfonyl)-1H-pyrrolo[2,3-b]pyridin-2-yl]-5,6-dimethoxy-1-(3-morpholin-4-ylpropyl)-1H-pyrrolo[3,2-b]pyridine is obtained as a resin with the following characteristics:

Rf TLC silica [eluent: dichloromethane/methanol (90/10 by volume)]+0.23

Mass spectrum: IE m/z=640 M$^+$; m/z=485 (M-C$_7$H$_7$SO$_2$)$^+$; m/z=385 (m/z=485-C$_5$H$_{12}$N$_2$)$^+$; m/z=359 (m/z=485-C$_7$H$_{14}$N$_2$)$^+$ base peak; m/z=98 C$_6$H$_{12}$N$^+$ Stage 16(b): 3-(4-Chloro-5-fluoro-1H-pyrrolo[2,3-b]pyridin-2-yl)-5,6-dimethoxy-1-[3-(4-methylpiperazin-1-yl)propyl]-1H-pyrrolo[3,2-b]pyridine 3-(4-Chloro-5-fluoro-1H-pyrrolo[2,3-b]pyridin-2-yl)-5,6-dimethoxy-1-[3-(4-methylpiperazin-1-yl)propyl]-1H-pyrrolo[3,2-b]pyridine can be prepared as in example 2, stage (2d), but starting with 0.190 g of 3-(4-chloro-5-fluoro-1-(toluene-4-sulfonyl)-1H-pyrrolo(2,3-b]pyridin-2-yl)-5,6-dimethoxy-1-(3-morpholin-4-ylpropyl)-1H-pyrrolo[3,2-b]pyridine and 0.332 g of potassium hydroxide in 50 cm³ of methanol. After flash chromatography on a column of silica (eluent: dichloromethane/methanol (90/10 by volume)], 0.054 g of 3-(4-chloro-5-fluoro-1H-pyrrolo(2,3-b]pyridin-2-yl)-5,6-dimethoxy-1-[3-(4-methylpiperazin-1-yl)propyl]-1H-pyrrolo[3,2-b]pyridine is thus obtained as a solid with the following characteristics:

melting point: melting at 155° C. (Köfler block)

$^1$H NMR spectrum (300 MHz)—δ in ppm—in DMSO-d6: 1.95 (m, 2H); 2.14 (s, 3H); 2.23 (t, J=7.0 Hz, 2H); from 2.25 to 2.40 (broad m, 8H); 3.88 (s, 3H); 4.05 (s, 3H); 4.24 (t, J=7.0 Hz, 2H); 7.26 (broad s, 1H); 7.59 (S, 1H); 8.03 (s, 1H); 8.18 (d, J=2.5 Hz, 1H); 12.15 (broad s, 1H).

Mass spectrum: ES m/z=487 MH$^+$ base peak

EXAMPLE 17

3-(4-Chloro-1H-pyrrolo[2,3-b]pyridin-2-yl)-5,6-dimethoxy-1-[2-(2-methoxyethoxy)ethyl]-1H-pyrrolo[3,2-b]pyridine Stage 17(a): 3-(4-Chloro-1-(toluene-4-sulfonyl)-1H-pyrrolo[2,3-b]pyridin-2-yl)-5,6-dimethoxy-1-[2-(2-methoxyethoxy)ethyl]-1H-pyrrolo[3,2-b]pyridine 3-(4-Chloro-1-(toluene-4-sulfonyl)-1H-pyrrolo[2,3-b]pyridin-2-yl)-5,6-dimethoxy-1-[2-(2-methoxyethoxy)ethyl]-1H-pyrrolo[3,2-b]pyridine can be prepared as in example 5, stage 5(a), but starting with 0.15 g of 3-(4-chloro-1-(toluene-4-sulfonyl)-1H-pyrrolo[2,3-b]pyridin-2-yl)-5,6-dimethoxy-1H-pyrrolo3,2-b]pyridine, 10 cm³ of 1-bromo-2-(2-methoxyethoxy)ethane, 0.116 g of potassium hydroxide, 0.1 g of potassium carbonate and 0.002 g of tetrabutylammonium bromide. 0.384 g of 3-(4-chloro-1-(toluene-4-sulfonyl)-1H-pyrrolo[2,3-b]pyridin-2-yl)-5,6-dimethoxy-1-[2-(2-methoxyethoxy)ethyl]-1H-pyrrolo[3,2-b]pyridine is thus obtained with the following characteristics:

Rf TLC silica [eluent: dichloromethane/methanol (95/5 by volume)]=0.27

Mass spectrum: ES m/z=585 MH$^+$ base peak

Stage 17(b): 3-(4-Chloro-1H-pyrrolo[2,3-b]pyridin-2-yl)-5,6-dimethoxy-1-[2-(2-methoxyethoxy)ethyl]-1H-pyrrolo[3,2-b]pyridine 3-(4-Chloro-1H-pyrrolo[2,3-b]pyridin-2-yl)-5,6-dimethoxy-1-[2-(2-methoxyethoxy)ethyl]-1H-pyrrolo[3,2-b]pyridine can be prepared as in example 5, stage 5(d), but starting with 0.082 g of 3-(4-chloro-1-(toluene-4-sulfonyl)-1H-pyrrolo[2,3-b]pyridin-2-yl)-5,6-dimethoxy-1-[2-(2-methoxyethoxy)ethyl]-1H-pyrrolo[3,2-b]pyridine and 0.62 cm³ of aqueous 5N potassium hydroxide in 10 cm³ of methanol. 0.021 g of 3-(4-chloro-1H-pyrrolo[2,3-b]pyridin-2-yl)-5,6-dimethoxy-1-[2-(2-methoxyethoxy)ethyl]-1H-pyrrolo[3,2-b]pyridine is thus obtained as a green solid with the following characteristics:

$^1$H NMR spectrum (300 MHz)—δ in ppm—in DMSO-d6: 3.18 (s, 3H); 3.41 (m, 2H); 3.53 (m, 2H); 3.77 (t, J=5.0 Hz, 2H); 3.87 (s, 3H); 4.04 (s, 3H); 4.37 (t, J=5.0 Hz, 2H); 7.12 (d, J=5.5 Hz, 1H); 7.25 (d, J=2.0 Hz, 1H); 7.65 (s, 1H); 8.02 (s, 1H); 8.05 (d, J=5.5 Hz, 1H); 12.1 (broad m, 1H).

Mass spectrum: ES m/z =431 MH$^+$ base peak

EXAMPLE 18

{2-[3-(4-Chloro-1H-pyrrolo[2,3-b]pyridin-2-yl)-5,6-dimethoxypyrrolo[3,2-b]pyridin-1-yl]ethyl}diethylamine Stage 18(a): {2-[3-(4-Chloro-1-(toluene-4-sulfonyl)-1H-pyrrolo[2,3-b]pyridin-2-yl]-5,6-dimethoxypyrrolo[3,2-b]pyridin-1-yl]ethyl}diethylamine {2-[3-(4-Chloro-1-(toluene-4-sulfonyl)-1H-pyrrolo[2,3-b]pyridin-2-yl]-5,6-dimethoxypyrrolo[3,2-b]pyridin-1-yl]

ethyl}diethylamine can be prepared as in example 5, stage 5(c), but starting with 0.2 g of 3-[4-chloro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine in 20 cm³ of CH₂Cl₂ and 0.82 cm³ of diethylamine. 0.107 g of {2-[3-(4-chloro-1-(toluene-4-sulfonyl)-1H-pyrrolo[2,3-b]pyridin-2-yl]-5,6-dimethoxypyrrolo[3,2-b]pyridin-1-yl]ethyl}diethylamine is thus obtained as an orange resin with the following characteristics:

Rf TLC silica [eluent: dichloromethane/methanol (95/5 by volume)]=0.86

Mass spectrum: ES m/z=582 MH⁺ base peak

Stage 18(b): {2-[3-(4-Chloro-1H-pyrrolo[2,3-b]pyridin-2-yl)-5,6-dimethoxypyrrolo[3,2-b]pyridin-1-yl]ethyl}diethylamine {2-[3-(4-Chloro-1H-pyrrolo[2,3-b]pyridin-2-yl)-5,6-dimethoxypyrrolo[3,2-b]pyridin-1-yl]ethyl}diethylamine can be prepared as in example 5, stage 5(d), but starting with 0.107 g of {2-[3-(4-chloro-1-(toluene-4-sulfonyl)-1H-pyrrolo[2,3-b]pyridin-2-yl]-5,6-dimethoxypyrrolo[3,2-b]pyridin-1-yl]ethyl}diethylamine and 0.103 g of potassium hydroxide in 40 cm³ of methanol. 0.063 g of {2-[3-(4-chloro-1H-pyrrolo[2,3-b]pyridin-2-yl)-5,6-dimethoxypyrrolo[3,2-b]pyridin-1-yl]ethyl}diethylamine is thus obtained as a cream-colored powder with the following characteristics:

¹H NMR spectrum (300 MHz)—δ in ppm—in DMSO-d6: 0.88 (t, J=7.5 Hz, 6H); from 2.44 to 2.55 (partially masked m, 4H); 2.77 (t, J=6.5 Hz, 2H); 3.87 (s, 3H); 4.05 (s, 3H); 4.24 (t, J=6.5 Hz, 2H); 7.11 (d, J=5.5 Hz, 1H); 7.23 (broad s, 1H); 7.62 (s, 1H); 8.04 (s, 1H); 8.05 (d, J=5.5 Hz, 1H); 12.1 (broad s, 1H).

Mass spectrum: IE m/z=427 M⁺; m/z=86 C₅H₁₂N⁺ base peak

EXAMPLE 19

C-(1-{2-[3-(4-Chloro-1H-pyrrolo[2,3-b]pyridin-2-yl)-5,6-dimethoxypyrrolo[3,2-b]pyridin-1-yl]ethyl}piperidin-4-yl)methylamine Stage 19(a): C-[1-(2-{3-[4-Chloro-1-(toluene-4-sulfonyl)-1H-pyrrolo[2,3-b]pyridin-2-yl]-5,6-dimethoxypyrrolo[3,2-b]pyridin-1-yl}ethyl)piperidin-4-yl]methylamine C-[1-(2-{3-[4-Chloro-1-(toluene-4-sulfonyl)-1H-pyrrolo[2,3-b]pyridin-2-yl]-5,6-dimethoxypyrrolo[3,2-b]pyridin-1-yl}ethyl)piperidin-4-yl]methylamine can be prepared as in example 5, stage 5(c), but starting with 0.3 g of 3-[4-chloro-1-(toluene-4-sulfonyl)-1H-pyrrolo[2,3-b]pyridin-2-yl]-1-(2-iodoethyl)-5,6-dimethoxy-1H-pyrrolo[3,2-b]pyridine in 40 cm³ of CH₂Cl₂ and 0.538 g of 4-aminomethylpiperidine. 0.108 g of C-[1-(2-{3-[4-chloro-1-(toluene-4-sulfonyl)-1H-pyrrolo[2,3-b]pyridin-2-yl]-5,6-dimethoxypyrrolo[3,2-b]pyridin-1-yl}ethyl)piperidin-4-yl]methylamine is thus obtained as an orange resin with the following characteristics:

Rf TLC silica [eluent: chloroform/methanol/ammonia (13/3/0.5 by volume)]=0.5

Mass spectrum: ES m/z=623 MH⁺

Stage 19(b): C-(1-{2-[3-(4-Chloro-1H-pyrrolo[2,3-b]pyridin-2-yl)-5,6-dimethoxypyrrolo[3,2-b]pyridin-1-yl]ethyl}piperidin-4-yl)methylamine C-(1-{2-[3-(4-Chloro-1H-pyrrolo[2,3-b]pyridin-2-yl)-5,6-dimethoxypyrrolo[3,2-b]pyridin-1-yl]ethyl}piperidin-4-yl)methylamine can be prepared as in example 5, stage 5(d), but starting with 0.108 g of C-[1-(2-{3-[4-chloro-1-(toluene-4-sulfonyl)-1H-pyrrolo[2,3-b]pyridin-2-yl]-5,6-dimethoxypyrrolo[3,2-b]pyridin-1-yl}ethyl)piperidin-4-yl]methylamine and 0.194 g of potassium hydroxide in 30 cm³ of methanol. 0.04 g of C-(1-{2-[3-(4-chloro-1H-pyrrolo[2,3-b]pyridin-2-yl)-5,6-dimethoxypyrrolo[3,2-b]pyridin-1-yl]ethyl}piperidin-4-yl)methylamine is thus obtained as a cream-colored powder with the following characteristics:

Mass spectrum: IE m/z=468 M⁺; m/z=127 C₇H₁₅N₂⁺ base peak; m/z=110 (m/z=127-NH₃)⁺

¹H NMR spectrum (300 MHz)—δ in ppm—in DMSO-d6: from 0.98 to 1.21 (m, 3H); 1.65 (m, 2H); 1.96 (m, 2H); 2.38 (d, J=6.0 Hz, 2H); 2.68 (t, J=6.5 Hz, 2H); 2.90 (m, 2H); 3.88 (s, 3H); 4.06 (s, 3H); 4.29 (t, J=6.5 Hz, 2H); 7.11 (d, J=5.5 Hz, 1H); 7.25 (s, 1H); 7.65 (s, 1H); 8.02 (s, 1H); 8.05 (d, J=5.5 Hz, 1H); 12.1 (broad m, 1H).

EXAMPLE 20

3-(4-Chloro-1H-pyrrolo[2,3-b]pyridin-2-yl)-5,6-dimethoxy-1H-pyrrolo[3,2-b]pyridine 3-(4-Chloro-1H-pyrrolo[2,3-b]pyridin-2-yl)-5,6-di-methoxy-1H-pyrrolo[3,2-b]pyridine can be prepared as in example 5, stage 5(d), but starting with 0.2 g of 3-[4-chloro-1-(toluene-4-sulfonyl)-1H-pyrrolo[2,3-b]pyridin-2-yl]-5,6-dimethoxy-1H-pyrrolo[3,2-b]pyridine and 0.511 g of potassium hydroxide in 20 cm³ of methanol. 0.0273 g of 3-(4-chloro-1H-pyrrolo[2,3-b]pyridin-2-yl)-5,6-dimethoxy-1H-pyrrolo[3,2-b]pyridine is thus obtained as a gray solid with the following characteristics:

Mass spectrum: IE m/z=328 M⁺ base peak; m/z=313 (M-CH₃)⁺

¹H NMR spectrum (300MHz)—δ in ppm—in DMSO-d6: 3.84 (s, 3H); 4.05 (s, 3H); 7.12 (d, J=5.5,Hz, 1H); 7.26 (d, J=2.0, 1H); 7.39 (s, 1H); 8.01 (d, J=2.0 Hz, 1H); 8.05 (d, J=5.5 Hz, 1H); 11.35 (broad m, 1H); 12.1 (broad m, 1H).

EXAMPLE 21

Potassium [3-(4-chloro-1H-pyrrolo[2,3-b]pyridin-2-yl)-5,6-dimethoxypyrrolo[3,2-b]pyridin-1-yl]acetate Stage 21(a): tert-Butyl [3-(4-chloro-1-(toluene-4-sulfonyl)-1H-pyrrolo[2,3-b]pyridin-2-yl)-5,6-dimethoxypyrrolo[3,2-b]pyridin-1-yl]acetate tert-Butyl [3-(4-chloro-1-(toluene-4-sulfonyl)-1H-pyrrolo[2,3-b]pyridin-2-yl)-5,6-dimethoxypyrrolo[3,2-b]pyridin-1-yl]acetate is prepared in the following manner:

To a solution of 0.5 g of 3-[4-chloro-1-(toluene-4-sulfonyl)-1H-pyrrolo[2,3-b]pyridin-2-yl]-5,6-dimethoxy-1H-pyrrolo[2,3-b]pyridine in 10 cm³ of tert-butyl bromoacetate, under an inert atmosphere of argon at a temperature in the region of 20° C., are added 0.333 g of potassium carbonate, 0.387 g of potassium hydroxide and 0.0067 g of tetrabutylammonium bromide. The reaction medium is stirred at the same temperature for 16 hours. 100 cm³ of dichloromethane are added and the organic phase is washed with 3×100 cm³ of water. After separation of the phases by settling, the organic phase is dried over magnesium sulfate, filtered and then concentrated under reduced pressure. The residue obtained is purified by flash chromatography (silica, cyclohexane/ethyl acetate, 75/25 by volume). The fractions containing the product are concentrated under reduced pressure. 0.51 g of tert-butyl [3-(4-chloro-1-(toluene-4-sulfonyl)-1H-pyrrolo[2,3-b]

pyridin-2-yl)-5,6-dimethoxy-pyrrolo[3,2-b]pyridin-1-yl] acetate is thus obtained with the following characteristics:

Rf TLC silica [eluent: cyclohexane/ethyl acetate (50/50 by volume)]=0.14

Mass spectrum: IE m/z=596 M$^{+\cdot}$; m/z=540 (M-C$_4$H$_8$)$^{+\cdot}$; m/z=385 (m/z=540-C$_7$H$_7$SO$_2$)$^+$ base peak; m/z=341 (m/z=385-CO$_2$)$^+$ Stage 21(b): Potassium [3-(4-chloro-1H-pyrrolo[2,3-b]pyridin-2-yl)-5,6-dimethoxypyrrolo[3,2-b]pyridin-1-yl]acetate Potassium [3-(4-chloro-1H-pyrrolo[2,3-b]pyridin-2-yl)-5,6-dimethoxypyrrolo[3,2-b]pyridin-1-yl]acetate can be prepared as in example 5, stage 5(d), but starting with 0.51 g of tert-butyl [3-(4-chloro-1-(toluene-4-sulfonyl)-1H-pyrrolo[2,3-b]pyridin-2-yl)-5,6-dimethoxy-pyrrolo[3,2-b]pyridin-1-yl] acetate and 3.34 g of potassium hydroxide in 33.4 cm$^3$ of methanol. 0.125 g of potassium [3-(4-chloro-1H-pyrrolo[2,3-b]pyridin-2-yl)-5,6-dimethoxypyrrolo[3,2-b]pyridin-1-yl] acetate is thus obtained as a yellow solid with the following characteristics:

Mass spectrum: IE m/z=386 M$^+$. base peak; m/z=341 (M-CO$_2$H)$^+$; m/z=44 CO$_2^{+\cdot}$ $^1$H NMR spectrum (300MHz)—δ in ppm—in DMSO-d6: 3.82 (s, 3H); 4.03 (s, 3H); 4.67 (s, 2H); 7.11 (d, J=5.5 Hz, 1H); 7.23 (S, 1H); 7.49 (s, 1H); 7.92 (s, 1H); 8.03 (d, J=5.5 Hz, 1H); 12.05 (broad m, 1H).

EXAMPLE 22

2-[3-(4-Chloro-1H-pyrrolo[2,3-b]pyridin-2-yl)-5,6-dimethoxypyrrolo[3,2-b]pyridin-1-yl]-1-(4-methylpiperazin-1-yl)ethanone 2-[3-(4-Chloro-1H-pyrrolo[2,3-b]pyridin-2-yl)-5,6-dimethoxypyrrolo[3,2-b]pyridin-1-yl]-1-(4-methylpiperazin-1-yl)ethanone is prepared in the following manner:

To a solution of 0.15 g of potassium 3-(4-chloro-1H-pyrrolo[2,3-b]pyridin-2-yl)-5,6-dimethoxy-pyrrolo[3,2-b]pyridin-1-yl]acetate in 4 cm$^3$ of dimethylformamide, under an inert atmosphere of argon at a temperature in the region of 20° C., is added 0.146 g of O-(1H-benzotriazol-1-yl)-N,N,N',N'-tetramethyluronium hexafluorophosphate. The reaction medium is stirred at this same temperature for 1 hour. 0.046 g of 1-methylpiperazine and then 0.067 cm$^3$ of diisopropylethylamine are added. After stirring for 16 hours at the same temperature, 20 cm$^3$ of water and 40 cm$^3$ of dichloromethane are added. After separation of the phases by settling, the organic phase is dried over magnesium sulfate, filtered and then concentrated under reduced pressure. The residue obtained is purified by flash chromatography (silica, dichloromethane/methanol, 95/05 by volume). The fractions containing the product are concentrated under reduced pressure. 0.0647 g of 2-[3-(4-chloro-1H-pyrrolo[2,3-b]pyridin-2-yl)-5,6-dimethoxypyrrolo[3,2-b]pyridin-1-yl]-1-(4-methyl-piperazin-1-yl) ethanone is thus obtained with the following characteristics:

Mass spectrum: ES m/z=469 MH$^+$ base peak; m/z=235 (M+2H)$^{2+}$/2

$^1$H NMR spectrum (300 MHz)—δ in ppm—in DMSO-d6: 2.22 (s, 3H); 2.31 (m, 2H); 2.42 (m, 2H); 3.48 (m, 2H); 3.59 (m, 2H); 3.85 (s, 3H); 4.06 (s, 3H); 5.25 (s, 2H); 7.12 (d, J=5.5 Hz, 1H); 7.28 (d, J=2.0 Hz, 1H); 7.55 (s, 1H); 7.89 (s, 1H); 8.05 (d, J=5.5 Hz, 1H); 12.05 (broad s, 1H)

EXAMPLE 23

2-[3-(4-Chloro-1H-pyrrolo[2,3-b]pyridin-2-yl)-5,6-dimethoxypyrrolo[3,2-b]pyridin-1-yl]-1-(4-hydroxypiperidin-1-yl)ethanone 2-[3-(4-Chloro-1H-pyrrolo[2,3-b]pyridin-2-yl)-5,6-dimethoxypyrrolo[3,2-b]pyridin-1-yl]-1-(4-hydroxy-piperidin-1-yl)ethanone can be prepared as in example 22, but starting with 0.15 g of potassium 3-(4-chloro-1H-pyrrolo[2,3-b]pyridin-2-yl)-5,6-dimethoxy-pyrrolo[3,2-b]pyridin-1-yl]acetate in 4 cm$^3$ of dimethylformamide, and 0.146 g of O-(1H-benzotriazol-1-yl)-N,N,N',N'-tetramethyluronium hexafluorophosphate and 0.046 g of 4-hydroxypiperazine. 0.0546 g of 2-[3-(4-chloro-1H-pyrrolo[2,3-b]pyridin-2-yl)-5,6-dimethoxy-pyrrolo[3,2-b]pyridin-1-yl]-1-(4-hydroxypiperidin-1-yl)ethanone is thus obtained with the following characteristics:

Mass spectrum: IE m/z=469 M$^+$ base peak; m/z=341 (M-C$_6$H$_{10}$NO$_2$)$^+$ $^1$H NMR spectrum (300MHz)—δ in ppm—in DMSO-d6: from 1.22 to 1.55 (m, 2H); from 1.69 to 1.92 (m, 2H); 3.11 (m, 1H); from 3.25 to 3.38 (partially masked m, 1H); from 3.72 to 3.94 (m, 3H); 3.84 (s, 3H); 4.06 (s, 3H); 4.78 (d, J=4.0 Hz, 1H); 5.24 (m, 2H); 7.12 (d, J=5.5 Hz, 1H); 7.28 (d, J=2.0 Hz, 1H); 7.55 (s, 1H); 7.90 (s, 1H); 8.04 (d, J=5.5 Hz, 1H); 12.05 (broad s, 1H).

EXAMPLE 24

2-[3-(4-Chloro-1H-pyrrolo[2,3-b]pyridin-2-yl)-5,6-dimethoxypyrrolo[3,2-b]pyridin-1-yl]-1-morpholin-4-ylethanone 2-[3-(4-Chloro-1H-pyrrolo[2,3-b]pyridin-2-yl)-5,6-dimethoxypyrrolo[3,2-b]pyridin-1-yl]-1-morpholin-4-ylethanone can be prepared as in example 22, but starting with 0.15 g of potassium 3-(4-chloro-1H-pyrrolo[2,3-b]pyridin-2-yl)-5,6-dimethoxypyrrolo[3,2-b]pyridin-1-yl]acetate in 4 cm$^3$ of dimethylformamide, and 0.146 g of O-(1H-benzotriazol-1-yl)-N,N,N',N'-tetramethyluronium hexafluorophosphate, and 0.040 g of morpholine. The reaction medium is stirred at this same temperature for 1 hour. 0.046 g of 1-methylpiperazine is added. 0.0612 g of 2-[3-(4-chloro-1H-pyrrolo[2,3-b]pyridin-2-yl)-5,6-dimethoxypyrrolo[3,2-b]pyridin-1-yl]-1-morpholin-4-ylethanone is thus obtained with the following characteristics:

Mass spectrum: ES m/z=456 MH$^+$ base peak $^1$H NMR spectrum (300MHz)—δ in ppm—in DMSO-d6: 3.48 (m, 2H); 3.61 (m, 4H); 3.71 (m, 2H); 3.85 (s, 3H); 4.06 (s, 3H); 5.27 (s, 2H); 7.13 (d, J=5.5 Hz, 1H); 7.28 (d, J=2.0 Hz, 1H); 7.56 (s, 1H); 7.89 (s, 1H); 8.05 (d, J=5.5 Hz, 1H); 12.1 (broad s, 1H)

EXAMPLE 25

2-(1-{3-[3-(4-Chloro-1H-pyrrolo[2,3-b]pyridin-2-yl)-5,6-dimethoxypyrrolo[3,2-b]pyridin-1-yl]-propyl}piperidin-4-yl)ethanol Stage 25(a): 1-(3-Chloropropyl)-3-[4-chloro-1-(toluene-4-sulfonyl)-1H-pyrrolo[2,3-b]pyridin-2-yl]-5,6-dimethoxy-1H-pyrrolo[3,2-b]pyridine 1-(3-Chloropropyl)-3-[4-chloro-1-(toluene-4-sulfonyl)-1H-pyrrolo[2,3-b]pyridin-2-yl]-5,6-dimethoxy-1H-pyrrolo[3,2-b]pyridine can be prepared as in example 5, stage 5(a), but starting with 1.5 g of 3-(4-chloro-1-(toluene-4-sulfonyl)-1H-pyrrolo[2,3-b]pyridin-2-yl)-5,6-dimethoxy-1H-pyrrolo[3,2-b]pyridine, 75 cm³ of 1,3-bromochloropropane, 1.37 g of potassium hydroxide, 1 g of potassium carbonate and 0.02 g of tetrabutylammonium bromide. 1.69 g of 1-(3-chloropropyl)-3-[4-chloro-1-(toluene-4-sulfonyl)-1H-pyrrolo[2,3-b]pyridin-2-yl]-5,6-dimethoxy-1H-pyrrolo[3,2-b]pyridine are thus obtained with the following characteristics:

Rf TLC silica [eluent: cyclohexane/ethyl acetate (50/50 by volume)]=0.57

Mass spectrum: ES m/z=559 MH⁺ base peak

Stage 25(b): 1-(3-Iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine 1-(3-Iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine can be prepared as in example 5, stage 5(b), but starting with 1.65 g of 1-(3-chloropropyl)-3-[4-chloro-1-(toluene-4-sulfonyl)-1H-pyrrolo[2,3-b]pyridin-2-yl]-5,6-dimethoxy-1H-pyrrolo[3,2-b]pyridine and 0.663g of sodium iodide in 150 cm³ of methyl ethyl ketone. 2 g of 1-(3-iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine are thus obtained with the following characteristics:

Rf TLC silica [eluent: cyclohexane/ethyl acetate (75/25 by volume)]=0.21

Mass spectrum: IE m/z=650 M⁺. base peak;
m/z=495 (M-$C_7H_7SO_2$)⁺; m/z=368 (m/z=495-I)⁺; m/z=91 $C_7H_7^+$ Stage 25(c): 2-[1-(3-{3-[4-Chloro-1-(toluene-4-sulfonyl)-1H-pyrrolo[2,3-b]pyridin-2-yl]-5,6-dimethoxy-pyrrolo[3,2-b]pyridin-1-yl}propyl)piperidin-4-yl]ethanol 2-[1-(3-{3-[4-Chloro-1-(toluene-4-sulfonyl)-1H-pyrrolo[2,3-b]pyridin-2-yl]-5,6-dimethoxypyrrolo[3,2-b]pyridin-1-yl}propyl)piperidin-4-yl]ethanol can be prepared as in example 5, stage 5(c), but starting with 0.5 g of 1-(3-iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine and 0.298 g of 4-piperidineethanol and 0.318 g of potassium carbonate in 20 cm³ of dimethylformamide. 0.405 g of 2-[1-(3-{3-[4-chloro-1-(toluene-4-sulfonyl)-1H-pyrrolo[2,3-b]pyridin-2-yl]-5,6-dimethoxypyrrolo[3,2-b]pyridin-1-yl}propyl)-piperidin-4-yl]ethanol is thus obtained with the following characteristics:

Rf TLC silica [eluent: dichloromethane/methanol (90/10 by volume)]=0.19

Mass spectrum: IE m/z=651 M⁺·; m/z=496 (M-$C_7H_7SO_2$)⁺; m/z=342 (m/z=496-$C_9H_{16}$NO)⁺. base peak; m/z=142 $C_8H_{16}NO^+$ Stage 25(d): 2-(1-{3-[3-(4-Chloro-1H-pyrrolo[2,3-b]pyridin-2-yl)-5,6-dimethoxypyrrolo[3,2-b]pyridin-1-yl]propyl}piperidin-4-yl)ethanol 2-(1-{3-[3-(4-Chloro-1H-pyrrolo[2,3-b]pyridin-2-yl)-5,6-dimethoxypyrrolo[3,2-b]pyridin-1-yl]propyl}piperidin-4-yl)ethanol can be prepared as in example 5, stage 5(d), but starting with 0.4 g of 2-[1-(3-{3-[4-chloro-1-(toluene-4-sulfonyl)-1H-pyrrolo[2,3-b]pyridin-2-yl]-5,6-dimethoxypyrrolo[3,2-b]pyridin-1-yl}propyl)piperidin-4-yl]ethanol and 0.89 g of potassium hydroxide in 25 cm³ of methanol. 0.22 g of 2-(1-{3-[3-(4-chloro-1H-pyrrolo[2,3-b]pyridin-2-yl)-5,6-dimethoxy-pyrrolo[3,2-b]pyridin-1-yl]propyl}piperidin-4-yl)-ethanol is thus obtained with the following characteristics:

¹H NMR spectrum (300 MHz)—δ in ppm—in DMSO-d6: from 1.08 to 1.24 (m, 2H); from 1.28 to 1.41 (m, 3H); 1.61 (m, 2H); 1.81 (m, 2H); 1.95 (m, 2H); 2.21 (t, J=6.5 Hz, 2H); 2.79 (m, 2H); 3.42 (m, 2H); 3.88 (s, 3H); 4.05 (s, 3H); 4.23 (t, J=6.5 Hz, 2H); 4.29 (t, J=5.5 Hz, 1H); 7.12 (d, J=5.5 Hz, 1H); 7.22 (broad s, 1H); 7.59 (s, 1H); 8.02 (s, 1H); 8.06 (d, J=5.5 Hz, 1H); 12.05 (broad s, 1H).

Mass spectrum: IE m/z=497 M⁺; m/z=342 (M-$C_9H_{17}$NO)⁺ base peak; m/z=142 $C_8H_{16}NO^+$

EXAMPLE 26

1-{3-[3-(4-Chloro-1H-pyrrolo[2,3-b]pyridin-2-yl)-5,6-dimethoxypyrrolo[3,2-b]pyridin-1-yl]propyl}piperidin-4-ol Stage 26(a): 1-(3-{3-[4-Chloro-1-(toluene-4-sulfonyl)-1H-pyrrolo[2,3-b]pyridin-2-yl]-5,6-dimethoxypyrrolo[3,2-b]pyridin-1-yl}propyl)piperidin-4-ol 1-(3-{3-[4-Chloro-1-(toluene-4-sulfonyl)-1H-pyrrolo[2,3-b]pyridin-2-yl]-5,6-dimethoxypyrrolo[3,2-b]pyridin-1-yl}propyl)piperidin-4-ol can be prepared as in example 5, stage 5(c), but starting with 0.5 g of 1-(3-iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine and 0.233 g of 4-hydroxypiperidine and 0.318 g of potassium carbonate in 20 cm³ of dimethylformamide. 0.565 g of 1-(3-{3-[4-chloro-1-(toluene-4-sulfonyl)-1H-pyrrolo[2,3-b]pyridin-2-yl]-5,6-dimethoxypyrrolo[3,2-b]pyridin-1-yl}propyl)piperidin-4-ol is thus obtained with the following characteristics:

Rf TLC silica [eluent: dichloromethane/methanol (90/10 by volume)]=0.17

Mass spectrum: IE m/z=623 M⁺; m/z=496 (M-$C_7H_{13}$NO)⁺; m/z=341 (m/z=496-$C_7H_7SO_2$)⁺ base peak; m/z=114 $C_6H_{12}NO^+$ Stage 26(b): 1-{3-[3-(4-Chloro-1H-pyrrolo[2,3-b]pyridin-2-yl)-5,6-dimethoxypyrrolo[3,2-b]pyridin-1-yl]propyl}piperidin-4-ol 1-{3-[3-(4-Chloro-1H-pyrrolo[2,3-b]pyridin-2-yl)-5,6-dimethoxypyrrolo[3,2-b]pyridin-1-yl]propyl}piperidin-4-ol can be prepared as in example 5, stage 5(d), but starting with 0.368 g of 1-(3-{3-[4-chloro-1-(toluene-4-sulfonyl)-1H-pyrrolo[2,3-b]pyridin-2-yl]-5,6-dimethoxypyrrolo[3,2-b]pyridin-1-yl}propyl)-piperidin-4-ol and 0.857 g of potassium hydroxide in 25 cm³ of methanol. 0.188 g of 2-(1-{3-[3-(4-chloro-1H-pyrrolo[2,3-b]pyridin-2-yl)-5,6-dimethoxypyrrolo[3,2-b]pyridin-1-yl]propyl}piperidin-4-yl)ethanol is thus obtained with the following characteristics:

¹H NMR spectrum (300 MHz)—δ in ppm—in DMSO-d6: 1.42 (m, 2H); 1.72 (m, 2H); from 1.88 to 2.02 (m, 4H); 2.21 (t, J=6.5 Hz, 2H); 2.66 (m, 2H); 3.43 (m, 1H); 3.88 (s, 3H); 4.05 (s, 3H); 4.23 (t, J=6.5 Hz, 2H); 4.52 (d, J=3.5 Hz, 1H); 7.12 (d, J=5.5 Hz, 1H); 7.22 (d, J=2.0 Hz, 1H); 7.58 (s, 1H); 8.03 (s, 1H); 8.05 (d, J=5.5 Hz, 1H); 12.05 (broad s, 1H).

Mass spectrum: IE m/z=469 M⁺; m/z=342 (M-$C_7H_{13}$NO)⁺ base peak; m/z=114 $C_6H_{12}NO^+$

EXAMPLE 27

{3-[3-(4-Chloro-1H-pyrrolo[2,3-b]pyridin-2-yl)-5,6-dimethoxypyrrolo[3,2-b]pyridin-1-yl]-propyl}diethylamine Stage 27(a): (3-{3-[4-Chloro-1-(toluene-4-sulfonyl)-1H-pyrrolo[2,3-b]pyridin-2-yl]-5,6-dimethoxypyrrolo[3,2-b]pyridin-1-yl}propyl)diethylamine (3-{3-[4-Chloro-1-(toluene-4-sulfonyl)-1H-pyrrolo[2,3-b]pyridin-2-yl]-5,6-dimethoxypyrrolo[3,2-b]pyridin-1-yl}propyl)diethylamine can be prepared as in example 5, stage 5(c), but starting with 0.15 g of 1-(3-iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine and 0.101 g of diethylamine in 3 cm³ of dimethylformamide. 0.11 g of (3-{3-[4-chloro-1-(toluene-4-sulfonyl)-1H-pyrrolo[2,3-b]pyridin-2-yl]-5,6-dimethoxypyrrolo[3,2-b]pyridin-1-yl}propyl)diethylamine is thus obtained with the following characteristics:

Mass spectrum: IE m/z=595 M$^+$; m/z=496 (M-C$_6$H$_{13}$N)$^+$; m/z=341 (m/z=496-C$_7$H$_7$SO$_2$)$^+$ base peak; m/z=86 C$_5$H$_{12}$N$^+$ Stage 27(b): {3-[3-(4-Chloro-1H-pyrrolo[2,3-b]pyridin-2-yl)-5,6-dimethoxypyrrolo[3,2-b]pyridin-1-yl]propyl}diethylamine {3-[3-(4-Chloro-1H-pyrrolo[2,3-b]pyridin-2-yl)-5,6-dimethoxypyrrolo[3,2-b]pyridin-1-yl]propyl}diethylamine can be prepared as in example 5, stage 5(d), but starting with 0.11 g of (3-{3-[4-chloro-1-(toluene-4-sulfonyl)-1H-pyrrolo[2,3-b]pyridin-2-yl]-5,6-dimethoxypyrrolo[3,2-b]pyridin-1-yl}propyl)diethylamine and 0.228 g of potassium hydroxide in 30 cm³ of methanol. 0.06 g of 3-[3-(4-chloro-1H-pyrrolo[2,3-b]pyridin-2-yl)-5,6-dimethoxypyrrolo[3,2-b]pyridin-1-yl]propyl}diethylamine is thus obtained with the 15 following characteristics:

$^1$H NMR spectrum (300 MHz)—δ in ppm—in DMSO-d6: 0.93 (t, J=7.0 Hz, 6H); 1.93 (m, 2H); 2.37 (t, J=7.0 Hz, 2H); 2.45 (partially masked q, J=7.0 Hz, 4H); 3.87 (s, 3H); 4.05 (s, 3H); 4.23 (t, J=7.0 Hz, 2H); 7.12 (d, J=5.5 Hz, 1H); 7.24 (broad s, 1H); 7.59 (s, 1H); 8.04 (s, 1H); 8.05 (d, J=5.5 Hz, 1H); 12.1 (broad s, 1H).

Mass spectrum: IE m/z=441 M$^+$; m/z=342 (M-C$_6$H$_{13}$N)$^+$ base peak; m/z=86 C$_5$H$_{12}$N$^+$

EXAMPLE 28

C-(1-{3-[3-(4-Chloro-1H-pyrrolo[2,3-b]pyridin-2-yl)-5,6-dimethoxypyrrolo[3,2-b]pyridin-1-yl]propyl}piperidin-4-yl)methylamine Stage 28(a): C-[1-(3-{3-[4-Chloro-1-(toluene-4-sulfonyl)-1H-pyrrolo[2,3-b]pyridin-2-yl]-5,6-dimethoxy-pyrrolo[3,2-b]pyridin-1-yl}propyl)piperidin-4-yl]-methylamine C-[1-(3-{3-[4-Chloro-1-(toluene-4-sulfonyl)-1H-pyrrolo[2,3-b]pyridin-2-yl]-5,6-dimethoxypyrrolo[3,2-b]-pyridin-1-yl}propyl)piperidin-4-yl]methylamine can be prepared as in example 5, stage 5(c), but starting with 0.30 g of 1-(3-iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine and 0.526 g of 4-aminomethylpiperidine in 30 cm³ of dichloromethane. 0.207 g of (C-[1-(3-{3-[4-chloro-1-(toluene-4-sulfonyl)-1H-pyrrolo[2,3-b]pyridin-2-yl]-5,6-dimethoxypyrrolo[3,2-b]pyridin-1-yl}propyl)piperidin-4-yl]methylamine is thus obtained with the following characteristics:

Rf TLC silica [eluent: chloroform/methanol/ammonia (12/3/0.5 by volume)]=0.39
Mass spectrum: IC m/z=637 MH$^+$ base peak Stage 28(b): C-(1-{3-[3-(4-Chloro-1H-pyrrolo[2,3-b]pyridin-2-yl)-5,6-dimethoxypyrrolo[3,2-b]pyridin-1-yl]-propyl}piperidin-4-yl)methylamine C-(1-{3-[3-(4-Chloro-1H-pyrrolo[2,3-b]pyridin-2-yl)-5,6-dimethoxypyrrolo[3,2-b]pyridin-1-yl]propyl}piperidin-4-yl)methylamine can be prepared as in example 5, stage 5(d), but starting with 0.26 g of C-[1-(3-{3-[4-chloro-1-(toluene-4-sulfonyl)-1H-pyrrolo[2,3-b]pyridin-2-yl]-5,6-dimethoxy-pyrrolo[3,2-b]pyridin-1-yl}propyl)piperidin-4-yl]methylamine and 0.458 g of potassium hydroxide in 50 cm³ of methanol. 0.108 g of C-(1-{3-[3-(4-chloro-1H-pyrrolo[2,3-b]pyridin-2-yl)-5,6-dimethoxypyrrolo[3,2-b]pyridin-1-yl]propyl}piperidin-4-yl)methylamine is thus obtained with the following characteristics:

$^1$H NMR spectrum (300 MHz)—δ in ppm—in DMSO-d6: from 1.03 to 1.18 (m, 3H); 1.66 (m, 2H); 1.80 (m, 2H); 1.96 (m, 2H); 2.21 (t, J=6.5 Hz, 2H); 2.39 (d, J=5.5 Hz, 2H); 2.80 (m, 2H); 3.87 (s, 3H); 4.05 (s, 3H); 4.21 (t, J=6.5 Hz, 2H); 7.12 (d, J=5.5 Hz, 1H); 7.25 (s, 1H); 7.58 (s, 1H); 8.02 (s, 1H); 8.06 (d, J=5.5 Hz, 1H); 12.0 (broad m, 1H).

Mass spectrum: IE m/z=482 M$^+$; m/z=342 (M-C$_8$H$_{16}$N$_2$)$^+$ base peak

EXAMPLE 29

3-(4-Chloro-1H-pyrrolo[2,3-b]pyridin-2-yl)-5,6-dimethoxy-1-[3-(4-methylperhydro-1,4-diazepin-1-yl)propyl]-1H-pyrrolo[3,2-b]pyridine Stage 29(a): 3-[4-Chloro-1-(toluene-4-sulfonyl)-1H-pyrrolo[2,3-b]pyridin-2-yl]-5,6-dimethoxy-1-[3-(4-methylperhydro-1,4-diazepin-1-yl)propyl]-1H-pyrrolo[3,2-b]pyridine 3-[4-Chloro-1-(toluene-4-sulfonyl)-1H-pyrrolo[2,3-b]pyridin-2-yl]-5,6-dimethoxy-1-[3-(4-methylperhydro-1,4-diazepin-1-yl)propyl]-1H-pyrrolo[3,2-b]pyridine can be prepared as in example 5, stage 5(c), but starting with 0.835 g of 1-(3-iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine and 1.59 cm³ (12.8 mmol) of 1-methylperhydro-1,4-diazepine in 40 cm³ of dichloromethane. 0.32 g of 3-[4-chloro-1-(toluene-4-sulfonyl)-1H-pyrrolo[2,3-b]pyridin-2-yl]-5,6-dimethoxy-1-[3-(4-methylperhydro-1,4-diazepin-1-yl)propyl]-1H-pyrrolo[3,2-b]pyridine is thus obtained with the following characteristics:

Rf TLC silica [eluent: dichloromethane/methanol (90/10 by volume)]=0.2
Mass spectrum: ES m/z=637 MH$^+$ base peak Stage 29(b): 3-(4-Chloro-1H-pyrrolo[2,3-b]pyridin-2-yl)-5,6-dimethoxy-1-[3-(4-methylperhydro-1,4-diazepin-1-yl)propyl]-1H-pyrrolo[3,2-b]pyridine 3-(4-Chloro-1H-pyrrolo[2,3-b]pyridin-2-yl)-5,6-dimethoxy-1-[3-(4-methylperhydro-1,4-diazepin-1-yl)-propyl]-1H-pyrrolo[3,2-b]pyridine can be prepared as in example 5, stage 5(d), but starting with 0.32 g of 3-[4-chloro-1-(toluene-4-sulfonyl)-1H-pyrrolo[2,3-b]pyridin-2-yl]-5,6- dimethoxy-1-[3-(4-methylperhydro-1,4-diazepin-1-yl)propyl]-1H-pyrrolo[3,2-b]pyridine and 0.62 g of potassium hydroxide in 25 cm³ of methanol. 0.015 g of 3-(4-chloro-1H-pyrrolo[2,3-b]pyridin-2-yl)-5,6-dimethoxy-1-[3-(4-methylperhydro-1,4-diazepin-1-yl)propyl]-1H-pyrrolo[3,2-b]pyridine is thus obtained with the following characteristics:

$^1$H NMR spectrum (300 MHz)—δ in ppm—in DMSO-d6: 1.70 (m, 2H); 1.93 (m, 2H); 2.23 (s, 3H); 2.39 (broad t, J=6.5 Hz, 2H); from 2.43 to 2.55 (partially masked m, 4H); 2.60 (m, 4H); 3.88 (s, 3H); 4.05 (s, 3H); 4.24 (broad t, J=6.5 Hz, 2H); 7.12 (d, J=5.5 Hz, 1H); 7.24 (broad s, 1H); 7.58 (s, 1H); 8.02 (s, 1H); 8.05 (d, J=5.5 Hz, 1H); 12.05 (broad s, 1H).

Mass spectrum: ES m/z=483 MH+; m/z=242 (M+2H)2+/2 base peak

EXAMPLE 30

3-(4-Chloro-1H-pyrrolo[2,3-b]pyridin-2-yl)-5,6-dimethoxy-1-(3-piperidin-1-ylpropyl)-1H-pyrrolo[3,2-b]pyridine Stage 30(a): 3-[4-Chloro-1-(toluene-4-sulfonyl)-1H-pyrrolo[2,3-b]pyridin-2-yl]-5,6-dimethoxy-1-(3-piperidin-1-ylpropyl)-1H-pyrrolo[3,2-b]pyridine 3-[4-Chloro-1-(toluene-4-sulfonyl)-1H-pyrrolo[2,3-b]pyridin-2-yl]-5,6-dimethoxy-1-(3-piperidin-1-yl-propyl)-1H-pyrrolo[3,2-b]pyridine can be prepared as in example 5, stage 5(c), but starting with 0.835 g of 1-(3-iodopropyl)-3-[4-chloro-1-(toluene-4-sulfonyl)-1H-pyrrolo[2,3-b]pyridin-2-yl]-5,6-dimethoxy-1H-pyrrolo[3,2-b]pyridine and 1.26 cm³ of piperidine in 40 cm³ of dichloromethane. 0.39 g of 3-[4-chloro-1-(toluene-4-sulfonyl)-1H-pyrrolo[2,3-b]pyridin-2-yl]-5,6-dimethoxy-1-(3-piperidin-1-ylpropyl)-1H-pyrrolo[3,2-b]pyridine is thus obtained with the following characteristics:

Rf TLC silica [eluent: dichloromethane/methanol (90/10 by volume)]=0.24

Mass spectrum: IE m/z=607 M$^{+\cdot}$; m/z=496 (M-C$_7$H$_{13}$N)$^+$; m/z=452 (M-C$_7$H$_7$SO$_2$)$^+$; m/z=341 (m/z=496-C$_7$H$_7$SO$_2$)$^+$ base peak; m/z=98 C$_6$H$_{12}$N$^+$ Stage 30(b): 3-(4-Chloro-1H-pyrrolo[2,3-b]pyridin-2-yl)-5,6-dimethoxy-1-(3-piperidin-1-ylpropyl)-1H-pyrrolo[3,2-b]pyridine 3-(4-Chloro-1H-pyrrolo[2,3-b]pyridin-2-yl)-5,6-dimethoxy-1-(3-piperidin-1-ylpropyl)-1H-pyrrolo(3,2-b]pyridine can be prepared as in example 5, stage 5(d), but starting with 0.39 g of 3-[4-chloro-1-(toluene-4-sulfonyl)-1H-pyrrolo[2,3-b]pyridin-2-yl]-5,6-dimethoxy-1-(3-piperidin-1-yl-propyl)-1H-pyrrolo[3,2-b]pyridine and 0.792 g of potassium hydroxide in 25 cm³ of methanol. 0.035 g of 3-(4-chloro-1H-pyrrolo[2,3-b]pyridin-2-yl)-5,6-dimethoxy-1-(3-piperidin-1-ylpropyl)-1H-pyrrolo[3,2-b]pyridine is thus obtained with the following characteristics:

$^1$H NMR spectrum (300 MHz)—δ in ppm—in DMSO-d6: 1.38 (m, 2H); 1.51 (m, 4H); 1.95 (m, 2H); 2.20 (t, J=7.0 Hz, 2H); 2.28 (broad m, 4H); 3.88 (s, 3H); 4.05 (s, 3H); 4.23 (t, J=7.0 Hz, 2H); 7.12 (d, J=5.5 Hz, 1H); 7.24 (d, J=2.0 Hz, 1H); 7.59 (s, 1H); 8.03 (s, 1H); 8.05 (d, J=5.5 Hz, 1H); 12.05 (broad s, 1H).

Mass spectrum: ES m/z=454 MH$^+$; m/z=227.8 (M+2H)$^{2+}$/2 base peak

EXAMPLE 31

2-(5,6-Dimethoxy-1H-pyrrolo[3,2-b]pyridin-3-yl)-1H-pyrrolo[2,3-b]pyridine-4-carbonitrile Stage 31(a): 1-(Toluene-4-sulfonyl)-2-tributylstannanyl-1H-pyrrolo[2,3-b]pyridine-4-carbonitrile 1-(Toluene-4-sulfonyl)-2-tributylstannanyl-1H-pyrrolo[2,3-b]pyridine-4-carbonitrile can be prepared as in example 4, stage 4(d), but starting with 0.5 g of 1-(toluene-4-sulfonyl)-1H-pyrrolo[2,3-b]pyridine-4-carbonitrile, 1.2 cm³ of n-butyllithium and 0.52 cm³ of tributyltin chloride in 30 cm³ of tetrahydrofuran. 0.56 g of 1-(toluene-4-sulfonyl)-2-tributylstannanyl-1H-pyrrolo[2,3-b]pyridine-4-carbonitrile is thus obtained with the following characteristics:

Rf TLC silica [eluent: cyclohexane/ethyl acetate (75/25 by volume)]=0.57

Mass spectrum: IE m/z=586 M$^+$; m/z=530 (M-C$_4$H$_8$)$^+$. base peak; m/z=416 (m/z=530-2C$_4$H$_9$)$^+$; m/z=262 (m/z=416-C$_7$H$_7$SO$_2$+H)$^{+\cdot}$ 1-(Toluene-4-sulfonyl)-1H-pyrrolo[2,3-b]pyridine-4-carbonitrile is prepared as described in patent WO0147922A2.

Stage 31(b): tert-Butyl 3-[4-cyano-1-(toluene-4-sulfonyl)-1H-pyrrolo[2,3-b]pyridin-2-yl]-5,6-dimethoxy-pyrrolo[3,2-b]pyridine-1-carboxylate tert-Butyl 3-[4-cyano-1-(toluene-4-sulfonyl)-1H-pyrrolo[2,3-b]pyridin-2-yl]-5,6-dimethoxypyrrolo[3,2-b]pyridine-1-carboxylate can be prepared as in example 4, stage 4(e), but starting with 0.56 g of 1-(toluene-4-sulfonyl)-2-tributylstannanyl-1H-pyrrolo[2,3-b]pyridine-4-carbonitrile, 0.35 g of 4-chloro-1-(toluene-4-sulfonyl)-2-tributylstannanyl-1H-pyrrolo[2,3-b]pyridine, 0.0166 g of copper iodide and 0.1 g of tetrakis(triphenylphosphine)palladium in 30 cm³ of toluene. 0.11 g of tert-butyl 3-[4-cyano-1-(toluene-4-sulfonyl)-1H-pyrrolo[2,3-b]pyridin-2-yl]-5,6-dimethoxypyrrolo[3,2-b]pyridine-1-carboxylate is thus obtained with the following characteristics:

Rf TLC silica [eluent: dichloromethane]=0.29

Mass spectrum: ES m/z=574 MH$^+$ base peak

Stage 31(c): 2-(5,6-Dimethoxy-1H-pyrrolo[3,2-b]pyridin-3-yl)-1-(toluene-4-sulfonyl)-1H-pyrrolo[2,3-b]pyridine-4-carbonitrile 2-(5,6-Dimethoxy-1H-pyrrolo[3,2-b]pyridin-3-yl)-1-(toluene-4-sulfonyl)-1H-pyrrolo[2,3-b]pyridine-4-carbonitrile can be prepared as in example 1, stage 1(m), but starting with 0.11 g of tert-butyl 3-[4-cyano-1-(toluene-4-sulfonyl)-1H-pyrrolo[2,3-b]pyridin-2-yl]-5,6-dimethoxypyrrolo[3,2-b]pyridine-1-carboxylate and 1.1 cm³ of trifluoroacetic acid in 25 cm³ of methanol in 5 cm³ of dichloromethane. 0.06 g of 2-(5,6-dimethoxy-1H-pyrrolo[3,2-b]pyridin-3-yl)-1-(toluene-4-sulfonyl)-1H-pyrrolo[2,3-b]pyridine-4-carbonitrile is thus obtained with the following characteristics:

Rf TLC silica [eluent: dichloromethane/methanol (95/5 by volume)]=0.4

Mass spectrum: ES m/z=474 MH+ base peak

Stage 31(d): 2-(5,6-Dimethoxy-1H-pyrrolo[3,2-b]pyridin-3-yl)-1H-pyrrolo[2,3-b]pyridine-4-carbonitrile 2-(5,6-Dimethoxy-1H-pyrrolo[3,2-b]pyridin-3-yl)-1H-pyrrolo[2,3-b]pyridine-4-carbonitrile can be prepared as in example 5, stage 5(d), but starting with 0.06 g of 2-(5,6-dimethoxy-1H-pyrrolo[3,2-b]pyridin-3-yl)-1-(toluene-4-sulfonyl)-1H-pyrrolo[2,3-b]pyridine-4-carbonitrile and 0.156 g of potassium hydroxide in 5 cm³ of methanol. 0.0195 g of 2-(5,6-dimethoxy-1H-pyrrolo[3,2-b]pyridin-3-yl)-1H-pyrrolo[2,3-b]pyridine-4-carbonitrile is thus obtained with the following characteristics:

$^1$H NMR spectrum (300 MHz)—δ in ppm—in DMSO-d6: 3.85 (s, 3H); 4.06 (s, 3H); 7.38 (s, 1H); 7.41 (s, 1H); 7.42 (d, J=5.5 Hz, 1H); 8.09 (s, 1H); 8.23 (d, J=5.5 Hz, 1H); 11.5 (broad m, 1H); 12.4 (broad s, 1H)

Mass spectrum: IE m/z=319 M$^+$. base peak; m/z=304 (M-CH$_3$)$^+$

EXAMPLE 32

2-(5,6-Dimethoxy-1-methyl-1H-pyrrolo[3,2-b]pyridin-3-yl)-1H-pyrrolo[2,3-b]pyridine-4-carbonitrile

Stage 32(a): 2-(5,6-Dimethoxy-1-methyl-1H-pyrrolo[3,2-b]pyridin-3-yl)-1-(toluene-4-sulfonyl)-1H-pyrrolo-[2,3-b]pyridine-4-carbonitrile 2-(5,6-Dimethoxy-1-methyl-1H-pyrrolo[3,2-b]pyridin-3-yl)-1-(toluene-4-sulfonyl)-1H-pyrrolo[2,3-b]pyridine-4-carbonitrile can be prepared as in example 1, stage 1(n), but starting with 0.1 g of 2-(5,6-dimethoxy-1H-pyrrolo[3,2-b]pyridin-3-yl)-1-(toluene-4-sulfonyl)-1H-pyrrolo[2,3-b]pyridine-4-carbonitrile, 0.010 g of sodium hydride and 0.016 cm³ of methyl iodide in 5 cm³ of dimethylformamide.

0.09 g of 2-(5,6-dimethoxy-1-methyl-1H-pyrrolo[3,2-b]pyridin-3-yl)-1-(toluene-4-sulfonyl)-1H-pyrrolo[2,3-b]pyridine-4-carbonitrile is thus obtained with the following characteristics:

Rf TLC silica [eluent: dichloromethane/methanol (98/2 by volume)]=0.31

Mass spectrum: IE m/z=487 M$^+$; m/z=332 (M-C$_7$H$_7$SO$_2$)$^+$ base peak

Stage 32(b): 2-(5,6-Dimethoxy-1-methyl-1H-pyrrolo[3,2-b]-pyridin-3-yl)-1H-pyrrolo[2,3-b]pyridine-4-carbonitrile 2-(5,6-Dimethoxy-1-methyl-1H-pyrrolo[3,2-b]pyridin-3-yl)-1H-pyrrolo[2,3-b]pyridine-4-carbonitrile can be prepared as in example 5, stage 5(d), but starting with 0.09 g of 2-(5,6-dimethoxy-1-methyl-1H-pyrrolo[3,2-b]pyridin-3-yl)-1-(toluene-4-sulfonyl)-1H-pyrrolo[2,3-b]pyridine-4-carbonitrile and 0.228 g of potassium hydroxide in 5 cm³ of methanol. 0.02 g of 2-(5,6-dimethoxy-1-methyl-1H-pyrrolo[3,2-b]pyridin-3-yl)-1H-pyrrolo[2,3-b]pyridine-4-carbonitrile is thus obtained with the following characteristics:

$^1$H NMR spectrum (300 MHz)—δ in ppm—in DMSO-d6: 3.87 (s, 3H); 3.89 (s, 3H); 4.06 (s, 3H); 7.36 (s, 1H); 7.42 (d, J=5.5 Hz, 1H); 7.63 (s, 1H); 8.03 (s, 1H); 8.23 (d, J=5.5 Hz, 1H); 12.4 (broad m, 1H)

Mass spectrum: IE m/z=333 M$^+$. base peak; m/z=318 (M-CH$_3$)$^+$

EXAMPLE 33

2-[3-(4-Chloro-1H-pyrrolo[2,3-b]pyridin-2-yl)-5,6-dimethoxypyrrolo[3,2-b]pyridin-1-yl]-N-methoxy-N-methyl-acetamide 2-[3-(4-Chloro-1H-pyrrolo[2,3-b]pyridin-2-yl)-5,6-dimethoxypyrrolo[3,2-b]pyridin-1-yl]-N-methoxy-N-methylacetamide is prepared in the following manner:

To a solution of 1.8 g of {3-(4-chloro-1H-pyrrolo[2,3-b]pyridin-2-yl)-5,6-dimethoxypyrrolo[3,2-b]pyridin-1-yl]}carboxylic acid in 30 cm³ of dimethylformamide and 30 cm³ of 1-,2-dichloroethane, at a temperature in the region of 20° C., is added 0.692 g of 1-hydroxybenzotriazole and 0.981 g of 1-(dimethyl-aminopropyl)-3-ethylcarbodiimide hydrochloride. The reaction medium is stirred at this same temperature for 1 hour. 0.5 g of N,O-dimethylhydroxylamine hydrochloride and then 2.2 cm³ of triethylamine are added. After stirring for 20 hours at the same temperature, 100 cm³ of dichloromethane are added, the organic phase is washed with 3 times 100 cm³ of saturated aqueous sodium hydrogencarbonate solution and then with twice 100 cm³ of water. After separation of the phases by settling, the organic phase is dried over magnesium sulfate, filtered and then concentrated under reduced pressure. The residue obtained is purified by flash chromatography (silica, dichloromethane/methanol, 98/02 by volume). The fractions containing the product are concentrated under reduced pressure. 2.11 g of crude 2-[3-(4-chloro-1H-pyrrolo[2,3-b]pyridin-2-yl)-5,6-dimethoxypyrrolo[3,2-b]pyridin-1-yl]-N-methoxy-N-methylacetamide are thus obtained. 0.1 g of this solid is taken up in 2 cm³ of pentane and then filtered off and drained by suction. The cake is then washed with twice 1 cm³ of pentane and then oven-dried at 35° C. for 8 hours. 0.062 g of 2-[3-(4-chloro-1H-pyrrolo[2,3-b]pyridin-2-yl)-5,6-dimethoxy-pyrrolo[3,2-b]pyridin-1-yl]-N-methoxy-N-methyl-acetamide is thus obtained with the following characteristics:

$^1$H NMR spectrum (300 MHz)—δ in ppm—in DMSO-d6: 3.18 (broad s, 3H); 3.85 (s, 3H); 3.86 (broad s, 3H); 4.05 (s, 3H); 5.29 (broad s, 2H); 7.14 (d, J=5.5 Hz, 1H); 7.27 (d, J=2.0 Hz, 1H); 7.59 (s, 1H); 7.93 (s, 1H); 8.06 (d, J=5.5 Hz, 1H); 12.1 (broad m, 1H).

Mass spectrum: IE m/z=429 M$^+$. base peak; m/z=399 (M-OCH$_3$+H)$^+$; m/z=341 (M-C$_3$H$_6$NO$_2$)$^+$.

EXAMPLE 34

Cyclopropyl-[2-(5,6-dimethoxy-1-methyl-1H-pyrrolo[3,2-b]pyridin-3-yl)-1H-pyrrolo[2,3-b]pyridin-4-ylmethyl]amine

Stage 34(a): 4-Cyano-1-(toluene-4-sulfonyl)-1H-pyrrolo[2,3-b]pyridine

To a solution of 10 g of 4-chloro-1-(toluene-4-sulfonyl)-1H-pyrrolo[2,3-b]pyridine in 200 cm³ of N,N-dimethylacetamide, under an inert atmosphere of argon, are added 6.9 g of zinc cyanide and 1.07 g of zinc powder. After stirring for 45 minutes at a temperature in the region of 20° C., 2.4 g of PdCl$_2$, dppf are added. The reaction medium is heated at a temperature in the region of 140° C. for 1 hour 30 minutes. After cooling, the reaction medium is filtered through Celite and then rinsed with dichloromethane. 150 cm³ of water are added to the filtrate. After separation of the phases by settling, the organic phase is dried over sodium sulfate, filtered and then concentrated under reduced pressure. After purification by flash chromatography on a column (SiO$_2$, cyclohexane/ethyl acetate, 75/25 by volume as eluent, Ar), 8.57 g of 4-cyano-1-(toluene-4-sulfonyl)-1H-pyrrolo[2,3-b]pyridine are obtained with the following characteristics:

Mass spectrum: IE m/z=297 M$^+$; m/z=233 (M-SO$_2$)+.; m/z=91; C$_7$H$_7$+ base peak The compound 1-tosyl-4-chloropyrrolo[2,3-b]pyridine is prepared according to the process described in patent WO 03/000688 A1.

Stage 34(b): 4-Carbaldehyde-1-(toluene-4-sulfonyl)-1H-pyrrolo[2,3-b]pyridine To a solution of 10 g of 1-tosyl-4-cyanoazaindole in 400 cm$^3$ of toluene, under an inert atmosphere of argon at a temperature in the region of −30° C., are added dropwise 50.5 cm$^3$ of DIBAH as a 20% by weight solution in toluene (1M). After stirring for 40 minutes at this same temperature, the cooling bath is removed. The temperature is allowed to rise to 20° C. The reaction medium is stirred at a temperature in the region of 20° C. for 1 hour. The reaction medium is cooled to 4° C. 1N hydrochloric acid is added dropwise to pH =6. The precipitate formed is filtered off and then washed with 50 cm$^3$ of water and 280 cm$^3$ of ethyl acetate. After separation of the filtrate by settling, the organic phase is dried over sodium sulfate, filtered, concentrated under reduced pressure and then purified by flash chromatography on a column (SiO$_2$, dichloromethane as eluent, Ar). The fractions containing the product are concentrated under reduced pressure. 4.3 g of 4-carbaldehyde-1-(toluene-4-sulfonyl)-1H-pyrrolo[2,3-b]pyridine are thus obtained with the following characteristics:

Mass spectrum: IE m/z=300 M$^+$; m/z=236 (M-SO$_2$)+.; m/z=91; C$_7$H$_7^+$ base peak

Stage 34(c): 4-(1,3-Dioxolan)-2-yl-1-(toluene-4-sulfonyl)-1H-pyrrolo[2,3-b]pyridine To a solution of 5.8 g of 4-carbaldehyde-1-(toluene-4-sulfonyl)-1H-pyrrolo[2,3-b]pyridine in 250 cm$^3$ of toluene, under an inert atmosphere of argon, are added 2.15 cm$^3$ of ethylene glycol and 0.735 g of para-toluenesulfonic acid. The reaction medium is heated at 120° C. for 3 hours. After cooling, 50 cm$^3$ of water and 50 cm$^3$ of ethyl acetate are added. After separation of the phases by settling, the organic phase is dried over sodium sulfate, filtered and then concentrated under reduced pressure. The residue obtained is triturated with ethyl ether. The solid obtained is filtered off and then washed with 20 cm$^3$ of ethyl ether. 5.3 g of 4-(1,3-dioxolan)-2-yl-1-(toluene-4-sulfonyl)-1H-pyrrolo[2,3-b]pyridine are thus obtained with the following characteristics:

Mass spectrum: IE m/z=344 M$^+$; m/z=237 (M-C$_7$H$_7$SO$_2$)$^+$ base peak; m/z=91 C$_7$H$_7^+$

Stage 34(d): 4-(1,3-Dioxolan)-2-yl-2-iodo-1-(toluene-4-sulfonyl)-1H-pyrrolo[2,3-b]pyridine To a solution of 5 g of 4-(1,3-dioxolan)-2-yl-1-(toluene-4-sulfonyl)-1H-pyrrolo[2,3-b]pyridine in 100 cm$^3$ of anhydrous tetrahydrofuran, under an inert atmosphere of argon at a temperature in the region of −78° C., are added dropwise 5.81 cm$^3$ of n-BuLi (2.5M in hexane). The reaction medium is stirred at this same temperature for 25 minutes, followed by dropwise addition of a solution of 7.37 g of iodine in 50 cm$^3$ of tetrahydrofuran. The reaction medium is stirred at −78° C. for 15 minutes. The cooling bath is removed. The temperature returns to room temperature after stirring for 2 hours. The reaction medium is stirred at room temperature for 20 hours. 15 cm$^3$ of water and 15 cm$^3$ of ethyl acetate are added. After separation of the phases by settling, the organic phase is dried over sodium sulfate, filtered and then concentrated under reduced pressure. The residue obtained is purified by flash chromatography (SiO$_2$, dichloromethane as eluent, argon). The fractions containing the product are concentrated under reduced pressure. 6.28 g of 4-(1,3-dioxolan)-2-yl-2-iodo-1-(toluene-4-sulfonyl)-1H-pyrrolo[2,3-b]pyridine are thus obtained with the following characteristics:

Mass spectrum: ES m/z=471 MH$^+$; base peak

Stage 34(e): 1-t-butyloxycarbonyl-3-iodo-5,6-dimethoxy-1H-pyrrolo[3,2-b]pyridine To a solution of 8 g of 5,6-dimethoxy-1H-pyrrolo[3,2-b]pyridine in 150 cm$^3$ of DMF, under an inert atmosphere of argon at a temperature in the region of 20° C., are added dropwise 12 g of iodine in 150 cm$^3$ of DMF. The reaction medium is stirred at this same temperature for 2 hours, and a solution of 11.8 g of di-tert-butyl dicarbonate in 100 cm$^3$ of DMF is then added dropwise. The reaction medium is stirred at this same temperature for 1 hour. The reaction medium is poured onto 300 cm$^3$ of ice-water. The solid formed is filtered off on a sinter funnel and then washed with water. The solid is taken up in 250 cm$^3$ of dichloromethane. After separation of the phases by settling, the organic phase is dried over sodium sulfate, filtered and then concentrated under reduced pressure. 16.7 g of 1-t-butyloxycarbonyl-3-iodo-5,6-dimethoxy-1H-pyrrolo[3,2-b]pyridine are thus obtained with the following characteristics:

Mass spectrum: ES m/z=405 MH$^+$; m/z=349 (M-C$_4$H$_8$+H)$^+$ base peak

Stage 34(f): 1-t-Butyloxycarbonyl-5,6-dimethoxy-1H-pyrrolo[3,2-b]pyridine-3-boronic acid To a solution of 16.6 g of 1-t-butyloxycarbonyl-3-iodo-5,6-dimethoxy-1H-pyrrolo[3,2-b]pyridine in 300 cm$^3$ of anhydrous tetrahydrofuran, under an inert atmosphere of argon at a temperature in the region of −100° C., are added dropwise 14.41 cm$^3$ of tributyl borate followed by 41 cm$^3$ of n-BuLi (1.6M in hexane). The reaction medium is stirred at this same temperature for 90 minutes. The cooling bath is removed. The temperature rises to −5° C. 100 g of ice are added, followed by 100 cm$^3$ of water and 300 cm$^3$ of ethyl acetate. After separation of the phases by settling, the organic phase is dried over sodium sulfate, filtered and then concentrated under reduced pressure. The residue obtained is purified by chromatography (SiO$_2$, dichloromethane/methanol 98/02 by volume as eluents, argon). The fractions containing the product are concentrated under reduced pressure. 8.32 g of 1-t-butyloxycarbonyl-5,6-dimethoxy-1H-pyrrolo[3,2-b]pyridin-3-boronic acid are thus obtained with the following characteristics:

Mass spectrum: ES m/z=323 MH$^+$; m/z=267 (M-C$_4$H$_8$+H)$^+$ base peak

Stage 34(g): 2-(5,6-Dimethoxy-1H-pyrrolo[3,2-b]pyridin-3-yl)-4-(1,3-dioxolan)-2-yl-1-(toluene-4-sulfonyl)-1H-pyrrolo[2,3-b]pyridine To a solution of 12.12 g of 4-(1,3-dioxolan)-2-yl-2-iodo-1-(toluene-4-sulfonyl)-1H-pyrrolo[2,3-b]pyridine, 240 cm$^3$ of anhydrous DMF and 8.3 g of 1-t-butyloxycarbonyl-5,6-dimethoxy-1H-pyrrolo[3,2-b]pyridin-3-boronic acid, under an inert atmosphere of argon at a temperature in the region of 20° C., are added 60 cm³ of saturated sodium bicarbonate solution and 1.49 g of tetrakis(triphenylphosphine)palladium. The reaction medium is heated at 130° C. for 3 hours. After cooling, the reaction medium is concentrated under reduced pressure. The oil obtained is taken up in 150 cm³ of water and 100 cm³ of ethyl acetate. After separation of the phases by settling, the organic phase is dried over sodium sulfate, filtered and then concentrated under reduced pressure. The residue obtained is purified by flash chromatography (SiO₂, ethyl acetate/dichloromethane 10/90 by volume as eluents, argon). The fractions containing the product are concentrated under reduced pressure. 11.18 g of 2-(5,6-dimethoxy-1H-pyrrolo[3,2-b]pyridin-3-yl)-4-(1,3-dioxolan)-2-yl-1-(toluene-4-sulfonyl)-1H-pyrrolo[2,3-b]pyridine are thus obtained with the following characteristics:

Mass spectrum: ES m/z=521 MH⁺; base peak

Stage 34(h): 2-(5,6-dimethoxy-1-methyl-1H-pyrrolo [3,2-b]pyridin-3-yl)-4-(1,3-dioxolan)-2-yl-1-(toluene-4-sulfonyl)-1H-pyrrolo[2,3-b]pyridine To a solution of 13.5 g of 2-(5,6-dimethoxy-1H-pyrrolo[3, 2-b]pyridin-3-yl)-4-(1,3-dioxolan)-2-yl-1-(toluene-4-sulfonyl)-1H-pyrrolo[2,3-b]pyridine in 450 cm³ of anhydrous dimethylformamide (DMF), under an inert atmosphere of argon at a temperature in the region of 20° C., are added 1.25 g of sodium hydride as a 60% suspension in oil. The reaction medium is stirred at the same temperature for 45 minutes. 1.94 cm³ of methyl iodide are added dropwise. The reaction medium is stirred at this same temperature for 3 hours. 900 cm³ of water and 400 cm³ of ethyl acetate are added. After separation of the phases by settling, the organic phase is dried over magnesium sulfate, filtered and then concentrated under reduced pressure. The solid obtained is triturated in ethyl ether and then filtered off and dried to give 13.3 g of 2-(5,6-dimethoxy-1-methyl-1H-pyrrolo[3,2-b]pyridin-3-yl)-4-(1, 3-dioxolan)-2-yl-1-(toluene-4-sulfonyl)-1H-pyrrolo[2,3-b] pyridine with the following characteristics:

Mass spectrum: IE m/z=534 M⁺. base peak; m/z=379(M-C₇H₇SO₂)⁺

Stage 34(i): 2-(5,6-dimethoxy-1-methyl-1H-pyrrolo [3,2-b]pyridin-3-yl)-1-(toluene-4-sulfonyl)-1H-pyrrolo[2,3-b]pyridin-4-carbaldehyde To a solution of 13.2 g of 2-(5,6-dimethoxy-1-methyl-1H-pyrrolo[3,2-b]pyridin-3-yl)-4-(1,3-dioxolan)-2-yl-1-(toluene-4-sulfonyl)-1H-pyrrolo[2,3-b]pyridine in 250 cm³ of tetrahydrofuran, at a temperature in the region of 20° C., are added 49.4 cm³ of 5N hydrochloric acid. The reaction medium is stirred at this same temperature for 5 hours. 100 cm³ of water and 200 cm³ of dichloromethane are added. After separation of the phases by settling, the organic phase is dried over magnesium sulfate, filtered, concentrated under reduced pressure and then purified on a column of silica, eluting with a 95/05 by volume mixture of dichloromethane and ethyl acetate. The fractions containing the product are combined and concentrated to dryness under reduced pressure to give 9.9 g of 2-(5,6-dimethoxy-1-methyl-1H-pyrrolo [3,2-b]pyridin-3-yl)-1-(toluene-4-sulfonyl)-1H-pyrrolo[2,3-b]pyridin-4-carbaldehyde with the following characteristics:

Mass spectrum: ES m/z=491 MH⁺; base peak; m/z=336 (M-C₇H₇SO₂+H)⁺

Stage 34(j): Preparation of cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine To a solution of 0.141 cm³ of cyclopropylamine in 6 cm³ of dichloromethane, under an inert atmosphere of argon at a temperature in the region of 20° C., are added 0.2 g of 2-(5, 6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.4 g of sodium sulfate. Stirring is continued for 48 hours at room temperature. 6 cm³ of methanol and 0.031 g of sodium borohydride are added. The reaction medium is stirred at the same temperature for 24 hours. 100 cm³ of dichloromethane are added. The precipitate formed is filtered off and the filtrate is concentrated under reduced pressure and then purified by flash column chromatography (SiO₂, dichloromethane/ethyl acetate 80/20 by volume as eluents) to give 0.110 g of cyclopropyl-[2-(5,6-dimethoxy-1-methyl-1H-pyrrolo[3,2-b]pyridin-3-yl)-1-(toluene-4-sulfonyl)-1H-pyrrolo [2,3-b]pyridin-4-ylmethyl]-amine with the following characteristics:

Mass spectrum: IE m/z=531 M⁺; m/z=475 (M-C₃H₆N)⁺; m/z=376 (M-C₇H₇SO₂)⁺; m/z=321 (m/z=376-C₃H₆N)⁺ base Stage 34(k): Cyclopropyl-[2-(5,6-dimethoxy-1-methyl-1H-pyrrolo[3,2-b]pyridin-3-yl)-1H-pyrrolo[2,3-b]pyridin-4-ylmethyl]amine To a solution of 0.11 g of cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine in 20 cm³ of methanol, at a temperature in the region of 20° C., is added 1 cm³ of 5N potassium hydroxide. The reaction medium is refluxed for 24 hours. After cooling, the reaction medium is concentrated under reduced pressure. The residue obtained is taken up in 20 cm³ of water. The solid formed is filtered off on a sinter funnel. The solid obtained is taken up in 80 cm³ of dichloromethane and 3 cm³ of water. The organic phase is dried over magnesium sulfate, filtered and then concentrated under reduced pressure to give 0.075 g of cyclopropyl-[2-(5,6-dimethoxy-1-methyl-1H-pyrrolo[3,2-b]pyridin-3-yl)-1H-pyrrolo[2,3-b]pyridin-4-ylmethyl]amine with the following characteristics:

¹H NMR spectrum (300 MHz, (CD₃)₂SO d6, δ in ppm): 0.32 (m, 2H); 0.38 (m, 2H); 2.15 (m, 1H); 3.84 (s, 3H); 3.88 (s, 3H); 4.01 (broad s, 2H); 4.07 (s, 3H); 6.99 (d, J=5.5 Hz, 1H); 7.29 (d, J=2.0 Hz, 1H); 7.58 (s, 1H); 7.89 (s, 1H); 8.03 (d, J=5.5 Hz, 1H); 11.6 (broad m, 1H).

Mass spectrum: IE m/z=377 M⁺; m/z=321 (M-C₃H₆N)⁺. base peak

EXAMPLE 35

[2-(5,6-Dimethoxy-1-methyl-1H-pyrrolo[3,2-b]pyridin-3-yl)-1H-pyrrolo[2,3-b]pyridin-4-ylmethyl]-(4-morpholin-4-yl-phenyl)amine Stage 35(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-ylmethyl]-(4-morpholin-4-yl-phenyl)amine The product is prepared by following the procedure described in example 34, stage (j), starting with 0.15 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.272 g of 4-morpholin-4-ylphenylamine instead of the cyclopropylamine used in example 34, stage (j). After purification by flash-pack chromatography (SiO$_2$, dichloromethane/ethyl acetate 80/20 by volume as eluents), 0.06 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(4-morpholin-4-yl-phenyl)imine is obtained.

The imine obtained is dissolved in 20 cm$^3$ of methanol at a temperature in the region of 20° C. 0.014 g of sodium borohydride is added. The reaction medium is stirred at room temperature for 24 hours. The reaction medium is concentrated under reduced pressure. The residue obtained is taken up in 5 cm$^3$ of water and 20 cm$^3$ of ethyl acetate. After separation of the phases by settling, the organic phase is dried over magnesium sulfate, filtered and then concentrated under reduced pressure. 0.05 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(4-morpholin-4-ylphenyl) amine is obtained with the following characteristics:

Mass spectrum: ES m/z=653 MH$^+$; m/z=327 (M+2H)$^{2+}$/2; m/z=249.8 (M-C$_7$H$_7$SO$_2$+2H)$^{2+}$/2 base peak Stage 35(b): [2-(5,6-Dimethoxy-1-methyl-1H-pyrrolo[3,2-b]pyridin-3-yl)-1H-pyrrolo[2,3-b]pyridin-4-ylmethyl]-(4-morpholin-4-yl-phenyl)amine a) The product is prepared by following the procedure described in example 34, stage (k), starting with 0.05 g of the [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(4-morpholin-4-ylphenyl)amine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34, stage (k) and 0.4 cm$^3$ of 5N potassium hydroxide. 0.04 g of [2-(5,6-dimethoxy-1-methyl-1H-pyrrolo[3,2-b]pyridin-3-yl)-1H-pyrrolo[2,3-b]pyridin-4-ylmethyl]-(4-morpholin-4-ylphenyl)amine is obtained with the following characteristics:

$^1$H NMR spectrum (300 MHz, (CD$_3$)$_2$SO d6, δ in ppm): 2.86 (m, 4H); 3.67 (m, 4H); 3.85 (s, 3H); 3.87 (s, 3H); 4.01 (s, 3H); 4.51 (broad d, J=6.0 Hz, 2H); 5.92 (broad t, 1H); 6.53 (broad d, J=9.0 Hz, 2H); 6.70 (broad d, J=9.0 Hz, 2H); 6.97 (d, J=5.5 Hz, 1H); 7.34 (d, J=2.0 Hz, 1H); 7.57 (s, 1H); 7.89 (s, 1H); 8.01 (d, J=5.5 Hz, 1H); 11.65 (broad m, 1H).

Mass spectrum: ES m/z=499 MH$^+$; m/z=250 (M+2H)$^{2+}$/2 base peak

EXAMPLE 36

2-(5,6-Dimethoxy-1H-pyrrolo[3,2-b]pyridin-3-yl)-4-(1,3-dioxolan)-2-yl-1H-pyrrolo[2,3-b]pyridine To a solution of 0.125 g of 2-(5,6-dimethoxy-1H-pyrrolo[3,2-b]pyridin-3-yl)-4-(1,3-dioxolan)-2-yl-1-(toluene-4-sulfonyl)-1H-pyrrolo[2,3-b]pyridine in 5 cm$^3$ of THF, at a temperature in the region of 20° C., are added 1.2 cm$^3$ of TBAF. The reaction medium is refluxed for 24 hours. After cooling, the reaction medium is concentrated under reduced pressure. The residue obtained is taken up in 2 cm$^3$ of water and 4 cm$^3$ of dichloromethane. After separation of the phases by settling, the organic phase is dried over magnesium sulfate, filtered and then concentrated under reduced pressure. The residue obtained is purified by flash-pack chromatography (SiO$_2$, dichloromethane/methanol 98/02 by volume as eluents) to give 0.028 g of 2-(5,6-dimethoxy-1H-pyrrolo[3,2-b]pyridin-3-yl)-4-(1,3-dioxolan)-2-yl-1H-pyrrolo[2,3-b]pyridine with the following characteristics:

$^1$H NMR spectrum (300 MHz, (CD$_3$)$_2$SO d6, δ in ppm): 3.83 (s, 3H); from 4.01 to 4.19 (m, 4H); 4.05 (s, 3H); 6.07 (s, 1H); 7.03 (d, J=5.5 Hz, 1H); 7.37 (d, J=2.0 Hz, 1H); 7.39 (s, 1H); 7.98 (d, J=3.0 Hz, 1H); 8.09 (d, J=5.5 Hz, 1H); 11.25 (broad m, 1H); 11.75 (broad m, 1H)

Mass spectrum: ES m/z=367 MH$^+$; base peak

EXAMPLE 37

2-(5,6-Dimethoxy-1-methyl-1H-pyrrolo[3,2-b]pyridin-3-yl)-4-(1,3-dioxolan)-2-yl-1H-pyrrolo[2,3-b] pyridine The product is prepared by following the procedure described in example 34, stage (k), starting with 0.05 g of 2-(5,6-dimethoxy-1-methyl-1H-pyrrolo[3,2-b]pyridin-3-yl)-1-(toluene-4-sulfonyl)-4-(1,3-dioxolan)-2-yl-1H-pyrrolo[2,3-b]pyridine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl] amine used in example 34, stage (k) and 0.37 cm$^3$ of 5N potassium hydroxide. 0.030 g of 2-(5,6-dimethoxy-1-methyl-1H-pyrrolo[3,2-b]pyridin-3-yl)-4-(1,3-dioxolan)-2-yl-1H-pyrrolo[2,3-b]pyridine is obtained with the following characteristics:

$^1$H NMR spectrum (300 MHz, (CD$_3$)$_2$SO d6, δ in ppm): 3.84 (s, 3H); 3.88 (s, 3H); 4.06 (s, 3H); from 4.03 to 4.16 (m, 4H); 6.07 (s, 1H); 7.04 (broad d, J=5.5 Hz, 1H); 7.33 (d, J=2.0 Hz, 1H); 7.59 (s, 1H); 7.92 (s, 1H); 8.10 (d, J=5.5 Hz, 1H); 11.75 (broad m, 1H).

Mass spectrum: IE m/z=380: M$^+$. base peak; m/z=337 (M-C$_2$H$_3$O)$^+$

EXAMPLE 38

2-(5,6-Dimethoxy-1-methyl-1H-pyrrolo[3,2-b]pyridin-3-yl)-1H-pyrrolo[2,3-b]pyridin-4-carbaldehyde The product is prepared by following the procedure described in example 34, stage (k), starting with 0.1 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34, stage (k) and 0.82 cm$^3$ of 5N potassium hydroxide. 0.1 g of 2-(5,6-dimethoxy-1-methyl-1H-pyrrolo [3,2-b]pyridin-3-yl)-1H-pyrrolo[2,3-b]pyridin-4-carbaldehyde is obtained with the following characteristics:

$^1$H NMR spectrum (300 MHz, (CD$_3$)$_2$SO d6, δ in ppm): 3.88 (s, 3H); 3.90 (s, 3H); 4.10 (s, 3H); 7.52 (d, J=5.5 Hz, 1H); 7.61 (s, 1H); 7.84 (d, J=2.0 Hz, 1H); 8.03 (s, 1H); 8.32 (d, J=5.5 Hz, 1H); 10.35 (s, 1H); 12.15 (broad m, 1H).

Mass spectrum: IE m/z=336 M$^+$; base peak

EXAMPLE 39

[2-(5,6-Dimethoxy-1-methyl-1H-pyrrolo[3,2-b]pyridin-3-yl)-1H-pyrrolo[2,3-b]pyridin-4-yl]-methanol To a solution of 0.07 g of 2-(5,6-dimethoxy-1-methyl-1H-pyrrolo[3,2-b]pyridin-3-yl)-1H-pyrrolo[2,3-b]pyridin-4-carbaldehyde in 7 cm$^3$ of methanol and 20 cm$^3$ of dichloromethane, at a temperature in the region of 20° C., is added 0.012 g of sodium borohydride. The reaction medium is stirred at room temperature for 24 hours. The reaction medium is concentrated under reduced pressure. The residue obtained is taken up in 10 cm³ of water and 20 cm³ of ethyl acetate. After separation of the phases by settling, the organic phase is dried over magnesium sulfate, filtered and then concentrated under reduced pressure. 0.045 g of [2-(5,6-dimethoxy-1-methyl-1H-pyrrolo[3,2-b]pyridin-3-yl)-1H-pyrrolo[2,3-b]pyridin-4-yl]methanol is obtained with the following characteristics:

¹H NMR spectrum (300 MHz, (CD₃)₂SO d6, δ in ppm): 3.84 (s, 3H); 3.88 (s, 3H); 4.05 (s, 3H); 4.82 (broad d, J=6.0 Hz, 2H); 5.32 (broad t, J=6.0 Hz, 1H); 7.04 (d, J=5.5 Hz, 1H); 7.21 (d, J=2.0 Hz, 1H); 7.58 (s, 1H); 7.89 (s, 1H); 8.07 (d, J=5.5 Hz, 1H); 11.6 (broad m, 1H).

Mass spectrum: ES m/z=339 MH⁺ base peak

EXAMPLE 40

[²-(5,6-Dimethoxy-1-methyl-1H-pyrrolo[3,2-b]pyridin-3-yl)-1H-pyrrolo[2,3-b]pyridin-4-yl]-methylamine Stage 40(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-carbaldehyde oxime To a solution of 1 g of [²-(5,6-dimethoxy-1-methyl-1H-pyrrolo[3,2-b]pyridin-3-yl)-1-(toluene-4-sulfonyl)-1H-pyrrolo[2,3-b]pyridine-4-carbaldehyde in 50 cm³ of pyridine, at a temperature in the region of 20° C., is added 0.46 g of hydroxylamine hydrochloride. The reaction medium is heated at 50° C. for 24 hours. The reaction medium is concentrated under reduced pressure. The residue obtained is taken up in 20 cm³ of water and 50 cm³ of dichloromethane. After separation of the phases by settling, the organic phase is dried over magnesium sulfate, filtered and then concentrated under reduced pressure. 0.510 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde oxime is obtained with the following characteristics:

Mass spectrum: ES m/z=506 MH⁺; base peak

Stage 40(b): [2-(5,6-Dimethoxy-1-methyl-1H-pyrrolo[3,2-b]pyridin-3-yl)-1H-pyrrolo[2,3-b]pyridin-4-yl]-methylamine To a solution of 0.56 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde oxime in 30 cm³ of ethanol and 25 cm³ of water, at a temperature in the region of 20° C., is added 0.216 g of zinc and 12 cm³ of concentrated formic acid. A further 0.216 g of zinc is added and the mixture is stirred for a further 24 hours. The reaction medium is stirred at this same temperature for 24 hours. The reaction medium is filtered through Celite and the filtrate is concentrated under reduced pressure. The residue obtained is purified by flash-pack chromatography (SiO₂, dichloromethane/methanol 95/05, then dichloromethane/methanol/triethylamine 100/10/1, then dichloromethane/methanol/28% aqueous ammonia 100/10/2 by volume as eluents, Ar). The residue obtained is again purified by flash-pack chromatography (SiO₂, dichloromethane/methanol/28% aqueous ammonia 460/40/1.5 by volume as eluents, Ar). 0.03 g of [2-(5,6-dimethoxy1-methyl-1H-indol-3-yl)-1-(toluene-4-sulfonyl)-1H-pyrrolo[2,3-b]pyridin-4-yl]methylamine is obtained with the following characteristics:

¹H NMR spectrum (300 MHz, (CD₃)₂SO d6, δ in ppm): 3.83 (s, 3H); 3.88 (s, 3H); 4.02 (broad s, 2H); 4.05 (s, 3H); 7.08 (d, J=5.5 Hz, 1H); 7.21 (broad s, 1H); 7.58 (s, 1H); 7.88 (s, 1H); 8.06 (d, J=5.5 Hz, 1H); 11.6 (broad m, 1H).

Mass spectrum: IE m/z=337 M⁺. base peak

EXAMPLE 41

[2-(5,6-Dimethoxy-1-methyl-1H-pyrrolo[3,2-b]pyridin-3-yl)-1H-pyrrolo[2,3-b]pyridin-4-carbaldehyde oxime The product is prepared by following the procedure described in example 34, stage (k), starting with 0.1 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde oxime instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34, stage (k) and 1 cm³ of 5N potassium hydroxide. After purification by preparative LC/MS (acetonitrile/water/trifluoroacetic acid as eluents), 0.040 g of [2-(5,6-dimethoxy-1-methyl-1H-pyrrolo[3,2-b]pyridin-3-yl)-1H-pyrrolo[2,3-b]pyridin-4-carbaldehyde oxime is obtained with the following characteristics:

¹H NMR spectrum (300 MHz, (CD₃)₂SO d6, δ in ppm): 3.86 (s, 3H); 3.88 (s, 3H); 4.08 (s, 3H); 7.15 (d, J=5.5 Hz, 1H); 7.55 (d, J=2.0 Hz, 1H); 7.59 (s, 1H); 7.92 (s, 1H); 8.12 (d, J=5.5 Hz, 1H); 8.41 (s, 1H); 11.55 (broad s, 1H); 11.85 (broad m, 1H).

Mass spectrum: ES m/z=352 MH⁺ base peak; m/z=257.2 (M+2H)²⁺/2

EXAMPLE 42

[2-(5,6-Dimethoxy-1-methyl-1H-pyrrolo[3,2-b]pyridin-3-yl)-1H-pyrrolo[2,3-b]pyridin-4-ylmethyl]-(4-morpholin-4-ylbenzyl)amine Stage 42(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-ylmethyl]-(4-morpholin-4-ylbenzyl)amine The product is prepared by following the procedure described in example 34, stage (j) starting with 0.1 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.196 cm³ of 4-morpholinobenzylamine instead of the cyclopropylamine used in example 34, stage (j). After purification by flash-pack chromatography (SiO₂, dichloromethane/methanol 98/2 by volume as eluents), 0.031 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(4-morpholin-4-yl-benzyl)amine is obtained with the following characteristics:

Mass spectrum: ES: m/z=667; MH⁺; base peak

Stage 42(b): [2-(5,6-Dimethoxy-1-methyl-1H-pyrrolo[3,2-b]pyridin-3-yl)-1H-pyrrolo[2,3-b]pyridin-4-ylmethyl]-(4-morpholin-4-ylbenzyl)amine The product is prepared by following the procedure described in example 34, stage (k), starting with 0.03 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(4-morpholin-4-yl-benzyl)amine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34, stage (k) and 0.18 cm³ of 5N potassium hydroxide. 0.013 g of [2-(5,6-dimethoxy-1-methyl-1H-pyrrolo[3,2-b]pyridin-3-yl)-1H-pyrrolo[2,3-b]pyridin-4-ylmethyl]-(4-morpholin-4-yl-benzyl)amine is obtained with the following characteristics:

$^1$H NMR spectrum (300 MHz, $(CD_3)_2SO$ d6, δ in ppm): 3.06 (m, 4H); 3.68 (broad s, 2H); 3.72 (m, 4H); 3.83 (s, 3H); 3.88 (s, 3H); 3.98 (broad s, 2H); 4.01 (s, 3H); 6.89 (d, J=8.5 Hz, 2H); 7.06 (d, J=5.5 Hz, 1H); 7.22 (d, J=8.5 Hz, 2H); 7.24 (s, 1H); 7.58 (s, 1H); 7.89 (s, 1H); 8.05 (d, J=5.5 Hz, 1H); 11.6 (s, 1H)

Mass spectrum: ES m/z=513 MH⁺; base peak

EXAMPLE 43

[2-(5,6-Dimethoxy-1-methyl-1H-pyrrolo[3,2-b]pyridin-3-yl)-1H-pyrrolo[2,3-b]pyridin-4-ylmethyl]-[4-(4-methylpiperazin-1-yl)benzyl]amine Stage 43(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-ylmethyl]-[4-(4-methylpiperazin-1-yl)-benzyl]amine The product is prepared by following the procedure described in example 34, stage (j), starting with 0.1 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.209 cm³ of 4-(4-methylpiperazino)benzylamine instead of the cyclopropylamine used in example 34, stage (j). After purification by flash-pack chromatography (SiO₂, dichloromethane/methanol 90/10 by volume as eluents), 0.083 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-[4-(4-methylpiperazin-1-yl)-benzyl]amine is obtained with the following characteristics:

Mass spectrum: ES m/z=680 MH⁺; m/z=340.7 (M+2H)²⁺/2 base peak; m/z=263.2 (M-$C_7H_7SO_2$+2H)²⁺/2

Stage 43(b): [2-(5,6-Dimethoxy-1-methyl-1H-pyrrolo[3,2-b]pyridin-3-yl)-1H-pyrrolo[2,3-b]pyridin-4-ylmethyl]-[4-(4-methylpiperazin-1-yl)benzyl]amine The product is prepared by following the procedure described in example 34, stage (k), starting with 0.08 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-[4-(4-methyl-piperazin-1-yl)benzyl]amine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 0.471 cm³ of 5N potassium hydroxide. 0.008 g of [2-(5,6-dimethoxy-1-methyl-1H-pyrrolo[3,2-b]pyridin-3-yl)-1H-pyrrolo[2,3-b]pyridin-4-ylmethyl]-[4-(4-methyl-piperazin-1-yl)-benzyl]amine is obtained with the following characteristics:

$^1$H NMR spectrum (300 MHz, $(CD_3)_2SO$ d6, δ in ppm): 2.20 (s, 3H); 2.43 (broad m, 4H); 3.08 (broad m, 4H); 3.67 (s, 2H); 3.83 (s, 3H); 3.88 (s, 3H); 3.97 (s, 2H); 4.01 (s, 3H); 6.88 (broad d, J=8.5 Hz, 2H); 7.07 (broad d, J=5.0 Hz, 1H); 7.21 (broad d, J=8.5 Hz, 2H); 7.25 (s, 1H); 7.58 (s, 1H); 7.89 (s, 1H); 8.04 (broad d, J=5.0 Hz, 1H); 11.6 (s, 1H).

Mass spectrum: ES m/z=526 MH⁺; m/z=263.7 (M+2H)²⁺/2 base peak

EXAMPLE 44

[2-(5,6-Dimethoxy-1-methyl-1H-pyrrolo[3,2-b]pyridin-3-yl)-1H-pyrrolo[2,3-b]pyridin-4-ylmethyl]-(3-piperidin-1-ylpropyl)amine Stage 44(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-ylmethyl]-(3-piperidin-1-ylpropyl) amine The product is prepared by following the procedure described in example 34 stage (j), starting with 0.1 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.145 g of 3-piperidino-propylamine instead of the cyclopropylamine used in example 34 stage (j). After purification by flash-pack chromatography (SiO₂, dichloromethane/methanol/aqueous ammonia (28%) 40/5/0.5 by volume as eluents), 0.05 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(3-piperidin-1-ylpropyl) amine is obtained with the following characteristics:

Mass spectrum: ES m/z=617 MH⁺; m/z=309.3 (M+2H)²⁺/2 base peak; m/z=231.7 (M-$C_7H_7SO_2$+2H)²⁺/2

Stage 44(b): [2-(5,6-Dimethoxy-1-methyl-1H-pyrrolo[3,2-b]pyridin-3-yl)-1H-pyrrolo[2,3-b]pyridin-4-ylmethyl]-(3-piperidin-1-ylpropyl)amine The product is prepared by following the procedure described in example 34 stage (k), starting with 0.050 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(3-piperidin-1-yl-propyl)amine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 0.324 cm³ of 5N potassium hydroxide. 0.012 g of [2-(5,6-dimethoxy-1-methyl-1H-pyrrolo[3,2-b]pyridin-3-yl)-1H-pyrrolo[2,3-b]pyridin-4-ylmethyl]-(3-piperidin-1-yl-propyl) amine is obtained with the following characteristics:

$^1$H NMR spectrum (300 MHz, $(CD_3)_2SO$ d6, δ in ppm): 1.32 (m, 2H); 1.42 (m, 4H); 1.60 (m, 2H); 2.27 (m, 6H); 2.59 (t, J=7.0 Hz, 2H); 3.83 (s, 3H); 3.89 (s, 3H); 3.98 (broad s, 2H); 4.06 (s, 3H); 7.01 (d, J=5.0 Hz, 1H); 7.28 (d, J=2.0 Hz, 1H); 7.58 (s, 1H); 7.88 (s, 1H); 8.03 (d, J=5.0 Hz, 1H); 11.6 (broad m, 1H).

Mass spectrum: EI m/z=462: M⁺·; m/z=322 (M-$C_8H_{16}N_2$)⁺· base peak; m/z=98 $C_6H_{12}N^+$

EXAMPLE 45

[2-(5,6-Dimethoxy-1-methyl-1H-pyrrolo[3,2-b]pyridin-3-yl)-1H-pyrrolo[2,3-b]pyridin-4-ylmethyl]-(3-(4-methylpiperazin-1-yl)propyl)amine Stage 45(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-ylmethyl]-(3-(4-methylpiperazin-1-yl-propyl)amine The product is prepared by following the procedure described in example 34 stage (j), starting with 0.1 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.160 g of 1-(3-aminopropyl)-4-methylpiperazine instead of the cyclopropylamine used in example 34 stage (j). After purification by flash-pack chromatography (SiO$_2$, dichloromethane/methanol/aqueous ammonia (28%) 40/05/0.5 by volume as eluents), 0.028 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(3-(4-methylpiperazin-1-ylpropyl)amine is obtained with the following characteristics:

Mass spectrum: IC m/z=632 MH$^+$; base peak

Stage 45(b): [2-(5,6-Dimethoxy-1-methyl-1H-pyrrolo[3,2-b]pyridin-3-yl)-1H-pyrrolo[2,3-b]pyridin-4-ylmethyl]-(3-(4-methylpiperazin-1-yl)propyl)amine The product is prepared by following the procedure described in example 34 stage (k), starting with 0.025 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(3-(4-methyl-piperazin-1-ylpropyl)amine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 0.158 cm$^3$ of 5N potassium hydroxide. After purification by preparative LC/MS (acetonitrile/water/trifluoroacetic acid as eluents), 0.002 g of [2-(5,6-dimethoxy-1-methyl-1H-pyrrolo[3,2-b]pyridin-3-yl)-1H-pyrrolo[2,3-b]pyridin-4-ylmethyl]-(3-(4-methylpiperazin-1-yl)propyl)amine is obtained with the following characteristics:

$^1$H NMR spectrum (300 MHz, (CD$_3$)$_2$SO d6, δ in ppm): 1.79 (m, 2H); 2.17 (s, 3H); from 2.20 to 2.55 (very broad m, 8H); 2.46 (t, J=7.0 Hz, 2H); 2.83 (t, J=7.0 Hz, 2H); 3.89 (s, 3H); 3.95 (s, 3H); 4.15 (broad s, 2H); 4.20 (s, 3H); 7.03 (s, 1H); 7.11 (d, J=5.0 Hz, 1H); 7.45 (s, 1H); 7.78 (s, 1H); 8.09 (d, J=5.0 Hz, 1H).

Mass spectrum: ES m/z=478 MH$^+$; m/z=239.7 (M+2H)$^{2+}$/2 base peak

EXAMPLE 46

[2-(5,6-Dimethoxy-1-methyl-1H-pyrrolo[3,2-b]pyridin-3-yl)-1H-pyrrolo[2,3-b]pyridin-4-ylmethyl]-(1-methylpiperidin-4-yl)amine Stage 46(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-ylmethyl]-(1-methylpiperidin-4-yl)amine The product is prepared by following the procedure described in example 34 stage (j), starting with 0.3 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.348 g of 4-amino-1-methylpiperidine instead of the cyclopropylamine used in example 34 stage (j). After purification by flash-pack chromatography (SiO$_2$, dichloromethane/methanol 98/02 by volume as eluents), 0.28 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(1-methylpiperidin-4-yl)amine is obtained with the following characteristics:

Mass spectrum: ES m/z=589 MH$^+$ base peak; m/z=295.7 (M+2H)$^{2+}$/2

Stage 46(b): [2-(5,6-Dimethoxy-1-methyl-1H-pyrrolo[3,2-b]pyridin-3-yl)-1H-pyrrolo[2,3-b]pyridin-4-ylmethyl]-(1-methylpiperidin-4-yl)amine The product is prepared by following the procedure described in example 34 stage (k) starting with 0.250 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-(1-methylpiperidin-4-yl)amine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 2 cm$^3$ of 5N potassium hydroxide. After purification by flash-pack chromatography (SiO$_2$, dichloromethane/methanol 90/10 by volume as eluents), 0.170 g of [2-(5,6-dimethoxy-1-methyl-1H-pyrrolo[3,2-b]pyridin-3-yl)-1H-pyrrolo[2,3-b]pyridin-4-ylmethyl]-(1-methylpiperidin-4-yl)amine is obtained with the following characteristics:

$^1$H NMR spectrum (300 MHz, (CD$_3$)$_2$SO d6, δ in ppm) 1.33 (m, 2H); 1.84 (m, 4H); 1.99 (broad m, 1H); 2.10 (s, 3H); 2.42 (broad m, 1H); 2.68 (m, 2H); 3.84 (s, 3H); 3.88 (s, 3H); 4.00 (broad d, J=5.5 Hz, 2H); 4.05 (s, 3H); 7.02 (d, J=5.5 Hz, 1H); 7.29 (s, 1H); 7.58 (s, 1H); 7.90 (s, 1H); 8.03 (d, J=5.5 Hz, 1H); 11.6 (broad s, 1H).

Mass spectrum: IE m/z=434 M$^+$; m/z=336 (M-C$_6$H$_{12}$N)$^+$; m/z=322 (M-C$_6$H$_{12}$N$_2$)$^+$ base peak

EXAMPLE 47

[2-(5,6-Dimethoxy-1-methyl-1H-pyrrolo[3,2-b]pyridin-3-yl)-1H-pyrrolo[2,3-b]pyridin-4-ylmethyl]-[2-(3-methyl-3H-imidazol-4-yl)ethyl]amine Stage 47(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-ylmethyl]-[2-(3-methyl-3H-imidazol-4-yl)-ethyl]amine The product is prepared by following the procedure described in example 34 stage (j) starting with 0.06 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.05 g of 3-methylhistamine dihydrochloride instead of the cyclopropylamine used in example 34 stage (j). After purification by flash-pack chromatography (SiO$_2$, dichloromethane/methanol 98/02 by volume as eluents), 0.070 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-[2-(3-methyl-3H-imidazol-4-yl)-ethyl]amine is obtained with the following characteristics:

Mass spectrum: ES m/z=600 MH$^+$; m/z=300.4 (M+2H)$^{2+}$/2; m/z=223 (M-C$_7$H$_7$SO$_2$+2H)$^{2+}$/2 base peak Stage 47(b): [2-(5,6-Dimethoxy-1-methyl-1H-pyrrolo[3,2-b]pyridin-3-yl)-1H-pyrrolo[2,3-b]pyridin-4-ylmethyl]-[2-(3-methyl-3H-imidazol-4-yl)ethyl]amine The product is prepared by following the procedure described in example 34 stage (k), starting with 0.070 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-[2-(3-methyl-3H-imidazol-4-yl)ethyl]amine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 0.5 cm$^3$ of 5N potassium hydroxide. 0.048 g of [2-(5,6- dimethoxy-1-methyl-1H-pyrrolo[3,2-b]pyridin-3-yl)-1H-pyrrolo[2,3-b]pyridin-4-ylmethyl]-[2-(3-methyl-3H-imidazol-4-yl)ethyl]amine is obtained with the following characteristics:

1H NMR spectrum (300 MHz, (CD$_3$)$_2$SO d6, δ in ppm) 2.25 (broad m, 1H); 2.71 (m, 2H); 2.81 (m, 2H); 3.51 (s, 3H); 3.83 (s, 3H); 3.88 (s, 3H); 4.03 (broad s, 5H); 6.62 (s, 1H); 7.00 (d, J=5.5 Hz, 1H); 7.29 (broad s, 1H); 7.43 (s, 1H); 7.58 (s, 1H); 7.88 (s, 1H); 8.03 (d, J=5.5 Hz, 1H); 11.6 (broad m, 1H).

Mass spectrum: ES m/z=446 MH$^+$; m/z=223.9 (M+2H)$^{2+}$/2 base peak

EXAMPLE 48

2-([2-(5,6-Dimethoxy-1-methyl-1H-pyrrolo[3,2-b]pyridin-3-yl)-1H-pyrrolo[2,3-b]pyridin-4-ylmethyl]amino)-2-methylpropionic acid trifluoroacetate Stage 48(a): Methyl 2-{[2-(5,6-dimethoxy-1-methyl-1H-pyrrolo[3,2-b]pyridin-3-yl)-1-(toluene-4-sufonyl)-1H-pyrrolo[2,3-b]pyridin-4-ylmethyl]amino}-2-methylpropionate The product is prepared by following the procedure described in example 34 stage (j), starting with 0.3 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.468 g of methyl 2,2-dimethylglycinate hydrochloride instead of the cyclopropylamine used in example 34 stage (j). 0.3 g of 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl](2-methylpropionic acid methyl ester)imine is obtained. The imine is dissolved in 30 cm$^3$ of ethanol at a temperature in the region of 20° C. 0.1 g of sodium borohydride is added. The reaction medium is stirred at room temperature for 24 hours. The reaction medium is concentrated under reduced pressure. The residue obtained is taken up in a mixture of dichloromethane/methanol 98/02 by volume and then filtered. The filtrate is concentrated under reduced pressure. The residue obtained is purified by flash-pack chromatography (SiO$_2$, dichloromethane/methanol 98/02 by volume as eluents) to give 0.250 g of methyl 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}-2-methylpropionate with the following characteristics:

Mass spectrum: IC m/z=606 M$_1$H$^+$; m/z=592 MH$^+$; m/z=491 M$_2$H$^+$ base peak Stage 48(b): 2-{[2-(5,6-Dimethoxy-1-methyl-1H-pyrrolo[3,2-b]pyridin-3-yl)-1H-pyrrolo[2,3-b]pyridin-4-ylmethyl]amino}-2-methylpropionic acid trifluoroacetate:

The product is prepared by following the procedure described in example 34 stage (k), starting with 0.250 g of methyl 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}-2-methyl-propionate instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 2 cm$^3$ of 5N potassium hydroxide. After purification by preparative LC/MS (acetonitrile/water/trifluoroacetic acid as eluents), 0.050 g of 2-{[2-(5,6-dimethoxy-1-methyl-1H-pyrrolo[3,2-b]pyridin-3-yl)-1H-pyrrolo[2,3-b]pyridin-4-ylmethyl] amino}-2-methylpropionic acid trifluoroacetate is obtained with the following characteristics:

$^1$H NMR spectrum (300 MHz, (CD$_3$)$_2$SO d6, δ in ppm): 1.64 (s, 6H); 3.86 (s, 3H); 3.88 (s, 3H); 4.09 (s, 3H); 4.42 (broad m, 2H); 7.17 (d, J=5.5 Hz, 1H); 7.48 (d, J=2.0 Hz, 1H); 7.60 (s, 1H); 7.92 (s, 1H); 8.19 (d, J=5.5 Hz, 1H); 9.37 (broad m, 2H); 11.95 (broad s, 1H).

Mass spectrum: IC m/z=424 MH$^+$; base peak

EXAMPLE 49

4-{[2-(5,6-Dimethoxy-1-methyl-1H-pyrrolo[3,2-b]pyridin-3-yl)-1H-pyrrolo[2,3-b]pyridin-4-ylmethyl]amino}phenol To a solution of 0.085 g of 4-{[1-[2-(5,6-dimethoxy-1-methyl-1H-pyrrolo[3,2-b]pyridin-3-yl)-1H-pyrrolo[2,3-b]pyridin-4-yl]meth-(E)-ylidene]amino}phenol in 20 cm$^3$ of methanol, at a temperature in the region of 20° C., are added 0.013 g of zinc chloride and 0.013 g of sodium cyanoborohydride. The reaction medium is stirred at the same temperature for 4 hours. The reaction medium is concentrated under reduced pressure. The residue obtained is taken up in 10 cm$^3$ of water and 25 cm$^3$ of dichloromethane, and then basified with 0.1N sodium hydroxide. After separation of the phases by settling, the organic phase is dried over magnesium sulfate, filtered and then concentrated under reduced pressure to give 0.04 g of 4-{[2-(5,6-dimethoxy-1-methyl-1H-pyrrolo[3,2-b]pyridin-3-yl)-1H-pyrrolo[2,3-b]pyridin-4-ylmethyl]amino}phenol with the following characteristics:

$^1$H NMR spectrum (300 MHz, (CD$_3$)$_2$SO d6, δ in ppm): 3.85 (s, 3H); 3.88 (s, 3H); 4.02 (s, 3H); 4.48 (broad d, J=6.0 Hz, 2H); 5.71 (broad t, J=6.0 Hz, 1H); 6.43 (broad d, J=9.0 Hz, 2H); 6.49 (broad d, J=9.0 Hz, 2H); 6.98 (d, J=5.5 Hz, 1H); 7.32 (d, J=2.0 Hz, 1H); 7.59 (s, 1H); 7.89 (s, 1H); 8.01 (d, J=5.5 Hz, 1H); 8.37 (s, 1H); 11.7 (broad m, 1H).

Mass spectrum: ES m/z=430 MH$^+$; base peak

EXAMPLE 50

4-{[1-[2-(5,6-Dimethoxy-1-methyl-1H-pyrrolo[3,2-b]pyridin-3-yl)-1H-pyrrolo[2,3-b]pyridin-4-yl]meth-(E)-ylidene]amino}phenol Stage 50(a): 4-{[2-(5,6-Dimethoxy-1-methyl-1H-pyrrolo[3,2-b]pyridin-3-yl)-1-(toluene-4-sulfonyl)-1H-pyrrolo[2,3-b]pyridin-4-yl]meth-(E)-ylidene]amino}phenol The product is prepared by following the procedure described in example 34 stage (j), starting with 0.3 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde and 0.334 g of 4-aminophenol instead of the cyclopropylamine used in example 34 stage (j). After purification by flash-pack chromatography (SiO$_2$, dichloromethane/methanol 98/02 by volume as eluents), 0.340 g of 4-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-yl]meth-(E)-ylidene]amino}phenol is obtained with the following characteristics:

Mass spectrum: IC m/z=582 MH$^+$; base peak

Stage 50(b): 4-{[1-[2-(5,6-Dimethoxy-1-methyl-1H-pyrrolo[3,2-b]pyridin-3-yl)-1H-pyrrolo[2,3-b]pyridin-4-yl]meth-(E)-ylidene]amino}phenol The product is prepared by following the procedure described in example 34 stage (k), starting with 0.340 g of 4-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-yl]meth-(E)-ylidene]amino}phenol instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 2.5 cm³ of 5N potassium hydroxide. 0.100 g of 4-{[1-[2-(5,6-dimethoxy-1-methyl-1H-pyrrolo[3,2-b]pyridin-3-yl)-1H-pyrrolo[2,3-b]pyridin-4-yl]meth-(E)-ylidene]amino}phenol is obtained with the following characteristics:

$^1$H NMR spectrum (300 MHz, $(CD_3)_2SO$ d6, δ in ppm): 3.86 (s, 3H); 3.89 (s, 3H); 4.11 (s, 3H); 6.86 (broad d, J=8.5 Hz, 2H); 7.30 (broad d, J=8.5 Hz, 2H); 7.38 (d, J=5.5 Hz, 1H); 7.60 (s, 1H); 7.98 (s, 1H); 8.08 (broad s, 1H); 8.21 (d, J=5.5 Hz, 1H); 8.89 (s, 1H); 9.60 (very broad m, 1H); 11.9 (broad s, 1H).

Mass spectrum: IE m/z=427 M$^{+\cdot}$; m/z=109 $C_6H_7NO^+$. base peak

EXAMPLE 51

N-1-[2-(5,6-Dimethoxy-1-methyl-1H-pyrrolo[3,2-b]pyridin-3-yl)-1H-pyrrolo[2,3-b]pyridin-4-ylmethyl]ethane-1,2-diamine hydrochloride To a solution of 0.095 g of tert-butyl (2-{[2-(5,6-dimethoxy-1-methyl-1H-pyrrolo[3,2-b]pyridin-3-yl)-1H-pyrrolo[2,3-b]pyridin-4-ylmethyl]amino}ethyl)carbamate in 6 cm³ of methanol and 2 cm³ of dichloromethane, at a temperature in the region of 20° C., are added 2 cm³ of hydrochloric acid (4N in dioxane). The reaction medium is stirred at room temperature for 24 hours. The reaction medium is concentrated under reduced pressure. The residue obtained is taken up in 5 cm³ of ethyl ether. The solid obtained is filtered off on a sinter funnel and then dried under vacuum to give 0.126 g of N-1-[2-(5,6-dimethoxy-1-methyl-1H-pyrrolo[3,2-b]pyridin-3-yl)-1H-pyrrolo[2,3-b]pyridin-4-ylmethyl]ethane-1,2-diamine hydrochloride with the following characteristics:

$^1$H NMR spectrum (300 MHz, $(CD_3)_2SO$ d6, δ in ppm): from 3.20 to 3.55 (partially masked m, 4H); 3.87 (s, 3H); 3.89 (s, 3H); 4.10 (s, 3H); 4.53 (m, 2H); 7.32 (broad d, J=5.5 Hz, 1H); 7.38 (broad s, 1H); 7.60 (s, 1H); 7.93 (s, 1H); 8.19 (broad d, J=5.5 Hz, 1H); 8.22 (broad m, 3H); 9.77 (broad m, 2H); 12.0 (broad s, 1H).

Mass spectrum: ES m/z=381 MH$^+$; m/z=321 (M-$C_2H_8N_2$+H)$^+$ base peak; m/z=59 $C_2H_7N_2^+$

EXAMPLE 52 tert-Butyl (2-{[2-(5,6-dimethoxy-1-methyl-1H-pyrrolo[3,2-b]pyridin-3-yl)-1H-pyrrolo[2,3-b]pyridin-4-ylmethyl]amino}ethyl)carbamate Stage 52(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-yl]methanol To a solution of 4.9 g of 2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde in 100 cm³ of methanol, at a temperature in the region of 20° C., is added 0.57 g of sodium borohydride. The reaction medium is stirred at room temperature for 3 hours. The reaction medium is concentrated under reduced pressure. The residue obtained is taken up in 100 cm³ of water and 100 cm³ of ethyl acetate. After separation of the phases by settling, the organic phase is dried over magnesium sulfate, filtered and then concentrated under reduced pressure. 4.92 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-yl]methanol are obtained with the following characteristics:

Mass spectrum: ES m/z=493 MH$^+$; base peak

Stage 52(b): 3-[4-Chloromethyl-1-(toluene-4-sulfonyl)-1H-pyrrolo[2,3-b]pyridin-2-yl]-5,6-dimethoxy-1-methyl-1H-pyrrolo[3,2-b]pyridine To a solution of 4.2 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-yl]methanol in 50 cm³ of dichloromethane, at a temperature in the region of 20° C., are added 0.747 cm³ of thionyl chloride and 0.3 cm³ of DMF. The reaction medium is stirred at this same temperature for 2 hours. Ice is added and the reaction medium is then neutralized with saturated sodium hydrogencarbonate solution. After separation of the phases by settling, the organic phase is dried over magnesium sulfate, filtered and then concentrated under reduced pressure. After purification by flash-pack chromatography (SiO$_2$, dichloromethane/ethyl acetate 95/05 by volume as eluents), 2.64 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine are obtained with the following characteristics:

Mass spectrum: IE m/z=510 M$^{+\cdot}$; m/z=355 (M-$C_7H_7SO_2$)$^+$ base peak

Stage 52(c): tert-Butyl (2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}ethyl)carbamate To a solution of 0.3 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine in 15 cm³ of acetonitrile, at a temperature in the region of 20° C., are added 0.232 cm³ of N-Boc-ethylenediamine, 0.406 g of potassium carbonate and 0.088 g of sodium iodide. The reaction medium is heated at 80° C. for 3 hours. After cooling, the reaction medium is filtered through a sinter funnel and the filtrate is concentrated under reduced pressure. The residue obtained is taken up in 5 cm³ of water and 10 cm³ of dichloromethane. After separation of the phases by settling, the organic phase is dried over magnesium sulfate, filtered and then concentrated under reduced pressure. After purification on a Biotage flash cartridge (SiO$_2$, 99.5/0.5 dichloromethane/methanol then 99/01 dichloromethane/methanol then 98.5/1.5 dichloromethane/methanol then 98/02 dichloromethane/methanol by volume as eluents), 0.196 g of tert-butyl 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}ethyl)carbamate is obtained with the following characteristics:

Mass spectrum: IE m/z=634 M$^{+\cdot}$; m/z=560 (M-$C_4H_{10}O$)$^{+\cdot}$; m/z=405 (m/z=560-$C_7H_7SO_2$)$^+$; m/z=321 (m/z=405-$C_3H_4N_2O$)$^+$; m/z=59 $C_2H_7N_2^+$ base peak Stage 52(d): tert-Butyl (2-{[2-(5,6-dimethoxy-1-methyl-1H-pyrrolo[3,2-b]pyridin-3-yl)-1H-pyrrolo[2,3-b]pyridin-4-ylmethyl]amino}ethyl)carbamate The product is prepared by following the procedure described in example 34 stage (k), starting with 0.19 g of tert-butyl (2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}ethyl)carbamate instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 1.2 cm$^3$ of 5N potassium hydroxide. 0.120 g of tert-butyl (2-{[2-(5,6-dimethoxy-1-methyl-1H-pyrrolo[3,2-b]pyridin-3-yl)-1H-pyrrolo[2,3-b]pyridin-4-ylmethyl]amino}ethyl)carbamate is obtained with the following characteristics:

1H NMR spectrum (300 MHz, (CD$_3$)$_2$SO d6, δ in ppm): 1.34 (s, 9H); 2.25 (broad m, 1H); 2.61 (t, J=6.5 Hz, 2H); 3.05 (m, 2H); 3.83 (s, 3H); 3.88 (s, 3H); 3.99 (broad s, 2H); 4.05 (s, 3H); 6.72 (broad t, J=6.0 Hz, 1H); 7.01 (d, J=5.5 Hz, 1H); 7.28 (d, J=2.0 Hz, 1H); 7.58 (s, 1H); 7.89 (s, 1H); 8.03 (d, J=5.5 Hz, 1H); 11.6 (broad m, 1H).

Mass spectrum: IE m/z=480 M$^+$; m/z=321 (M-C$_7$H$_{15}$N$_2$O$_2$)$^+$ base peak

EXAMPLE 53

[2-(5,6-Dimethoxy-1-methyl-1H-pyrrolo[3,2-b]pyridin-3-yl)-1H-pyrrolo[2,3-b]pyridin-4-ylmethyl]-piperidin-4-ylmethylamine hydrochloride The product is prepared by following the procedure described in example 51 starting with 0.115 g of tert-butyl 4-({[2-(5,6-dimethoxy-1-methyl-1H-pyrrolo[3,2-b]pyridin-3-yl)-1H-pyrrolo[2,3-b]pyridin-4-ylmethyl]amino}methyl)piperidine-1-carboxylate instead of the tert-butyl (2-{[2-(5,6-dimethoxy-1-methyl-1H-pyrrolo[3,2-b]pyridin-3-yl)-1H-pyrrolo[2,3-b]pyridin-4-ylmethyl]amino}ethyl)carbamate used in example 51 and 1.3 cm$^3$ of 5N hydrochloric acid in dioxane. 0.101 g of [2-(5,6-dimethoxy-1-methyl-1H-pyrrolo[3,2-b]pyridin-3-yl)-1H-pyrrolo[2,3-b]pyridin-4-ylmethyl]-piperidin-4-ylmethylamine hydrochloride is obtained with the following characteristics:

$^1$H NMR spectrum (300 MHz, (CD$_3$)$_2$SO d6, δ in ppm): 1.40 (m, 2H); 1.95 (m, 2H); 2.10 (broad m, 1H); 2.84 (m, 2H); 2.99 (m, 2H); 3.28 (m, 2H); 3.87 (s, 3H); 3.89 (s, 3H); 4.10 (s, 3H); 4.48 (m, 2H); from 7.32 to 7.39 (m, 2H); 7.61 (s, 1H); 7.96 (s, 1H); 8.19 (d, J=5.5 Hz, 1H); 8.65 (broad m, 1H); 8.83 (broad m, 1H); 9.44 (broad m, 2H); 12.1 (broad m, 1H).

Mass spectrum: IE m/z=434 M$^+$; m/z=322 (M-C$_6$H$_{14}$N$_2$)$^+$; m/z=36 HCl$^+$. base peak

EXAMPLE 54 tert-Butyl 4-({[2-(5,6-dimethoxy-1-methyl-1H-pyrrolo[3,2-b]pyridin-3-yl)-1H-pyrrolo[2,3-b]pyridin-4-ylmethyl]amino}methyl)piperidine-1-carboxylate Stage 54(a): tert-Butyl 4-({[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}methyl)piperidine-1-carboxylate The product is prepared by following the procedure described in example 52c, starting with 0.3 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine and 0.315 g of 4-(aminomethyl)-1-N-Boc-piperidine instead of the N-Boc-ethylenediamine used in example 52c. 0.197 g of tert-butyl 4-({[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}methyl)piperidine-1-carboxylate is obtained with the following characteristics:

Mass spectrum: IC m/z=689 MH$^+$; base peak

Stage 54(b): tert-Butyl 4-({[2-(5,6-dimethoxy-1-methyl-1H-pyrrolo[3,2-b]pyridin-3-yl)-1H-pyrrolo[2,3-b]pyridin-4-ylmethyl]amino}methyl)piperidine-1-carboxylate The product is prepared by following the procedure described in example 34 stage (k), starting with 0.340 g of tert-butyl 4-({[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}methyl)piperidine-1-carboxylate instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 1.13 cm$^3$ of 5N potassium hydroxide. 0.140 g of tert-butyl 4-({[2-(5,6-dimethoxy-1-methyl-1H-pyrrolo[3,2-b]pyridin-3-yl)-1H-pyrrolo[2,3-b]pyridin-4-ylmethyl]amino}methyl)piperidine-1-carboxylate is obtained with the following characteristics:

$^1$H NMR spectrum (300 MHz, (CD$_3$)$_2$SO d6, δ in ppm): 0.98 (m, 2H); 1.37 (s, 9H); 1.60 (m, 1H); 1.72 (m, 2H); 2.11 (m, 1H); 2.45 (partially masked m, 2H); 2.66 (m, 2H); 3.84 (s, 3H); 3.87 (s, 3H); 3.91 (partially masked m, 1H); 3.98 (s, 2H); 4.05 (s, 3H); 7.02 (d, J=5.0 Hz, 1H); 7.25 (s, 1H); 7.58 (s, 1H); 7.88 (s, 1H); 8.04 (d, J=5.0 Hz, 1H); 11.6 (broad s, 1H).

Mass spectrum: IE m/z=534 M$^+$; m/z=322 (M-C$_{11}$H$_{20}$N$_2$O$_2$)$^+$. base peak; m/z=57 C$_4$H$_9^+$

EXAMPLE 55

N-[2-(5,6-Dimethoxy-1-methyl-1H-pyrrolo[3,2-b]pyridin-3-yl)-1H-pyrrolo[2,3-b]pyridin-4-ylmethyl]cyclohexane-1,4-diamine hydrochloride The product is prepared by following the procedure described in example 51, starting with 0.120 g of tert-butyl (4-{[2-(5,6-dimethoxy-1-methyl-1H-pyrrolo[3,2-b]pyridin-3-yl)-1H-pyrrolo[2,3-b]pyridin-4-ylmethyl]amino}cyclohexyl)-carbamate instead of the tert-butyl (2-{[2-(5,6-dimethoxy-1-methyl-1H-pyrrolo[3,2-b]pyridin-3-yl)-1H-pyrrolo[2,3-b]pyridin-4-ylmethyl]amino}ethyl)carbamate used in example 51 and 2 cm$^3$ of 5N hydrochloric acid in dioxane. 0.133 g of N-[2-(5,6-dimethoxy-1-methyl-1H-pyrrolo[3,2-b]pyridin-3-yl)-1H-pyrrolo[2,3-b]pyridin-4-ylmethyl]cyclohexane-1,4-diamine hydrochloride is obtained with the following characteristics:

$^1$H NMR spectrum (300 MHz, (CD$_3$)$_2$SO d6, δ in ppm): 1.40 (m, 2H); 1.59 (m, 2H); 2.05 (m, 2H); 2.31 (m, 2H); 2.99 (m, 1H); 3.12 (m, 1H); 3.87 (s, 3H); 3.89 (s, 3H); 4.10 (s, 3H); 4.47 (m, 2H); 7.36 (d, J=5.0 Hz, 1H); 7.41 (broad s, 1H); 7.61 (s, 1H); 7.98 (s, 1H); 8.09 (broad m, 3H); 8.20 (d, J=5.0 Hz, 1H); 9.48 (broad m, 2H); 12.15 (broad s, 1H).

Mass spectrum: ES m/z=435 MH$^+$; m/z=418 (M+H—NH$_3$)$^+$; m/z=218.3 (M+2H)$^{2+}$/2;

m/z=209.8 (M-NH$_3$+2H)$^{2+}$/2 base peak

EXAMPLE 56 tert-Butyl (4-{[2-(5,6-dimethoxy-1-methyl-1H-pyrrolo[3,2-b]pyridin-3-yl)-1H-pyrrolo[2,3-b]pyridin-4-ylmethyl]amino}cyclohexyl)carbamate Stage 56(a): tert-Butyl (4-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}cyclohexyl)carbamate The product is prepared by following the procedure described in example 52c starting with 0.3 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine and 0.315 g of tert-butyl (4-aminocyclohexyl)carbamate instead of the N-Boc-ethylenediamine used in example 52c. 0.237 g of tert-butyl (4-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-amino}cyclohexyl)carbamate is obtained with the following characteristics:
Mass spectrum: ES m/z=689 MH$^+$; base peak Stage 56(b): tert-Butyl (4-{[2-(5,6-dimethoxy-1-methyl-1H-pyrrolo[3,2-b]pyridin-3-yl)-1H-pyrrolo[2,3-b]pyridin-4-ylmethyl]amino}cyclohexyl)carbamate The product is prepared by following the procedure described in example 34 stage (k), starting with 0.235 g of tert-butyl (4-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]-amino}cyclohexyl)carbamate instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 1.36 cm$^3$ of 5N potassium hydroxide. 0.145 g of tert-butyl (4-{[2-(5,6-dimethoxy-1-methyl-1H-pyrrolo[3,2-b]pyridin-3-yl)-1H-pyrrolo[2,3-b]pyridin-4-ylmethyl]amino}-cyclohexyl)carbamate is obtained with the following characteristics:
$^1$H NMR spectrum (300 MHz, (CD$_3$)$_2$SO d6, δ in ppm): 1.10 (m, 4H); 1.36 (s, 9H); 1.72 (m, 2H); 1.95 (m, 3H); 2.35 (m, 1H); 3.16 (m, 1H); 3.83 (s, 3H); 3.88 (s, 3H); 4.00 (broad s, 2H); 4.06 (s, 3H); 6.62 (broad d, J=8.0 Hz, 1H); 7.00 (d, J=5.0 Hz, 1H); 7.30 (broad s, 1H); 7.58 (s, 1H); 7.89 (s, 1H); 8.02 (d, J=5.0 Hz, 1H); 11.6 (broad s, 1H).
Mass spectrum: IC m/z=535 MH$^+$ base peak

EXAMPLE 57

Azetidin-3-yl-[2-(5,6-dimethoxy-1-methyl-1H-pyrrolo[3,2-b]pyridin-3-yl)-1H-pyrrolo[2,3-b]pyridin-4-ylmethyl]amine hydrochloride The product is prepared by following the procedure described in example 51, starting with 0.075 g of tert-butyl 3-{[2-(5,6-dimethoxy-1-methyl-1H-pyrrolo[3,2-b]pyridin-3-yl)-1H-pyrrolo[2,3-b]pyridin-4-ylmethyl]amino}azetidine-1-carboxylate instead of the tert-butyl (2-{[2-(5,6-dimethoxy-1-methyl-1H-pyrrolo[3,2-b]pyridin-3-yl)-1H-pyrrolo[2,3-b]pyridin-4-ylmethyl]amino}ethyl)carbamate used in example 51 and 1.2 cm$^3$ of 5N hydrochloric acid in dioxane. 0.077 g of azetidin-3-yl-[2-(5,6-dimethoxy-1-methyl-1H-pyrrolo[3,2-b]pyridin-3-yl)-1H-pyrrolo[2,3-b]pyridin-4-ylmethyl]amine hydrochloride is obtained with the following characteristics:

$^1$H NMR spectrum (300 MHz, (CD$_3$)$_2$SO d6, δ in ppm): 3.87 (s, 3H); 3.89 (s, 3H); 4.10 (partially masked broad m, 2H); 4.11 (s, 3H); 4.30 (broad m, 2H); 4.48 (s, 2H); 7.26 (d, J=5.0 Hz, 1H); 7.38 (broad s, 1H); 7.61 (s, 1H); 7.96 (s, 1H); 8.20 (d, J=5.0 Hz, 1H); 9.05 (broad m, 1H); 9.21 (broad m, 1H); 10.35 (very broad m, 2H); 12.1 (broad s, 1H).
Mass spectrum: ES m/z=393 MH$^+$; m/z=321 (M-C$_3$H$_8$N$_2$+H)$^+$; m/z=197.3 (M+2H)$^{2+}$/2 base peak

EXAMPLE 58 tert-Butyl 3-{[2-(5,6-dimethoxy-1-methyl-1H-pyrrolo[3,2-b]pyridin-3-yl)-1H-pyrrolo[2,3-b]pyridin-4-ylmethyl]amino}azetidine-1-carboxylate Stage 58(a): tert-Butyl 3-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}azetidine-1-carboxylate The product is prepared by following the procedure described in example 52c, starting with 0.3 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine and 0.253 g of 3-amino-1N-Boc-azetidine instead of the N-Boc-ethylenediamine used in example 52c. 0.203 g of tert-butyl 3-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}azetidine-1-carboxylate is obtained with the following characteristics:
Mass spectrum: ES m/z=647 MH$^+$ base peak Stage 58(b): tert-Butyl 3-{[2-(5,6-dimethoxy-1-methyl-1H-pyrrolo[3,2-b]pyridin-3-yl)-1H-pyrrolo[2,3-b]pyridin-4-ylmethyl]amino}azetidine-1-carboxylate The product is prepared by following the procedure described in example 34 stage (k), starting with 0.2 g of tert-butyl 3-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}azetidine-1-carboxylate instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 1.24 cm$^3$ of 5N potassium hydroxide. 0.1 g of tert-butyl 3-{[2-(5,6-dimethoxy-1-methyl-1H-pyrrolo[3,2-b]pyridin-3-yl)-1H-pyrrolo[2,3-b]pyridin-4-ylmethyl]amino}azetidine-1-carboxylate is obtained with the following characteristics:
$^1$H NMR spectrum (300 MHz, (CD$_3$)$_2$SO d6, δ in ppm): 1.36 (s, 9H); 2.88 (broad m, 1H); 3.56 (m, 3H); 3.84 (s, 3H); 3.88 (s, 3H); 3.90 (broad s, 4H); 4.07 (s, 3H); 6.98 (d, J=5.5 Hz, 1H); 7.29 (d, J=2.0 Hz, 1H); 7.58 (s, 1H); 7.89 (s, 1H); 8.04 (d, J=5.5 Hz, 1H); 11.65 (broad m, 1H).
Mass spectrum: ES: m/z=493 MH$^+$ base peak; m/z=437 (M-C$_4$H$_8$+H)$^+$; m/z=321 (M-C$_8$H$_{16}$N$_2$O$_2$+H)$^+$

EXAMPLE 59

[2-(5,6-Dimethoxy-1-methyl-1H-pyrrolo[3,2-b]pyridin-3-yl)-1H-pyrrolo[2,3-b]pyridin-4-ylmethyl]-piperidin-4-ylamine hydrochloride The product is prepared by following the procedure described in example 51, starting with 0.080 g of tert-butyl 4-{[2-(5,6-dimethoxy-1-methyl-1H-pyrrolo[3,2-b]pyridin-3-yl)-1H-pyrrolo[2,3-b]pyridin-4-ylmethyl]amino}piperidine-1-carboxylate instead of the tert-butyl (2-{

[2-(5,6-dimethoxy-1-methyl-1H-pyrrolo[3,2-b]pyridin-3-yl)-1H-pyrrolo[2,3-b]pyridin-4-ylmethyl]amino}ethyl) carbamate used in example 51 and 1.2 cm³ of 5N hydrochloric acid in dioxane. 0.087 g of azetidin-3-yl-[2-(5,6-dimethoxy-1-methyl-1H-pyrrolo[3,2-b]pyridin-3-yl)-1H-pyrrolo[2,3-b]pyridin-4-ylmethyl]amine hydrochloride is obtained with the following characteristics:

$^1$H NMR spectrum (300 MHz, (CD$_3$)$_2$SO d6, δ in ppm): 1.92 (broad m, 2H); 2.37 (m, 2H); 2.45 (partially masked m, 1H); 2.94 (m, 2H); 3.40 (partially masked m, 2H); 3.88 (s, 3H); 3.90 (s, 3H); 4.10 (s, 3H); 4.49 (m, 2H); 7.32 (d, J=5.5 Hz, 1H); 7.40 (d, J=2.0 Hz, 1H); 7.61 (s, 1H); 7.96 (s, 1H); 8.20 (d, J=5.5 Hz, 1H); from 8.80 to 9.03 (broad m, 2H); 9.62 (broad m, 2H); 12.1 (broad m, 1H).

Mass spectrum: IE m/z=420 M$^+$; m/z=322 (M-C$_5$H$_{10}$N$_2$)$^+$; m/z=36 HCl$^+$. base peak

EXAMPLE 60 tert-Butyl 4-{[2-(5,6-dimethoxy-1-methyl-1H-pyrrolo[3,2-b]pyridin-3-yl)-1H-pyrrolo[2,3-b]pyridin-4-ylmethyl]amino}piperidine-1-carboxylate Stage 60(a): tert-Butyl 4-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}piperidine-1-carboxylate The product is prepared by following the procedure described in example 52c, starting with 0.3 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine and 0.253 g of 4-amino-1-Boc-piperidine instead of the N-Boc-ethylenediamine used in example 52c. 0.161 g of tert-butyl 4-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}piperidine-1-carboxylate is obtained with the following characteristics:

Mass spectrum: IE m/z=674 M$^+$; m/z=519 (M-C$_7$H$_7$SO$_2$)$^+$; m/z=321 (m/z=519-C$_{10}$H$_{18}$N$_2$O$_2$)$^+$ base peak Stage 60(b): tert-Butyl 4-{[2-(5,6-dimethoxy-1-methyl-1H-pyrrolo[3,2-b]pyridin-3-yl)-1H-pyrrolo[2,3-b]pyridin-4-ylmethyl]amino}piperidine-1-carboxylate The product is prepared by following the procedure described in example 34 stage (k), starting with 0.160 g of tert-butyl 4-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}piperidine-1-carboxylate instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 0.95 cm³ of 5N potassium hydroxide. 0.104 g of tert-butyl 4-{[2-(5,6-dimethoxy-1-methyl-1H-pyrrolo[3,2-b]pyridin-3-yl)-1H-pyrrolo[2,3-b]pyridin-4-ylmethyl]amino}piperidine-1-carboxylate is obtained with the following characteristics:

$^1$H NMR spectrum (300 MHz, (CD$_3$)$_2$SO d6, δ in ppm): 1.20 (m, 2H); 1.40 (s, 9H); 1.85 (m, 2H); 2.10 (broad m, 1H); 2.64 (m, 1H); 2.80 (m, 2H); 3.81 (m, 2H); 3.83 (s, 3H); 3.89 (s, 3H); 4.02 (broad s, 2H); 4.06 (s, 3H); 7.02 (d, J=5.5 Hz, 1H); 7.30 (d, J=2.0 Hz, 1H); 7.59 (s, 1H); 7.89 (s, 1H); 8.03 (d, J=5.5 Hz, 1H); 11.6 (broad m, 1H).

Mass spectrum: IC m/z=521 MH$^+$ base peak

EXAMPLE 61

{[2-(5,6-Dimethoxy-1-methyl-1H-pyrrolo[3,2-b]pyridin-3-yl)-1H-pyrrolo[2,3-b]pyridin-4-ylmethyl]amino}acetic acid trifluoroacetate Stage 61(a): tert-Butyl {[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}acetate The product is prepared by following the procedure described in example 52c, starting with 0.3 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine and 0.193 g of glycine tert-butyl ester instead of the N-Boc-ethylenediamine used in example 52c. 0.174 g of tert-butyl {[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}-acetate is obtained with the following characteristics:

Mass spectrum: ES m/z=606 MH$^+$ base peak

Stage 61(b): {[2-(5,6-Dimethoxy-1-methyl-1H-pyrrolo[3,2-b]pyridin-3-yl)-1H-pyrrolo[2,3-b]pyridin-4-ylmethyl]amino}acetic acid trifluoroacetate The product is prepared by following the procedure described in example 34 stage (k), starting with 0.170 g of tert-butyl {[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}acetate instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 1.12 cm³ of 5N potassium hydroxide. After purification by preparative LC/MS (acetonitrile/water/trifluoroacetic acid as eluents), 0.034 g of {[2-(5,6-dimethoxy-1-methyl-1H-pyrrolo[3,2-b]pyridin-3-yl)-1H-pyrrolo[2,3-b]pyridin-4-ylmethyl]amino}acetic acid trifluoroacetate is obtained with the following characteristics:

$^1$H NMR spectrum (300 MHz, (CD$_3$)$_2$SO d6, δ in ppm): 3.86 (s, 3H); 3.88 (s, 3H); 4.00 (broad s, 2H); 4.11 (s, 3H); 4.49 (broad s, 2H); 7.14 (d, J=5.5 Hz, 1H); 7.39 (d, J=2.0 Hz, 1H); 7.59 (s, 1H); 7.92 (s, 1H); 8.18 (d, J=5.5 Hz, 1H); 9.50 (broad m, 2H); 11.95 (broad m, 1H); 13.9 (very broad m, 1H).

Mass spectrum: ES m/z=396 MH$^+$ base peak

EXAMPLE 62

5,6-Dimethoxy-1-methyl-3-[4-(thiophen-2-ylsulfanylmethyl)-1H-pyrrolo[2,3-b]pyridin-2-yl]-1H-pyrrolo[3,2-b]pyridine Stage 62(a): 5,6-Dimethoxy-1-methyl-3-[4-(thiophen-2-ylsulfanylmethyl)-1-(toluene-4-sulfonyl)-1H-pyrrolo[2,3-b]pyridin-2-yl]-1H-pyrrolo[3,2-b]pyridine To a solution of 0.1 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine in 5 cm³ of dichloromethane, at a temperature in the region of 20° C., are added 1 g of methyltrioctylammonium chloride, 10 cm³ of water and 0.015 g of sodium hydroxide. The reaction medium is stirred at room temperature for 18 hours. After separation of the phases by settling, the organic phase is dried over magnesium sulfate, filtered and then concentrated under reduced pressure. After purification by flash column chromatography (SiO$_2$, dichloromethane/methanol 98/02 by volume as eluents), 0.11 g of 5,6-dimethoxy-1-methyl-3-[4-(thiophen-2-ylsulfanylmethyl)-1-(toluene-4-sulfonyl)-1H-pyrrolo[2,3-b]pyridin-2-yl]-1H-pyrrolo[3,2-b]pyridine is obtained with the following characteristics:

Mass spectrum: ES m/z=591 MH$^+$ base peak

Stage 62(b): 5,6-Dimethoxy-1-methyl-3-[4-(thiophen-2-ylsulfanylmethyl)-1H-pyrrolo[2,3-b]pyridin-2-yl]-1H-pyrrolo[3,2-b]pyridine The product is prepared by following the procedure described in example 34 stage (k), starting with 0.110 g of 5,6-dimethoxy-1-methyl-3-[4-(thiophen-2-ylsulfanylmethyl)-1-(toluene-4-sulfonyl)-1H-pyrrolo[2,3-b]pyridin-2-yl]-1H-pyrrolo[3,2-b]pyridine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 0.8 cm$^3$ of 5N potassium hydroxide. 0.080 g of 5,6-dimethoxy-1-methyl-3-[4-(thiophen-2-ylsulfanylmethyl)-1H-pyrrolo[2,3-b]pyridin-2-yl]-1H-pyrrolo[3,2-b]pyridine is obtained with the following characteristics:

$^1$H NMR spectrum (300 MHz, (CD$_3$)$_2$SO d6, δ in ppm): 3.85 (s, 3H); 3.89 (s, 3H); 4.09 (s, 3H); 4.33 (broad s, 2H); 6.79 (d, J=5.5 Hz, 1H); 6.97 (dd, J=3.5 and 5.5 Hz, 1H); 7.17 (dd, J=1.5 and 3.5 Hz, 1H); 7.30 (d, J=2.0 Hz, 1H); 7.57 (dd, J=1.5 and 5.5 Hz, 1H); 7.59 (s, 1H); 7.89 (s, 1H); 7.98 (d, J=5.5 Hz, 1H); 11.7 (broad m, 1H).

Mass spectrum: ES m/z=437 MH$^+$ base peak

EXAMPLE 63

5,6-Dimethoxy-1-methyl-3-(4-phenoxymethyl-1H-pyrrolo[2,3-b]pyridin-2-yl)-1H-pyrrolo[3,2-b]pyridine Stage 63(a): 5,6-Dimethoxy-1-methyl-3-[4-phenoxymethyl-1-(toluene-4-sulfonyl)-1H-pyrrolo[2,3-b]pyridin-2-yl]-1H-pyrrolo[3,2-b]pyridine To a solution of 0.3 g of 3-[4-chloromethyl-1-(toluene-4-sulfonyl)-1H-pyrrolo[2,3-b]pyridin-2-yl]-5,6-dimethoxy-1-methyl-1H-pyrrolo[3,2-b]pyridine in 30 cm$^3$ of acetonitrile, at a temperature in the region of 20° C., are added 0.066 cm$^3$ of phenol and 0.486 g of potassium carbonate. The reaction medium is heated at 80° C. for 18 hours. After cooling, the reaction medium is filtered through a sinter funnel and the filtrate is concentrated under reduced pressure. The residue obtained is taken up in 5 cm$^3$ of water and 10 cm$^3$ of dichloromethane. After separation of the phases by settling, the organic phase is dried over magnesium sulfate, filtered and then concentrated under reduced pressure. After purification by flash column chromatography (SiO$_2$, dichloromethane/ethyl acetate 97.5/2.5 by volume as eluents), 0.140 g of 5,6-dimethoxy-1-methyl-3-[4-phenoxymethyl-1-(toluene-4-sulfonyl)-1H-pyrrolo[2,3-b]pyridin-2-yl]-1H-pyrrolo[3,2-b]pyridine is obtained with the following characteristics:

Mass spectrum: ES m/z=569 MH$^+$ base peak

Stage 63(b): 5,6-Dimethoxy-1-methyl-3-(4-phenoxymethyl-1H-pyrrolo[2,3-b]pyridin-2-yl)-1H-pyrrolo[3,2-b]pyridine The product is prepared by following the procedure described in example 34 stage (k), starting with 0.140 g of 5,6-dimethoxy-1-methyl-3-[4-phenoxymethyl-1-(toluene-4-sulfonyl)-1H-pyrrolo[2,3-b]pyridin-2-yl]-1H-pyrrolo[3,2-b]pyridine instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 1.2 cm$^3$ of 5N potassium hydroxide. 0.095 g of 5,6-dimethoxy-1-methyl-3-(4-phenoxymethyl-1H-pyrrolo[2,3-b]pyridin-2-yl)-1H-pyrrolo[3,2-b]pyridine is obtained with the following characteristics:

$^1$H NMR spectrum (300 MHz, (CD$_3$)$_2$SO d6, δ in ppm): 3.83 (s, 3H); 3.87 (s, 3H); 3.97 (s, 3H); 5.42 (s, 2H); 6.93 (broad t, J=7.5 Hz, 1H); from 7.03 to 7.09 (m, 3H); 7.30 (m, 2H); 7.33 (d, J=2.0 Hz, 1H); 7.58 (s, 1H); 7.91 (s, 1H); 8.09 (d, J=5.5 Hz, 1H); 11.75 (broad m, 1H).

Mass spectrum: ES m/z=415 MH$^+$ base peak

EXAMPLE 64

2-{[2-(5,6-Dimethoxy-1-methyl-1H-pyrrolo[3,2-b]pyridin-3-yl)-1H-pyrrolo[2,3-b]pyridin-4-ylmethyl]amino}-2-phenylethanol trifluoroacetate Stage 64(a): [2-(5,6-Dimethoxy-1-methyl-1H-pyrrolo[3,2-b]pyridin-3-yl)-1-(toluene-4-sulfonyl)-1H-pyrrolo[2,3-b]pyridin-4-yl]methylamine To a solution of 0.5 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-carbaldehyde oxime in 30 cm$^3$ of ethanol and 25 cm$^3$ of water, at a temperature in the region of 20° C., are added 0.65 g of zinc and 17.5 cm$^3$ of concentrated formic acid. The reaction medium is stirred at room temperature for 8 days. The reaction medium is concentrated under reduced pressure. The residue obtained is taken up in methanol, basified with sodium hydroxide (30%) to pH=9-10 and then filtered through Celite. The filtrate is concentrated under reduced pressure and the residue obtained is purified by flashpack chromatography (SiO$_2$, dichloromethane/methanol 95/05 by volume as eluents). 0.1 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-yl]methylamine is obtained with the following characteristics:

$^1$H NMR spectrum (300 MHz, (CD$_3$)$_2$SO d6, δ in ppm): 2.29 (s, 3H); 3.83 (s, 3H); 3.89 (s, 6H); 3.92 (broad s, 2H); 6.99 (s, 1H); 7.28 (broad d, J=9.0 Hz, 2H); 7.30 (partially masked m, 1H); 7.56 (s, 1H); 7.61 (s, 1H); 7.77 (broad d, J=9.0 Hz, 2H); 8.21 (d, J=5.5 Hz, 1H) and 0.04 g of N-[2-(5,6-dimethoxy-1-methyl-1H-pyrrolo[3,2-b]pyridin-3-yl)-1H-pyrrolo[2,3-b]pyridin-4-ylmethyl]formamide is obtained with the following characteristics:

$^1$H NMR spectrum (300 MHz, (CD$_3$)$_2$SO d6, δ in ppm): 3.84 (s, 3H); 3.88 (s, 3H); 4.07 (s, 3H); 4.61 (broad d, J=6.0 Hz, 2H); 6.90 (d, J=5.5 Hz, 1H); 7.28 (d, J=2.0 Hz, 1H); 7.58 (s, 1H); 7.89 (s, 1H); 8.04 (d, J=5.5 Hz, 1H); 8.21 (broad s, 1H); 8.56 (broad t, J=6.0 Hz, 1H); 11.7 (broad m, 1H).

Mass spectrum: ES m/z=366 MH$^+$ base peak

Stage 64(b): 2-{[2-(5,6-Dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}-1-phenylethanol and 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}-2-phenylethanol To a solution of 0.09 g of [2-(5,6-dimethoxy-1-methyl-1H-pyrrolo[3,2-b]pyridin-3-yl)-1-(toluene-4-sulfonyl)-1H-pyrrolo[2,3-b]pyridin-4-yl]methylamine in 20 cm³ of ethanol, at a temperature in the region of 20° C., is added 0.022 g of styrene oxide. The reaction medium is refluxed for five days. After cooling, the reaction medium is concentrated under reduced pressure. The residue obtained is purified by flash-pack column chromatography ($SiO_2$, dichloromethane/methanol 95/05 by volume as eluents) to give 0.008 g of 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}-2-phenylethanol with the following characteristics:

Mass spectrum: ES m/z=612 MH⁺ base peak and 0.01 g of 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}-1-phenylethanol with the following characteristics:

Mass spectrum: ES m/z=612 MH⁺ base peak

Stage 64(c): 2-{[2-(5,6-Dimethoxy-1-methyl-1H-pyrrolo[3,2-b]pyridin-3-yl)-1H-pyrrolo[2,3-b]pyridin-4-ylmethyl]amino}-2-phenylethanol trifluoroacetate The product is prepared by following the procedure described in example 34 stage (k), starting with 0.008 g of 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-yl-methyl-]amino}-2-phenylethanol instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage (k) and 1.2 cm³ of 5N potassium hydroxide. After purification by preparative LC/MS (acetonitrile/water/trifluoroacetic acid as eluents), 0.008 g of 2-{[2-(5,6-dimethoxy-1-methyl-1H-pyrrolo[3,2-b]pyridin-3-yl)-1H-pyrrolo[2,3-b]pyridin-4-ylmethyl]amino}-2-phenylethanol trifluoroacetate is obtained with the following characteristics:

¹H NMR spectrum (300 MHz, $(CD_3)_2SO$ d6, δ in ppm): 3.85 (s, 3H); 3.89 (s, 5H); 4.00 (s, 3H); 4.22 (broad m, 1H); 4.45 (broad m, 2H); 5.63 (broad m, 1H); 7.11 (d, J=2.0 Hz, 1H); 7.18 (d, J=5.5 Hz, 1H); 7.48 (m, 3H); 7.53 (m, 2H); 7.60 (s, 1H); 7.90 (s, 1H); 8.17 (d, J=5.5 Hz, 1H); 9.53 (broad m, 2H); 11.95 (broad m, 1H).

Mass spectrum: ES m/z=458 MH⁺ base peak; m/z=321 $(M-C_8H_{11}NO+H)^+$

EXAMPLE 65

2-{[2-(5,6-Dimethoxy-1-methyl-1H-pyrrolo[3,2-b]pyridin-3-yl)-1H-pyrrolo[2,3-b]pyridin-4-ylmethyl]amino}-1-phenylethanol trifluoroacetate The product is prepared by following the procedure described in example 34 stage (k), starting with 0.010 g of 2-{[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amino}-1-phenylethanol instead of the cyclopropyl-[2-(5,6-dimethoxy-1-methyl-1H-pyrrolo[3,2-b]pyridin-3-yl)-1-(toluene-4-sulfonyl)-1H-pyrrolo[2,3-b]pyridin-4-ylmethyl]amine used in example 34 stage(k) and 0.008 cm³ of 5N potassium hydroxide. After purification by preparative LC/MS (acetonitrile/water/trifluoroacetic acid as eluents), 0.008 g of 2-{[2-(5,6-dimethoxy-1-methyl-1H-pyrrolo[3,2-b]pyridin-3-yl)-1H-pyrrolo[2,3-b]pyridin-4-ylmethyl]amino}-1-phenylethanol trifluoroacetate is obtained with the following characteristics:

¹H NMR spectrum (300 MHz, $(CD_3)_2SO$ d6, δ in ppm) from 3.05 to 3.30 (partially masked m, 2H); 3.86 (s, 3H); 3.87 (s, 3H); 4.03 (s, 3H); 4.55 (m, 2H); 4.97 (m, 1H); 6.20 (m, 1H); 7.20 (d, J=5.5 Hz, 1H); from 7.27 to 7.42 (m, 6H); 7.59 (s, 1H); 7.91 (s, 1H); 8.18 (d, J=5.5 Hz, 1H); 9.20 (broad m, 2H); 11.95 (broad m, 1H).

Mass spectrum: IE and ES m/z=458 MH⁺; base peak; m/z=321 $(M-C_8H_{11}NO+H)^+$

EXAMPLE 66

Pharmaceutical Composition

| Tablets were prepared corresponding to the following formula: | |
|---|---|
| Product of example 1 | 0.2 g |
| Excipient for one tablet made up to | 1 g |

(details of the excipient: lactose, talc, starch, magnesium stearate).

EXAMPLE 67

Pharmaceutical Composition

| Tablets were prepared corresponding to the following formula: | |
|---|---|
| Product of example 8 | 0.2 g |
| Excipient for one tablet made up to | 1 g |

(details of the excipient: lactose, talc, starch, magnesium stearate).

The above pharmaceutical compositions that constitute examples 66 and 67 of the present invention can be prepared in the same manner with the other products of formula (I) according to the present invention and especially with the products given as examples in the above experimental section.

What is claimed is:
1. A compound according to formula (Ib):

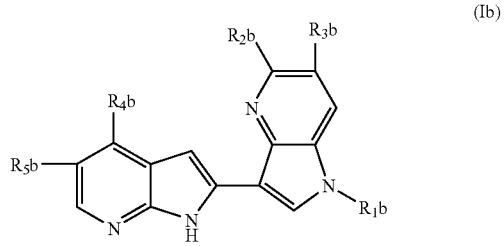

in which:

R1b represents alkyl containing 1 to 2 carbon atoms and optionally substituted by a morpholino or piperazinyl radical itself optionally substituted by an alkyl radical, R2b and R3b, which may be identical or different, represent alkoxy, R4b represents a hydrogen atom, a halogen atom or a CH2NR6R7 radical, wherein R6 and R7, which may be identical or different, are selected ti:om hydrogen, alkyl, alkoxy, alkenyl, cycloalkyl, cycloalkenyl, heterocycloalkyl, aryl, heteroaryl, cycloalkylalkyl, heterocycloalkylalkyl, aralkyl and heteroaralkyl, all these radicals being optionally substituted, or alternatively R6 and R7 form, with the nitrogen atom to which they are bound, a heterocyclic radical, unsaturated or alternatively partially or fully saturated, made up of 3 to 10 units and containing one or more heteroatoms selected from O, S, N and NR8, this heterocyclic radical being optionally substituted;

R8 represents a hydrogen atom or an acyl, alkyl or aryl radical, optionally substituted;

R5b represents hydrogen or fluorine, or an addition salt of said compound with a mineral or organic acid or with a mineral or organic base.

2. A compound selected from the group consisting of:

5,6-Dimethoxy-1-methyl-3-(1H-pyrrolo[2,3-b]pyridin-2-yl)-1H-pyrrolo[3,2-b]pyridine;

5,6-dimethoxy-1-(2-morpholin-4-ylethyl)3-(1H-pyrrolo[2,3-b]pyridin-2-yl)-1H-pyrrolo -[3,2-b]pyridine;

5,6-dimethoxy-1-[2-(4-methylpiperazin-1-yl)ethyl]-3-(1H-pyrrolo[2,3-b]pyridin-2-yl)-1H-pyrrolo[3,2-b]pyridine;

3-(4-chloro-1H-pyrrolo [2,3-b]pyridin-2-yl)-5,6-dimethoxy-1-methyl-1H-pyrrolo [3,2-b]-pyridine;

3-(4-chloro-1H-pyrrolo[2,3-b]pyridin-2-yl)-5,6-dimethoxy-1-(2-morpholin-4-ylethyl)-1H-pyrrolo[3,2-b]pyridine;

3-(4-chloro-1H-pyrrolo[2,3-b]pyridin-2-yl)-5,6-dimethoxy-1-[2-(4-methylpiperazin-1-yl)ethyl]-1H-pyrrolo[3,2-b]pyridine;

3-(5-fluoro-1H-pyrrolo[2,3-b]pyridin-2-yl)-5,6-dimethoxy-1-(2-morpholin-4-ylethyl)-1H-pyrrolo[3,2-b]pyridine; and 3-(4-chloro-5-fluoro-1H-pyrrolo[2,3-b]pyridin-2-yl)-5,6-dimethoxy-1-(2-morpholin-4-ylethyl)-1H-pyrrolo[3,2-b]pyridine;

or an addition salt of said compound with a mineral or organic acid or with a mineral or organic base.

3. A compound selected from the group consisting of:

3-(4-chloro-5-fluoro-1H-pyrrolo[2,3-b]pyridin-2-yl)-5,6-dimethoxy-1-[2-(4-methylpiperazin-1-yl)ethyl]-1H-pyrrolo[3,2-b]pyridine;

3-[4-chloro-5-fluoro-1H-pyrrolo[2,3-b]pyridin-2-yl]-5,6-dimethoxy-1-(3-piperidin-1-ylpropyl) -1H-pyrrolo[3,2-b]pyridine;

1-{3-[3-(4-chloro-5-fluoro-1H-pyrrolo[2,3-b]pyridin-2-yl)-5,6-dimethoxypyrrolo[3,2-b]pyridin-1-yl] propyl}piperidin-4-ol;

C-(1-{2-[3-(4-chloro-1H-pyrrolo[2,3-b]pyridin-2-yl)-5,6-dimethoxypyrrolo[3,2-b]pyridin-1-yl] ethyl}piperidin-4-yl)methylamine;

2-[3-(4-chloro-1H-pyrrolo[2,3-b]pyridin-2-yl)-5,6-dimethoxypyrrolo[3,2-b]pyridin-1-yl]-1-(4-methylpiperazin-1-yl)ethanone;

{3-[3-(4-chloro-1H-pyrrolo[2,3-b]pyridin-2-yl)-5,6-dimethoxypyrrolo[3,2-b]pyridin-1-yl] propyl}diethylamine;

3-(4-chloro-1H-pyrrolo[2,3-b]pyridin-2-yl)-5,6-dimethoxy-1-[3-(4-methylperhydro-1,4-diazepin-1-yl) propyl]-1H-pyrrolo[3,2-b]pyridine;

2-(5,6-dimethoxy-1-methyl-1H-pyrrolo[3,2-b]pyridin-3-yl)-1H-pyrrolo[2,3-b]pyridine-4-carbonitrile;

2-[3-(4-chloro-1H-pyrrolo[2,3-b]pyridin-2-yl)-5,6-dimethoxypyrrolo[3,2-b]pyridin-1-yl]-N-methoxy-N-methylacetamide;

[2-(5,6-dimethoxy-1-methyl-1H-pyrrolo[3,2-b]pyridin-3-yl)-1H-pyrrolo[2,3-b]pyridin-4-ylmethyl]-(4-morpholin-4-ylphenyl)amine;

[2-(5,6-dimethoxy-1-methyl-1H-pyrrolo[3,2-b]pyridin-3-yl)-1H-pyrrolo[2,3-b]pyridin-4-carbaldehyde oxime; and 4-{[2-(5,6-dimethoxy-1-methyl-1H-pyrrolo[3,2-b]pyridin-3-yl)-1H-pyrrolo[2,3-b]pyridin-4-ylmethyl] amino}phenol;

or an addition salt of said compound with a mineral or organic acid or with a mineral or organic base.

4. A pharmaceutical composition containing, as active principle, at least one compound according to claim 1, or a pharmaceutically acceptable salt thereof, and a pharmaceutically acceptable excipient.

5. A pharmaceutical composition containing, as active principle, at least one compound according to claim 2, or a pharmaceutically acceptable salt thereof, and a pharmaceutically acceptable excipient.

6. A pharmaceutical composition containing, as active principle, at least one compound according to claim 3, or a pharmaceutically acceptable salt thereof, and a pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,786,114 B2 | Page 1 of 2 |
| APPLICATION NO. | : 11/692321 | |
| DATED | : August 31, 2010 | |
| INVENTOR(S) | : Conception Nemecek et al. | |

It is certified that error appears in the above-identified patent and that said Letters Patent is hereby corrected as shown below:

In column 19, line 14, delete "tributyultin" and insert -- tributyltin --, therefor.

In column 35, line 4, delete "pyridin-$^2$-yl)" and insert -- pyridin-2-yl) --, therefor.

In column 36, lines 64-65, delete "olomucine," and insert -- olomoucine, --, therefor.

In column 37, line 11, delete "biphophonates" and insert -- biphosphonates --, therefor.

In column 38, lines 30-34, delete " [DMAP / TEA / Boc₂O / DMF / 96%] " and insert -- [DMAP / TEA / Boc₂O / DMF / 98%] --, therefor.

In column 45, line 26, after "(M+1)" insert -- . --.

In column 46, line 10, after "(s, 0.56 H)," delete "is".

In column 46, line 18, delete "nmmol)," and insert -- mmol), --, therefor.

In column 46, line 18, delete "nmmol)," and insert -- mmol), --, therefor.

In column 46, line 19, delete "ACOH" and insert -- AcOH --, therefor.

In column 46, lines 63-64, delete "tributylotannanyl" and insert -- tributylstannanyl --, therefor.

In column 46, line 67, delete "nmmol)" and insert -- mmol) --, therefor.

In column 47, line 57, delete "nmmol," and insert -- mmol, --, therefor.

In column 53, line 40, delete "(CDCl$_3$." and insert -- (CDCl$_3$) --, therefor.

In column 56, line 65, delete "pp—" and insert -- ppm— --, therefor.

In column 68, line 5, delete "(S," and insert -- (s, --, therefor.

Signed and Sealed this
Twenty-sixth Day of June, 2012

David J. Kappos
*Director of the United States Patent and Trademark Office*

CERTIFICATE OF CORRECTION (continued)
U.S. Pat. No. 7,786,114 B2

In column 71, line 28, delete "(S," and insert -- (s, --, therefor.

In column 75, line 37, after "with the" delete "15".

In column 87, line 27, delete "[$^2$-" and insert -- [2- --, therefor.

In column 97, line 17, delete "1H" and insert -- $^1$H --, therefor.

In column 107, line 11, in claim 1, delete "ti:om" and insert -- from --, therefor.